(12) United States Patent
Lotersztajn et al.

(10) Patent No.: US 10,076,517 B2
(45) Date of Patent: Sep. 18, 2018

(54) METHODS AND PHARMACEUTICAL COMPOSITIONS FOR THE TREATMENT OF FIBROSIS

(71) Applicants: INSERM (INSTITUT NATIONAL DE LA SANTÉ ET DE LA RECHERCHE MÉDICALE), Paris (FR); UNIVERSITÉ PARIS DIDEROT-PARIS 7, Paris (FR); CENTRE NATIONAL DE LA RECHERCHE SCIENTIFIQUE (CNRS), Paris (FR)

(72) Inventors: Sophie Lotersztajn, Paris (FR); Aïda Habib, Paris (FR)

(73) Assignees: INSERM (INSTITUT NATIONAL DE LA SANTÉ ET DE KA RECHERCHE MÉDICALE, Paris (FR); UNIVERSTÉ PARIS DIDEROT—PARIS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/512,872

(22) PCT Filed: Sep. 21, 2015

(86) PCT No.: PCT/EP2015/071597
§ 371 (c)(1),
(2) Date: Mar. 21, 2017

(87) PCT Pub. No.: WO2016/046130
PCT Pub. Date: Mar. 31, 2016

(65) Prior Publication Data
US 2017/0239242 A1 Aug. 24, 2017

(30) Foreign Application Priority Data

Sep. 22, 2014 (EP) .................................... 14306456

(51) Int. Cl.
*A61K 31/4015* (2006.01)
*A61K 31/4525* (2006.01)
*A61K 31/496* (2006.01)
*A61K 31/4535* (2006.01)
*A61K 31/454* (2006.01)
*A61K 31/4545* (2006.01)

(52) U.S. Cl.
CPC ........ *A61K 31/496* (2013.01); *A61K 31/4015* (2013.01); *A61K 31/454* (2013.01); *A61K 31/4525* (2013.01); *A61K 31/4535* (2013.01); *A61K 31/4545* (2013.01)

(58) Field of Classification Search
CPC ............ A61K 31/4015; A61K 31/4525; A61K 31/496; A61K 31/4535; A61K 31/454; A61K 31/4545
See application file for complete search history.

(56) References Cited

U.S. PATENT DOCUMENTS

| | | |
|---|---|---|
| 8,349,842 B2 | 1/2013 | Sun |
| 8,362,000 B2 | 1/2013 | Bian et al. |
| 8,362,001 B2 | 1/2013 | Bian et al. |
| 8,367,653 B2 | 2/2013 | Bian et al. |
| 8,367,697 B2 | 2/2013 | Jimenez et al. |
| 8,399,454 B2 | 3/2013 | Bian et al. |
| 8,415,341 B2 | 4/2013 | Chevalier et al. |
| 8,426,401 B2 | 4/2013 | Bian et al. |
| 8,435,977 B2 | 5/2013 | Flores et al. |
| 8,445,477 B2 | 5/2013 | Bian et al. |
| 8,450,303 B2 | 5/2013 | Bian et al. |
| 8,455,476 B2 | 6/2013 | Bian et al. |
| 8,513,423 B2 | 8/2013 | Connolly et al. |
| 8,575,363 B2 | 11/2013 | Zhang et al. |
| 8,604,017 B2 | 12/2013 | Bian et al. |
| 8,623,858 B2 | 1/2014 | Bian et al. |
| 8,637,498 B2 | 1/2014 | Connolly et al. |
| 8,691,805 B2 | 4/2014 | Bian et al. |
| 8,697,683 B2 | 4/2014 | Bian et al. |
| 8,722,658 B2 | 5/2014 | Bian et al. |
| 8,741,887 B2 | 6/2014 | Bian et al. |
| 8,759,333 B2 | 6/2014 | Connolly et al. |
| 8,759,533 B2 | 6/2014 | Connolly et al. |
| 2010/0124082 A1 | 5/2010 | Lee et al. |
| 2010/0124086 A1 | 5/2010 | Chen |
| 2010/0124102 A1 | 5/2010 | Lee et al. |
| 2010/0124112 A1 | 5/2010 | Kasuga |
| 2010/0124114 A1 | 5/2010 | Kwak et al. |
| 2010/0124116 A1 | 5/2010 | Maeda et al. |
| 2010/0124119 A1 | 5/2010 | Lee et al. |
| 2010/0124121 A1 | 5/2010 | Seo |
| 2010/0124122 A1 | 5/2010 | Jeong et al. |
| 2012/0030907 A1 | 2/2012 | Henninger |
| 2012/0044613 A1 | 2/2012 | Cho et al. |
| 2012/0054716 A1 | 3/2012 | Tailliez et al. |
| 2012/0054721 A1 | 3/2012 | Dadiomov et al. |
| 2012/0058986 A1 | 3/2012 | Connolly et al. |
| 2013/0049289 A1 | 2/2013 | Ichikawa |
| 2013/0049293 A1 | 2/2013 | Reidhaar |

FOREIGN PATENT DOCUMENTS

| | | |
|---|---|---|
| WO | 2004/056800 A1 | 7/2004 |
| WO | 2010/124082 A1 | 10/2010 |
| WO | 2013/049332 A1 | 4/2013 |
| WO | WO -2015/179559 A2 * | 11/2015 |

* cited by examiner

Primary Examiner — Laura L Stockton
(74) Attorney, Agent, or Firm — W&C IP

(57) ABSTRACT

The present invention relates to methods and pharmaceutical compositions for the treatment of fibrosis. In particular, the present invention relates to a method of treating fibrosis in a subject in need thereof comprising administering the subject with a therapeutically effective amount of at least one monoacylglycerol lipase (MGL) inhibitor.

14 Claims, 8 Drawing Sheets

Figure 1:
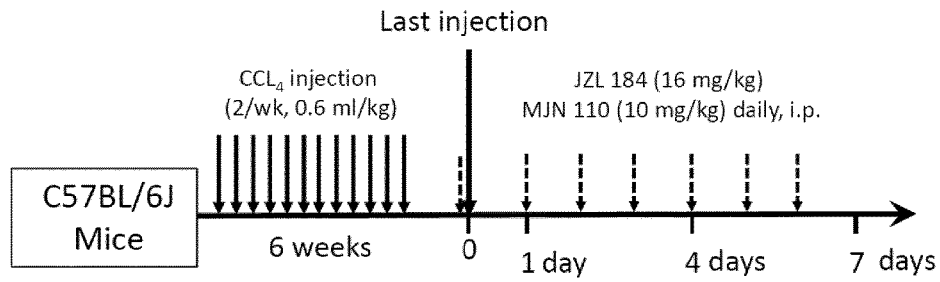

Sirius Red
*4 days*

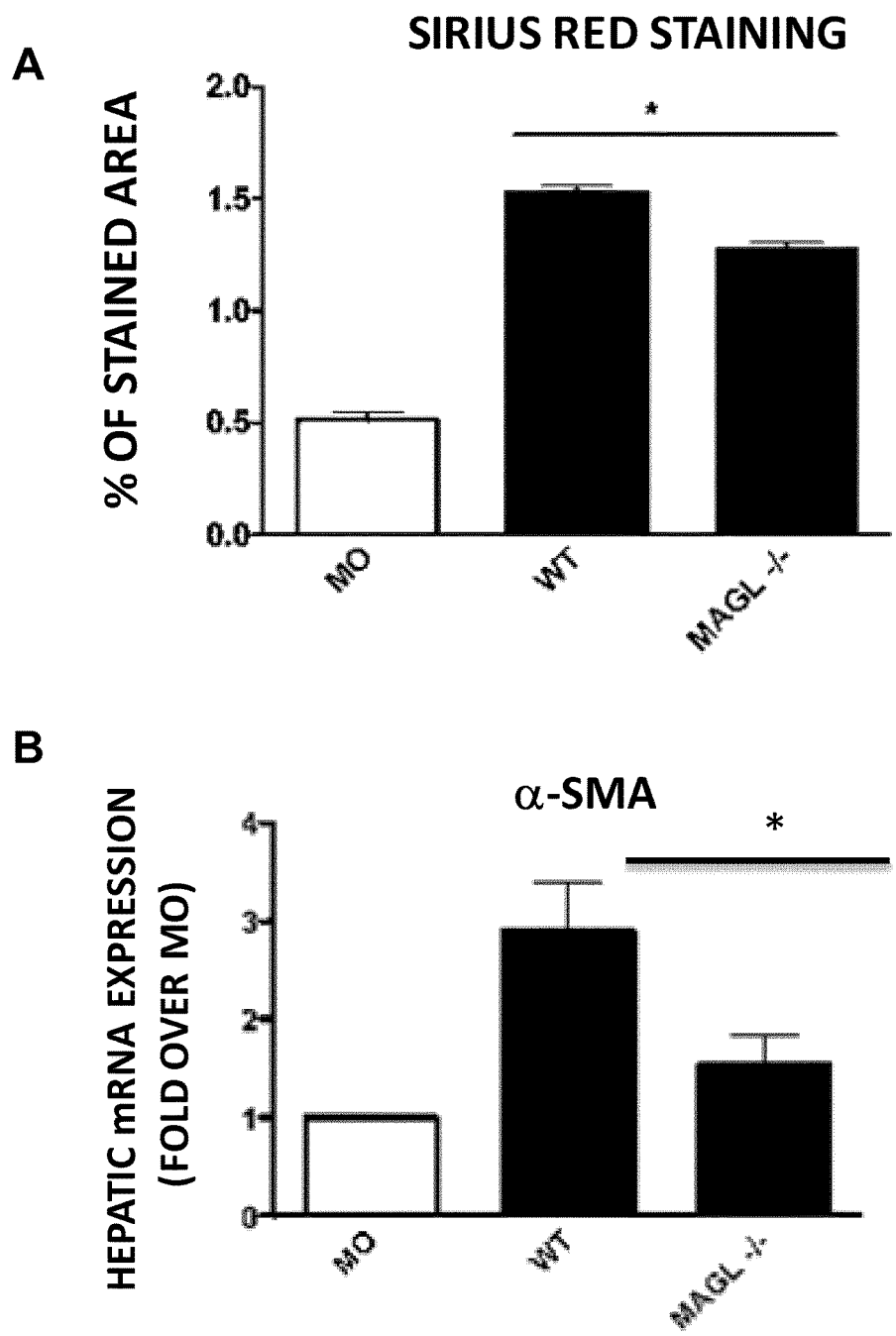
Figure 7 A and B

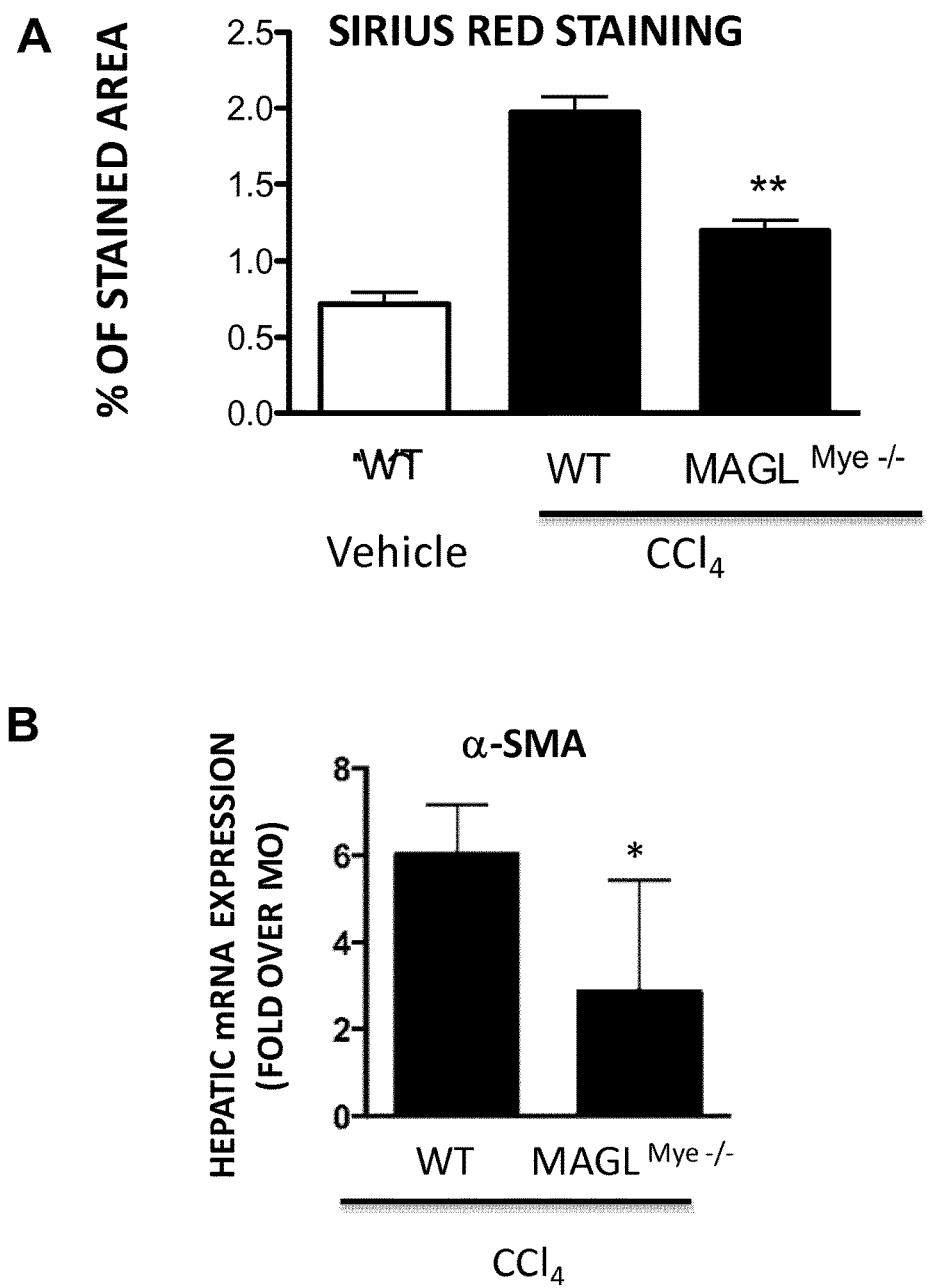
Figure 8 A and B

METHODS AND PHARMACEUTICAL COMPOSITIONS FOR THE TREATMENT OF FIBROSIS

FIELD OF THE INVENTION

The present invention relates to methods and pharmaceutical compositions for the treatment of fibrosis.

BACKGROUND OF THE INVENTION

Fibrosis is the common scarring reaction associated with chronic injury that results from prolonged parenchymal cell injury and/or inflammation that may be induced by a wide variety of agents, e.g., drugs, toxins, radiation, any process disturbing tissue or cellular homeostasis, toxic injury, altered blood flow, infections (viral, bacterial, spirochetal, and parasitic), storage disorders, and disorders resulting in the accumulation of toxic metabolites. Fibrosis is most common in the heart, lung, peritoneum, and kidney.

For instance, hepatic fibrosis (liver fibrosis) results from an altered wound healing response that is characterized by increased production of matrix proteins and decreased matrix remodeling. Normal structural elements of tissues are replaced with excessive amounts of non-functional scar tissue. Hepatic fibrosis is a common pathological consequence of chronic liver diseases. Examples of such chronic liver diseases include chronic hepatitis B and C virus infections, alcoholic liver disease, non-alcoholic steatohepatitis (NASH) and autoimmune liver disease. In a number of patients, fibrosis ultimately leads to cirrhosis, a condition defined by an abnormal liver architecture, with fibrotic septa surrounding regenerating nodules and altered vacularization. Due to decreased functional parenchymal reserve and altered hepatic blood flow, cirrhosis is associated with the life-threatening complications of liver failure including hepatic encephalopathy, coagulation disorders and bacterial infections, and complications of portal hypertension such as ascites, variceal rupture and hepatorenal syndrome. In addition, the cirrhotic liver is a precancerous state, and thus requires the systematic screening for hepatocellular carcinoma. Several clinical reports have documented that regression of liver fibrosis occurs in a substantial proportion of patients, provided that the factor responsible for liver insult is eradicated or controlled (7, 16, 57). Consistent with this observation, studies in rodents have also documented regression of fibrosis or early stage cirrhosis within weeks following eradication of the toxic insult. The potential for reversibility of fibrosis declines at advanced stages. It is imperative to treat fibrosis in the early stages of reversible liver scarring so that irreversible cirrhosis can be prevented.

Monoglyceride Lipase (MGL) is a target known in the art and first identified by Wall et al. (Virus Res. 1997, 52, 152-167) in 1997 and designated HUKS. Dinh et al. (Proc. Nat. Acad. Sci., 2002, 99, 10819-10824) found that the rat MGL participates in inactivation of 2-arachidonoylglycerol (2-AG), an endogenous cannabinoid monoglyceride. It is highly expressed in regions of rat brain that also express cannabinoid receptors and it appears to assume a presynaptic localization in the hippocampus. MGL inhibitors are therefore potentially useful for the treatment of pain, inflammation, and CNS disorders. In addition to the brain, MGL is expressed in adipocytes, where it functions together with hormone-sensitive lipase (LIPE) to hydrolyze intracellular triglyceride stores, and in the intestine, where it is largely responsible for cleaving monoacyglycerols to form free fatty acids and glycerol. These observations implicate MGL in metabolic diseases and suggest that MGL inhibitors will have beneficial effects on metabolic disorders, including obesity, hyperphagia and diabetes. The effect of MGL inhibitors for the treatment of fibrosis has never been investigated in the prior art.

SUMMARY OF THE INVENTION

The present invention relates to methods and pharmaceutical compositions for the treatment of fibrosis. In particular, the present invention is defined by the claims.

DETAILED DESCRIPTION OF THE INVENTION

The present invention relates to a method of treating fibrosis in a subject in need thereof comprising administering the subject with a therapeutically effective amount of at least one monoacylglycerol lipase (MGL) inhibitor.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the fibrosis affects at least one organ selected from the group consisting of skin, heart, liver, lung, or kidney. Examples of fibrosis include, without limitation, dermal scar formation, keloids, liver fibrosis, lung fibrosis, kidney fibrosis, glomerulosclerosis, pulmonary fibrosis (e.g. idiopathic pulmonary fibrosis), liver fibrosis (e.g. following liver transplantation, liver fibrosis following chronic hepatitis C virus infection), renal fibrosis, intestinal fibrosis, interstitial fibrosis, cystic fibrosis of the pancreas and lungs, injection fibrosis, endomyocardial fibrosis, mediastinal fibrosis, myelofibrosis, retroperitoneal fibrosis, progressive massive fibrosis, nephrogenic systemic fibrosis. In some embodiments, the fibrosis is caused by surgical implantation of an artificial organ.

Liver (hepatic) fibrosis, for example, occurs as a part of the wound-healing response to chronic liver injury. Such damage may be the result of viral activity (e.g., chronic hepatitis types B or C) or other infections (e.g., parasites, bacteria), chemicals (e.g., pharmaceuticals, alcohol, pollutants), immune processes (e.g., autoimmune hepatitis), metabolic disorders (e.g., lipid, glycogen, or metal storage disorders), or cancer growth. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

Fibrotic disorders of the kidney include, without limitation, diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, renal interstitial fibrosis, renal fibrosis in patients receiving cyclosporin, and HIV associated nephropathy. The glomerulus is a major target of many types of renal injury, including immunologic (e.g., immune-complex- or T-cell-mediated), hemodynamic (systemic or renal hypertension), metabolic (e.g., diabetes), "atherosclerotic" (accumulation of lipids in the glomerulus), infiltrative (e.g., amyloid), and toxicant (e.g., snake venom). The renal structural changes in patients with diabetic nephropathy include hypertrophy of the glomerulus, thickening of the glomerular and tubular membranes (due to accumulated matrix), and increased amounts of matrix in the measangium and tubulointerstitium. Glomerular hypertension due to intrarenal hemodynamic changes in diabetes can contribute to the progression of diabetic nephropathy. Autoimmune nephritis can also lead to altered mesangial cell growth responses. Infection by hepatitis-C virus can also result in idiopathic membranoproliferative glomerulonephritis.

Fibrotic disorders of the lung include, without limitation, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C. The method of the present invention can also be utilized to treat a subject having asthma and other conditions of the lung associated with airway remodeling.

Pancreatic fibrosis occurs in chronic pancreatitis. This condition is characterized by duct calcification and fibrosis of the pancreatic parenchyma. Like liver cirrhosis, chronic pancreatitis is associated with alcohol abuse.

The method of the present invention is also suitable for the treatment of intestinal fibrosis, particularly fibrosis associated with inflammatory bowel diseases (e.g., Crohn's disease and ulcerative colitis).

Dermal fibrotic conditions which may be treated by the method of the present invention include, but are not limited to, keloids, hypertrophic scars, familial cutaneous collagenoma, and connective tissue nevi of the collagen type. In addition, the method of the present invention are suitable for inhibiting overproduction of scarring in patients who are known to form keloids or hypertrophic scars, inhibiting or preventing scarring or overproduction of scarring during healing of various types of wounds including surgical incisions, surgical abdominal wounds and traumatic lacerations, preventing or inhibiting scarring and reclosing of arteries following coronary angioplasty, and preventing or inhibiting excess scar or fibrous tissue formation associated with cardiac fibrosis after infarction and in hypersensitive vasculopathy.

Fibrotic conditions of the eye include conditions such as diabetic retinopathy, postsurgical fibrotic conditions (for example, after glaucoma filtering surgery and after cross-eye surgery), and proliferative vitreoretinopathy.

Fibroproliferative disorders of bone are characterized by aberrant and ectopic bone formation, commonly seen as active proliferation of the major cell types participating in bone formation as well as elaboration by those cells of a complex bone matrix. Exemplary of such bone disorders is the fibrosis that occurs with prostate tumor metastases to the axial skeleton. In prostate tumor-related cancellous bone growth, prostate carcinoma cells can interact reciprocally with osteoblasts to produce enhanced tumor growth and osteoblastic action when they are deposited in bone. Fibroproliferative responses of the bone originating in the skeleton per se include ostepetrosis and hyperstosis. A defect in osteoblast differentiation and function is thought to be a major cause in osteopetrosis, an inherited disorder characterized by bone sclerosis due to reduced bone resorption, marrow cavities fail to develop, resulting in extramedullary hematopoiesis and severe hematologic abnormalities associated with optic atrophy, deafibronectiness, and mental retardation. In osteoarthritis, bone changes are known to occur, and bone collagen metabolism is increased within osteoarthritic femoral heads. The greatest changes occur within the subchondral zone, supporting a greater proportion of osteoid in the diseased tissue.

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a classic fibroproliferative disease.

Additional fibrotic conditions which may be treated by the method of the present invention include: diseases associated with prolonged joint pain and deteriorated joints, progressive systemic sclerosis, dermatomyositis, Raynaud's syndrome, and nasal polyposis.

In some embodiments, the method of the present invention is particularly suitable for the treatment of inflammation-induced fibrosis. As used herein, the expression "inflammation-induced fibrosis" relates to fibrosis developing during inflammatory diseases i.e. diseases related to acute or chronic inflammation (caused by tissue injury, pathogen infections or toxic agents) or as a consequence.

In some embodiments, the method of the present invention is particularly suitable for the treatment of hepatic fibrosis.

The term "monoacylglycerol lipase" or "MGL", also known as MAG lipase, MAGL, or MGLL is a protein that, in humans, is encoded by the MGLL gene. MAGL is a 33-kDa, membrane-associated member of the serine hydrolase superfamily and contains the classical GXSXG consensus sequence common to most serine hydrolases.

The term "MGL inhibitor" has its general meaning in the art and is intended to encompass a compound that interacts with monoacylglycerol lipase (MGL) to substantially reduce or eliminate its catalytic activity, thereby increasing the concentrations of its substrate(s).

MGL inhibitors are well known to the skilled person. For example the skilled person may easily identify such inhibitors from the following patent publications:

U.S. Pat. No. 8,349,842
U.S. Pat. No. 8,362,000
U.S. Pat. No. 8,362,001
U.S. Pat. No. 8,367,653
U.S. Pat. No. 8,367,697
U.S. Pat. No. 8,399,454
U.S. Pat. No. 8,415,341
U.S. Pat. No. 8,426,401
U.S. Pat. No. 8,435,977
U.S. Pat. No. 8,445,477
U.S. Pat. No. 8,450,303
U.S. Pat. No. 8,455,476
U.S. Pat. No. 8,513,423
U.S. Pat. No. 8,575,363
U.S. Pat. No. 8,604,017
U.S. Pat. No. 8,623,858
U.S. Pat. No. 8,637,498
U.S. Pat. No. 8,691,805
U.S. Pat. No. 8,697,683
U.S. Pat. No. 8,722,658
U.S. Pat. No. 8,741,887
U.S. Pat. No. 8,759,333
U.S. Pat. No. 8,759,533
WO2010124082
WO2010124086
WO2010124102
WO2010124112
WO2010124114
WO2010124116
WO2010124119
WO2010124121
WO2010124122
WO2012030907
WO2012044613
WO2012054716
WO2012054721
WO2013049289
and WO2013049293.

Other examples of MGL inhibitors are also described in:

Tuccinardi T, Granchi C, Rizzolio F, Caligiuri I, Battistello V, Toffoli G, Minutolo F, Macchia M, Martinelli A. Identification and characterization of a new reversible MGL inhibitor. Bioorg Med Chem. 2014 Jul. 1; 22(13): 3285-91.

Magrioti V, Naxakis G, Hadjipavlou-Litina D, Makriyannis A, Kokotos G. A novel monoacylglycerol lipase inhibitor with analgesic and anti-inflammatory activity. Bioorg Med Chem Lett. 2008 Oct. 15; 18(20):5424-7.

Pan B, Wang W, Long J Z, Sun D, Hillard C J, Cravatt B F, Liu Q S. Blockade of 2-arachidonoylglycerol hydrolysis by selective monoacylglycerol lipase inhibitor 4-nitrophenyl 4-(dibenzo[d][1,3]dioxol-5-yl(hydroxy)methyl)piperidine-1-carboxylate (JZL184) Enhances retrograde endocannabinoid signaling. J Pharmacol Exp Ther. 2009 November; 331(2):591-7.

Long J Z, Li W, Booker L, Burston J J, Kinsey S G, Schlosburg J E, Pavon F J, Serrano A M, Selley D E, Parsons L H, Lichtman A H, Cravatt B F (November 2008). "Selective blockade of 2-arachidonoylglycerol hydrolysis produces cannabinoid behavioral effects". Nat. Chem. Biol. 5 (1): 37-44.)

In some embodiments, the MGL inhibitor is MJN110 (2,5-dioxopyrrolidin-1-yl 4-(bis(4-chlorophenyl)methyl) piperazine-1-carboxylate):

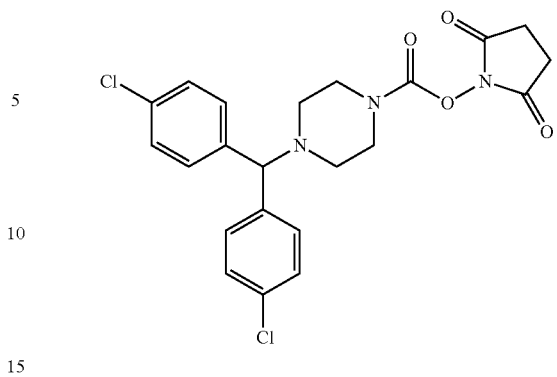

In some embodiments, the MGL inhibitor is JZL184 (4-nitrophenyl-4-[bis(1,3-benzodioxol-5-yl)(hydroxy) methyl]piperidine-1-carboxylate):

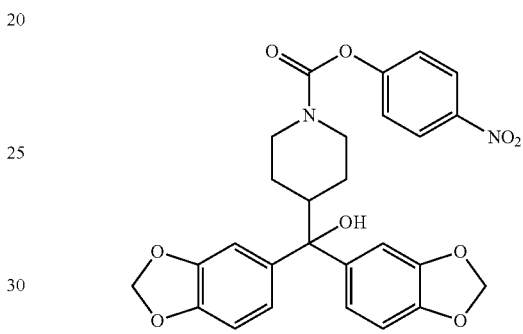

In some embodiments, the MGL inhibitor is a compound having the following formula:

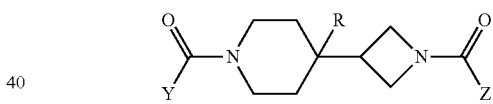

which is selected from the group consisting of the compound wherein Y is thiazol-4-yl, Z is biphenyl-4-yl, and R is H;

the compound wherein Y is thiazol-2-yl, Z is biphenyl-4-yl, and R is H;

the compound wherein Y is isothiazol-5-yl, Z is biphenyl-4-yl, and R is H;

the compound wherein Y is 1H-pyrrol-3-yl, Z is biphenyl-4-yl, and R is H;

the compound wherein Y is thiazol-5-yl, Z is biphenyl-4-yl, and R is H;

the compound wherein Y is phenyl, Z is 5-trifluoromethyl-benzothien-2-yl, and R is OH;

the compound wherein Y is thiazol-4-yl, Z is 3-chloro-6-fluoro-benzothien-2-yl, and R is H;

the compound wherein Y is thiazol-2-yl, Z is 3-chloro-6-fluoro-benzothien-2-yl, and R is H;

the compound wherein Y is thiazol-4-yl, Z is 2-fluoro-4-phenyl-phenyl, and R is H;

the compound wherein Y is thiazol-4-yl, Z is 4-(3-trifluoromethylphenyl)-phenyl, and R is H;

the compound wherein Y is thiazol-4-yl, Z is 3-(3-fluorophenyl)-phenyl, and R is H;

the compound wherein Y is thiazol-4-yl, Z is 4-(5-trifluoromethylthien-2-yl)-phenyl, and R is H;

the compound wherein Y is thiazol-4-yl, Z is 4-(3-trifluoromethylphenylmethyl)-phenyl, and R is H;
the compound wherein Y is thiazol-4-yl, Z is 3-methyl-6-trifluoromethyl-benzothien-2-yl, and R is H;
the compound wherein Y is thiazol-2-yl, Z is 2-fluoro-4-phenyl-phenyl, and R is H;
the compound wherein Y is thiazol-2-yl, Z is 4-(3-trifluoromethylphenyl)-phenyl, and R is H;
the compound wherein Y is thiazol-2-yl, Z is 3-(3-fluorophenyl)-phenyl, and R is H;
the compound wherein Y is thiazol-2-yl, Z is 4-(5-trifluoromethylthien-2-yl)-phenyl, and R is H;
the compound wherein Y is thiazol-2-yl, Z is 4-(3-trifluoromethylphenylmethyl)-phenyl, and R is H;
the compound wherein Y is thiazol-2-yl, Z is 3-methyl-6-trifluoromethyl-benzothien-2-yl, and R is H;
the compound wherein Y is 1H-pyrrol-2-yl, Z is 2-fluoro-4-phenyl-phenyl, and R is H;
the compound wherein Y is 1H-pyrrol-2-yl, Z is 4-(3-trifluoromethylphenyl)-phenyl, and R is H;
the compound wherein Y is 1H-pyrrol-2-yl, Z is 3-(3-fluorophenyl)-phenyl, and R is H;
the compound wherein Y is 1H-pyrrol-2-yl, Z is 4-(5-trifluoromethylthien-2-yl)-phenyl, and R is H;
the compound wherein Y is 1H-pyrrol-2-yl, Z is 4-(3-trifluoromethylphenylmethyl)-phenyl, and R is H;
the compound wherein Y is 1H-pyrrol-2-yl, Z is 3-methyl-6-trifluoromethyl-benzothien-2-yl, and R is H;
the compound wherein Y is thiazol-2-yl, Z is 4-(4-trifluoromethylphenylmethyl)-phenyl, and R is H;
the compound wherein Y is thiazol-2-yl, Z is 2-phenyl-benzoxazol-6-yl, and R is H;
the compound wherein Y is thiazol-2-yl, Z is 3-chloro-6-trifluoromethyl-benzothien-2-yl, and R is H;
the compound wherein Y is thiazol-2-yl, Z is 1-(4-fluorophenyl)-1H-indol-5-yl, and R is H;
the compound wherein Y is thiazol-2-yl, Z is 1-(4-trifluoromethylphenyl)-1H-indol-5-yl, and R is H;
the compound wherein Y is thiazol-2-yl, Z is 1-(3,4-difluorophenyl)-1H-indol-5-yl, and R is H;
the compound wherein Y is thiazol-4-yl, Z is 4-(4-trifluoromethylphenylmethyl)-phenyl, and R is H;
the compound wherein Y is thiazol-4-yl, Z is 2-phenyl-benzoxazol-6-yl, and R is H;
the compound wherein Y is thiazol-4-yl, Z is 3-chloro-6-trifluoromethyl-benzothien-2-yl, and R is H;
the compound wherein Y is thiazol-4-yl, Z is 1-(4-fluorophenyl)-1H-indol-5-yl, and R is H;
the compound wherein Y is thiazol-4-yl, Z is 1-(4-trifluoromethylphenyl)-1H-indol-5-yl, and R is H;
the compound wherein Y is thiazol-4-yl, Z is 1-(3,4-difluorophenyl)-1H-indol-5-yl, and R is H;
the compound wherein Y is 1H-pyrrol-2-yl, Z is 4-(4-trifluoromethylphenylmethyl)-phenyl, and R is H;
the compound wherein Y is 1H-pyrrol-2-yl, Z is 2-phenyl-benzoxazol-6-yl, and R is H;
the compound wherein Y is 1H-pyrrol-2-yl, Z is 3-chloro-6-trifluoromethyl-benzothien-2-yl, and R is H;
the compound wherein Y is 1H-pyrrol-2-yl, Z is 1-(4-fluorophenyl)-1H-indol-5-yl, and R is H;
the compound wherein Y is 1H-pyrrol-2-yl, Z is 1-(4-trifluoromethylphenyl)-1H-indol-5-yl, and R is H;
the compound wherein Y is 1H-pyrrol-2-yl, Z is 1-(3,4-difluorophenyl)-1H-indol-5-yl, and R is H;
the compound wherein Y is 2-fluoro-4-phenyl-phenyl, Z is thiazol-2-yl, and R is H;
the compound wherein Y is 2-fluoro-4-phenyl-phenyl, Z is thiazol-4-yl, and R is H;
the compound wherein Y is 1H-pyrrol-2-yl, Z is 2-fluoro-4-phenyl-phenyl, and R is H;
the compound wherein Y is 4-(3-trifluoromethylphenyl)-phenyl, Z is thiazol-2-yl, and R is H;
the compound wherein Y is 4-(3-trifluoromethylphenyl)-phenyl, Z is thiazol-4-yl, and R is H;
the compound wherein Y is 4-(3-trifluoromethylphenyl)-phenyl, Z is 1H-pyrrol-2-yl, and R is H;
the compound wherein Y is 3-(3-fluorophenyl)-phenyl, Z is thiazol-2-yl, and R is H;
the compound wherein Y is 3-(3-fluorophenyl)-phenyl, Z is thiazol-4-yl, and R is H;
the compound wherein Y is 3-(3-fluorophenyl)-phenyl, Z is 1H-pyrrol-2-yl, and R is H;
the compound wherein Y is 4-(5-trifluoromethyl-thien-2-yl)-phenyl, Z is thiazol-2-yl, and R is H;
the compound wherein Y is 4-(5-trifluoromethyl-thien-2-yl)-phenyl, Z is thiazol-4-yl, and R is H;
the compound wherein Y is 4-(5-trifluoromethyl-thien-2-yl)-phenyl, Z is 1H-pyrrol-2-yl, and R is H;
the compound wherein Y is 4-(3-trifluoromethylphenylmethyl)-phenyl, Z is thiazol-2-yl, and R is H;
the compound wherein Y is 4-(3-trifluoromethylphenylmethyl)-phenyl, Z is thiazol-4-yl, and R is H;
the compound wherein Y is 4-(3-trifluoromethylphenylmethyl)-phenyl, Z is 1H-pyrrol-2-yl, and R is H;
the compound wherein Y is 3-methyl-6-trifluoromethyl-benzothien-2-yl, Z is thiazol-2-yl, and R is H;
the compound wherein Y is 3-methyl-6-trifluoromethyl-benzothien-2-yl, Z is thiazol-4-yl, and R is H;
the compound wherein Y is 3-methyl-6-trifluoromethyl-benzothien-2-yl, Z is 1H-pyrrol-2-yl, and R is H;
the compound wherein Y is 4-(4-trifluoromethylphenylmethyl)-phenyl, Z is thiazol-2-yl, and R is H;
the compound wherein Y is 4-(4-trifluoromethylphenylmethyl)-phenyl, Z is thiazol-4-yl, and R is H;
the compound wherein Y is 4-(4-trifluoromethylphenylmethyl)-phenyl, Z is 1H-pyrrol-2-yl, and R is H;
the compound wherein Y is 2-phenyl-benzoxazol-6-yl, Z is thiazol-2-yl, and R is H;
the compound wherein Y is 2-phenyl-benzoxazol-6-yl, Z is thiazol-4-yl, and R is H;
the compound wherein Y is 2-phenyl-benzoxazol-6-yl, Z is 1H-pyrrol-2-yl, and R is H;
the compound wherein Y is 3-chloro-6-trifluoromethyl-benzothien-2-yl, Z is thiazol-2-yl, and R is H;
the compound wherein Y is 3-chloro-6-trifluoromethyl-benzothien-2-yl, Z is thiazol-4-yl, and R is H;
the compound wherein Y is 3-chloro-6-trifluoromethyl-benzothien-2-yl, Z is 1H-pyrrol-2-yl, and R is H;
the compound wherein Y is 1-(4-fluorophenyl)-1H-indol-5-yl, Z is thiazol-2-yl, and R is H;
the compound wherein Y is 1-(4-fluorophenyl)-1H-indol-5-yl, Z is thiazol-4-yl, and R is H;
the compound wherein Y is 1-(4-fluorophenyl)-1H-indol-5-yl, Z is 1H-pyrrol-2-yl, and R is H;
the compound wherein Y is 1-(4-trifluoromethylphenyl)-1H-indol-5-yl, Z is thiazol-2-yl, and R is H;
the compound wherein Y is 1-(4-trifluoromethylphenyl)-1H-indol-5-yl, Z is thiazol-4-yl, and R is H;
the compound wherein Y is 1-(4-trifluoromethylphenyl)-1H-indol-5-yl, Z is 1H-pyrrol-2-yl, and R is H;
the compound wherein Y is 1-(3,4-difluorophenyl)-1H-indol-5-yl, Z is thiazol-2-yl, and R is H;

the compound wherein Y is 1-(3,4-difluorophenyl)-1H-indol-5-yl, Z is thiazol-4-yl, and R is H;
the compound wherein Y is 1-(3,4-difluorophenyl)-1H-indol-5-yl, Z is 1H-pyrrol-2-yl, and R is H;
the compound wherein Y is thiazol-2-yl, Z is 1-(4-fluorophenyl)-1H-benzimidazol-5-yl, and R is H;
the compound wherein Y is thiazol-2-yl, Z is 1-(3,4-difluorophenyl)-1H-benzimidazol-5-yl, and R is H;
the compound wherein Y is thiazol-2-yl, Z is 1-(4-trifluoromethylphenyl)-1H-benzimidazol-5-yl, and R is H;
the compound wherein Y is thiazol-2-yl, Z is 1-(2,2,2-trifluoroethyl)-1H-benzimidazol-5-yl, and R is H;
the compound wherein Y is thiazol-2-yl, Z is 1-(3,3,3-trifluoropropyl)-1H-benzimidazol-5-yl, and R is H;
the compound wherein Y is thiazol-2-yl, Z is 1-phenyl-2-methyl-1H-benzimidazol-5-yl, and R is H;
the compound wherein Y is thiazol-2-yl, Z is 1-(4-fluorophenyl)-2-methyl-1H-benzimidazol-5-yl, and R is H;
the compound wherein Y is thiazol-2-yl, Z is 1-(3,4-difluorophenyl)-2-methyl-1H-benzimidazol-5-yl, and R is H;
the compound wherein Y is thiazol-2-yl, Z is 1-(4-trifluoromethylphenyl)-2-methyl-1H-benzimidazol-5-yl, and R is H;
the compound wherein Y is thiazol-2-yl, Z is 1-(2,2,2-trifluoroethyl)-2-methyl-1H-benzimidazol-5-yl, and R is H;
the compound wherein Y is thiazol-2-yl, Z is 1-(3,3,3-trifluoropropyl)-2-methyl-1H-benzimidazol-5-yl, and R is H;
the compound wherein Y is thiazol-2-yl, Z is 1-(4,4-difluorocyclohexyl)-2-methyl-1H-benzimidazol-5-yl, and R is H;
the compound wherein Y is thiazol-2-yl, Z is 1-(5-chloropyridin-2-yl)-1H-indol-5-yl, and R is H;
the compound wherein Y is thiazol-2-yl, Z is 6-trifluoromethyl-benzothien-2-yl, and R is OH;
the compound wherein Y is thiazol-2-yl, Z is 1-(2-methylpyridin-4-yl)-1H-indol-5-yl, and R is H;
the compound wherein Y is thiazol-2-yl, Z is 1-phenyl-1,3-dihydro-3H-benzimidazol-2-on-5-yl, and R is H;
the compound wherein Y is thiazol-2-yl, Z is 1-(4-fluorophenyl)-1,3-dihydro-3H-benzimidazol-2-on-5-yl, and R is H;
the compound wherein Y is thiazol-2-yl, Z is 1-(3,4-difluorophenyl)-1,3-dihydro-3H-benzimidazol-2-on-5-yl, and R is H;
the compound wherein Y is thiazol-2-yl, Z is 1-(4-trifluoromethylphenyl)-1,3-dihydro-3H-benzimidazol-2-on-5-yl, and R is H;
the compound wherein Y is thiazol-2-yl, Z is 1-(3,3,3-trifluoropropyl)-1,3-dihydro-3H-benzimidazol-2-on-5-yl, and R is H;
the compound wherein Y is thiazol-2-yl, Z is 1-(4,4-difluorocyclohexyl)-1,3-dihydro-3H-benzimidazol-2-on-5-yl, and R is H.

In some embodiments, the MGL inhibitor is a compound having the following formula:

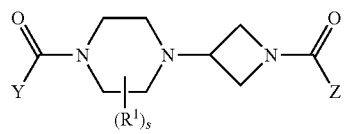

which is selected from the group consisting of:
a compound wherein Y is furan-2-yl, Z is 4-biphenyl, and s is 0;
a compound wherein Y is thiazol-4-yl, Z is 4-biphenyl, and s is 0;
a compound wherein Y is thiazol-5-yl, Z is 4-biphenyl, and s is 0;
a compound wherein Y is thiazol-2-yl, Z is 4-biphenyl, and s is 0;
a compound wherein Y is 2-methylthiazol-4-yl, Z is 4-biphenyl, and s is 0;
a compound wherein Y is 1-methyl-1H-pyrrol-2-yl, Z is 4-biphenyl, and s is 0;
a compound wherein Y is 5-bromofuran-2-yl, Z is 4-biphenyl, and s is 0;
a compound wherein Y is thien-2-yl, Z is 4-biphenyl, and s is 0;
a compound wherein Y is 5-methylthien-2-yl, Z is 4-biphenyl, and s is 0;
a compound wherein Y is 5-bromothien-2-yl, Z is 4-biphenyl, and s is 0;
a compound wherein Y is 5-chlorothien-2-yl, Z is 4-biphenyl, and s is 0;
a compound wherein Y is 3-bromothien-2-yl, Z is 4-biphenyl, and s is 0;
a compound wherein Y is 4-bromothien-2-yl, Z is 4-biphenyl, and s is 0;
a compound wherein Y is thieno[3,2-b]thiophen-2-yl, Z is 4-biphenyl, and s is 0;
a compound wherein Y is benzothien-2-yl, Z is 4-biphenyl, and s is 0;
a compound wherein Y is 3-methoxythien-2-yl, Z is 4-biphenyl, and s is 0;
a compound wherein Y is 4-biphenyl, Z is thiazol-2-yl, s is 1, and R1 is 3-phenyl;
a compound wherein Y is thiazol-2-yl, Z is 4-biphenyl, s is 1, and R1 is 2-methyl;
a compound wherein Y is thiazol-2-yl, Z is 4-biphenyl, s is 1, and R1 is 2-phenyl;
a compound wherein Y is thiazol-2-yl, Z is 3-biphenyl, s is 1, and R1 is 3-methyl;
a compound wherein Y is thiazol-2-yl, Z is 4-biphenyl, s is 1, and R1 is 3-methyl;
a compound wherein Y is thiazol-2-yl, Z is 2-phenyl-4-methylthien-5-yl, and s is 0;
a compound wherein Y is thiazol-2-yl, Z is 2-(thien-2-yl)-4-methylthien-5-yl, and s is 0;
a compound wherein Y is thiazol-2-yl, Z is 2-(4-methylphenyl)-4-methylthien-5-yl, and s is 0;
a compound wherein Y is thiazol-2-yl, Z is 2-(4-trifluoromethylphenyl)-4-methylthien-5-yl, and s is 0;
a compound wherein Y is thiazol-2-yl, Z is 3-(thien-2-yl)phenyl, and s is 0;
a compound wherein Y is thiazol-2-yl, Z is 4-(thien-2-yl)phenyl, and s is 0;
a compound wherein Y is thiazol-2-yl, Z is 3-(pyridin-2-yl)phenyl, and s is 0;
a compound wherein Y is thiazol-2-yl, Z is 3-(pyridin-3-yl)phenyl, and s is 0;
a compound wherein Y is thiazol-2-yl, Z is 3-(pyridin-4-yl)phenyl, and s is 0;
a compound wherein Y is thiazol-2-yl, Z is 4-(pyridin-3-yl)phenyl, and s is 0;
a compound wherein Y is thiazol-2-yl, Z is 3-(pyrimidin-5-yl)phenyl, and s is 0;
a compound wherein Y is thiazol-2-yl, Z is 4-(pyrimidin-5-yl)phenyl, and s is 0;

a compound wherein Y is thiazol-2-yl, Z is 3-(pyrimidin-2-yl)phenyl, and s is 0;
a compound wherein Y is thiazol-2-yl, Z is 4-(pyrimidin-2-yl)phenyl, and s is 0;
a compound wherein Y is thiazol-2-yl, Z is 4-(2-trifluoromethylphenyl)phenyl, and s is 0;
a compound wherein Y is thiazol-2-yl, Z is 3-(2-trifluoromethylphenyl)phenyl, and s is 0;
a compound wherein Y is thiazol-2-yl, Z is 3-(4-trifluoromethylphenyl)phenyl, and s is 0;
a compound wherein Y is thiazol-2-yl, Z is 4-(4-trifluoromethylphenyl)phenyl, and s is 0;
a compound wherein Y is thiazol-2-yl, Z is 3-(6-bromopyridin-2-yl)phenyl, and s is 0;
a compound wherein Y is thiazol-2-yl, Z is 3-(5-nitropyridin-2-yl)phenyl, and s is 0;
a compound wherein Y is thiazol-2-yl, Z is 4-(5-nitropyridin-2-yl)phenyl, and s is 0;
a compound wherein Y is thiazol-2-yl, Z is 5-(4-fluorophenyl)pyridin-2-yl, and s is 0;
a compound wherein Y is thiazol-2-yl, Z is 2-(4-fluorophenyl)-thiazol-4-yl, and s is 0;
a compound wherein Y is thiazol-2-yl, Z is 2-(3-fluorophenyl)-thiazol-4-yl, and s is 0;
a compound wherein Y is thiazol-2-yl, Z is 2-(2,4-dichlorophenyl)-thiazol-4-yl, and s is 0;
a compound wherein Y is thiazol-2-yl, Z is 2-(3,5-dichlorophenyl)-thiazol-4-yl, and s is 0;
a compound wherein Y is thiazol-2-yl, Z is 2-(4-methoxyphenyl)-thiazol-4-yl, and s is 0;
a compound wherein Y is thiazol-2-yl, Z is 2-phenyl-thiazol-4-yl, and s is 0;
a compound wherein Y is thiazol-2-yl, Z is 4-(3-cyanophenyl)phenyl, and s is 0;
a compound wherein Y is thiazol-2-yl, Z is 4-(3-chlorophenyl)phenyl, and s is 0;
a compound wherein Y is thiazol-2-yl, Z is 4-(4-chlorophenyl)phenyl, and s is 0;
a compound wherein Y is thiazol-2-yl, Z is 4-(3,5-dichlorophenyl)phenyl, and s is 0;
a compound wherein Y is thiazol-2-yl, Z is 5-phenyl-pyridin-3-yl, and s is 0;
a compound wherein Y is thiazol-2-yl, Z is 3-fluoro-4-phenyl-phenyl, and s is 0;
a compound wherein Y is thiazol-2-yl, Z is 4-(4-cyanophenyl)phenyl, and s is 0;
a compound wherein Y is thiazol-2-yl, Z is 4-(4-bromophenyl)phenyl, and s is 0;
a compound wherein Y is thiazol-4-yl, Z is 5-phenyl-pyridin-3-yl, and s is 0;
a compound wherein Y is thiazol-4-yl, Z is 3-fluoro-4-phenyl-phenyl, and s is 0;
a compound wherein Y is thiazol-4-yl, Z is 4-(4-cyanophenyl)phenyl, and s is 0;
a compound wherein Y is thiazol-4-yl, Z is 4-(4-bromophenyl)phenyl, and s is 0;
a compound wherein Y is thiazol-2-yl, Z is 4-(4-fluorophenyl)phenyl, and s is 0;
a compound wherein Y is thiazol-2-yl, Z is 4-(3,4-dichlorophenyl)phenyl, and s is 0;
a compound wherein Y is thiazol-2-yl, Z is 4-(3-methylphenyl)phenyl, and s is 0;
a compound wherein Y is thiazol-2-yl, Z is 4-(3-fluoro-6-methylphenyl)phenyl, and s is 0;
a compound wherein Y is thiazol-2-yl, Z is 4-(3-chloro-4-fluorophenyl)-phenyl, and s is 0;
a compound wherein Y is thiazol-2-yl, Z is 4-(2,4-difluorophenyl)phenyl, and s is 0;
a compound wherein Y is thiazol-2-yl, Z is 4-(3-methoxyphenyl)phenyl, and s is 0;
a compound wherein Y is thiazol-2-yl, Z is 4-(benzo[1,3]dioxal-5-yl)phenyl, and s is 0;
a compound wherein Y is thiazol-2-yl, Z is 4-(naphth-2-yl)phenyl, and s is 0;
a compound wherein Y is thiazol-2-yl, Z is 4-(3-nitrophenyl)phenyl, and s is 0;
a compound wherein Y is thiazol-2-yl, Z is 4-quinolin-5-yl-phenyl, and s is 0;
a compound wherein Y is thiazol-2-yl, Z is 4-(3-carboxyphenyl)phenyl, and s is 0;
a compound wherein Y is thiazol-2-yl, Z is 4-(3-cyanomethylphenyl)phenyl, and s is 0;
a compound wherein Y is thiazol-2-yl, Z is 4-(3-methylsulfonylphenyl)phenyl, and s is 0;
a compound wherein Y is thiazol-2-yl, Z is 4-(4-methylcarbonylphenyl)phenyl, and s is 0;
a compound wherein Y is thiazol-2-yl, Z is 4-(3-formylphenyl)phenyl, and s is 0;
a compound wherein Y is thiazol-2-yl, Z is 4-(4-hydroxyphenyl)phenyl, and s is 0;
a compound wherein Y is thiazol-2-yl, Z is 4-(4-chloro-3-trifluoromethylphenyl)phenyl, and s is 0;
a compound wherein Y is thiazol-2-yl, Z is 4-(4-dimethylaminosulfonylphenyl)phenyl, and s is 0;
a compound wherein Y is thiazol-2-yl, Z is 4-(4,5-difluoro-2-methoxyphenyl)phenyl, and s is 0;
a compound wherein Y is thiazol-2-yl, Z is 4-(4-nitrophenyl)phenyl, and s is 0;
a compound wherein Y is thiazol-2-yl, Z is 4-(3-formyl-4-methoxyphenyl)phenyl, and s is 0;
a compound wherein Y is thiazol-2-yl, Z is 4-(3-aminocarbonylphenyl)phenyl, and s is 0;
a compound wherein Y is thiazol-2-yl, Z is 4-(3-hydroxyphenyl)phenyl, and s is 0;
a compound wherein Y is thiazol-2-yl, Z is 4-(3-methylsulfonylamino-phenyl)phenyl, and s is 0;
a compound wherein Y is thiazol-2-yl, Z is 4-(3-t-butoxycarbonylamino-phenyl)phenyl, and s is 0;
a compound wherein Y is thiazol-2-yl, Z is 4-(3-isobutyloxyphenyl)phenyl, and s is 0;
a compound wherein Y is thiazol-2-yl, Z is 4-(3-(2-cyanoethyl)aminocarbonyl-phenyl)phenyl, and s is 0;
a compound wherein Y is thiazol-2-yl, Z is 4-(3-(2-cyanoethenyl)phenyl)phenyl, and s is 0;
a compound wherein Y is thiazol-2-yl, Z is 4-(4-(2-methoxycarbonylethenyl)phenyl)phenyl, and s is 0;
a compound wherein Y is thiazol-4-yl, Z is 4-(4-fluorophenyl)phenyl, and s is 0;
a compound wherein Y is thiazol-4-yl, Z is 4-(2,4-difluorophenyl)phenyl, and s is 0;
a compound wherein Y is thiazol-4-yl, Z is 4-(3-chloro-4-fluorophenyl)phenyl, and s is 0;
a compound wherein Y is thiazol-4-yl, Z is 4-(3,4-dichlorophenyl)phenyl, and s is 0;
a compound wherein Y is thiazol-4-yl, Z is 4-(3-trifluoromethylphenyl)phenyl, and s is 0;
a compound wherein Y is thiazol-2-yl, Z is 4-(3-aminophenyl)phenyl, and s is 0;
a compound wherein Y is thiazol-2-yl, Z is 4-(3-methylcarbonylamino-phenyl)phenyl, and s is 0;
a compound wherein Y is thiazol-4-yl, Z is 4-(3-methylcarbonylamino-phenyl)phenyl, and s is 0;

a compound wherein Y is thiazol-4-yl, Z is 4-(3-methanesulfonylphenyl)phenyl, and s is 0;

a compound wherein Y is thiazol-2-yl, Z is 4-(3-trifluoromethylphenyl)phenyl, and s is 0;

a compound wherein Y is thiazol-2-yl, Z is 2-methyl-4-(3-trifluoromethylphenyl)phenyl, and s is 0;

a compound wherein Y is thiazol-4-yl, Z is 2-methyl-4-(3-trifluoromethylphenyl)phenyl, and s is 0;

a compound wherein Y is thiazol-2-yl, Z is 3-methyl-(3-trifluoromethylphenyl)phenyl, and s is 0;

a compound wherein Y is thiazol-4-yl, Z is 3-methyl-4-(3-trifluoromethylphenyl)phenyl, and s is 0;

a compound wherein Y is thiazol-2-yl, Z is 2-fluoro-4-(3-trifluoromethylphenyl)phenyl, and s is 0;

a compound wherein Y is thiazol-4-yl, Z is 2-fluoro-4-(3-trifluoromethylphenyl)phenyl, and s is 0;

a compound wherein Y is thiazol-2-yl, Z is 3-methoxy-4-(3-trifluoromethylphenyl)phenyl, and s is 0;

a compound wherein Y is thiazol-4-yl, Z is 3-methoxy-4-(3-trifluoromethylphenyl)phenyl, and s is 0;

a compound wherein Y is thiazol-2-yl, Z is 2-chloro-4-(3-trifluoromethylphenyl)phenyl, and s is 0;

a compound wherein Y is thiazol-4-yl, Z is 2-chloro-4-(3-trifluoromethylphenyl)phenyl, and s is 0;

a compound wherein Y is thiazol-4-yl, Z is 2-methyl-4-(3-chloro-4-fluorophenyl)phenyl, and s is 0;

a compound wherein Y is thiazol-4-yl, Z is 2-methyl-4-(4-chloro-3-trifluoromethylphenyl)phenyl, and s is 0;

a compound wherein Y is thiazol-4-yl, Z is 3-methyl-4-(3-chloro-4-fluorophenyl)phenyl, and s is 0;

a compound wherein Y is thiazol-4-yl, Z is 3-methyl-4-(4-chloro-3-trifluoromethylphenyl)phenyl, and s is 0;

a compound wherein Y is thiazol-4-yl, Z is 3-methoxy-4-(3-chloro-4-fluorophenyl)phenyl, and s is 0;

a compound wherein Y is thiazol-4-yl, Z is 3-methoxy-4-(4-chloro-3-trifluoromethylphenyl)phenyl, and s is 0;

a compound wherein Y is thiazol-4-yl, Z is 2-chloro-4-(3-chloro-4-fluorophenyl)phenyl, and s is 0;

a compound wherein Y is thiazol-4-yl, Z is 2-chloro-4-(4-chloro-3-trifluoromethylphenyl)phenyl, and s is 0;

a compound wherein Y is thiazol-4-yl, Z is 5-(4-methylphenyl)-1H-pyrrol-2-yl, and s is 0;

a compound wherein Y is 4-fluorophenyl, Z is 4-biphenyl, and s is 0;

a compound wherein Y is 2-fluorophenyl, Z is 4-biphenyl, and s is 0;

a compound wherein Y is thien-3-yl, Z is 4-biphenyl, and s is 0;

a compound wherein Y is 1H-pyrrol-2-yl, Z is 4-biphenyl, and s is 0;

a compound wherein Y is cyclopropyl, Z is 4-biphenyl, and s is 0;

a compound wherein Y is 3-fluorophenyl, Z is 4-biphenyl, and s is 0;

a compound wherein Y is oxazol-2-yl, Z is 4-biphenyl, and s is 0;

a compound wherein Y is [1,2,3]thiadiazol-4-yl, Z is 4-biphenyl, and s is 0;

a compound wherein Y is isoxazol-5-yl, Z is 4-biphenyl, and s is 0;

a compound wherein Y is furazan-3-yl, Z is 4-biphenyl, and s is 0;

a compound wherein Y is 4-cyanothien-2-yl, Z is 4-biphenyl, and s is 0;

a compound wherein Y is isothiazol-5-yl, Z is 4-biphenyl, and s is 0;

a compound wherein Y is pyrrol-3-yl, Z is 4-biphenyl, and s is 0;

a compound wherein Y is 5-chlorofuran-2-yl, Z is 4-biphenyl, and s is 0;

a compound wherein Y is thiazol-2-yl, Z is 2-(4-trifluoromethylphenyl)-benzoxazol-6-yl, and s is 0;

a compound wherein Y is thiazol-2-yl, Z is 2-phenyl-benzoxazol-5-yl, and s is 0;

a compound wherein Y is thiazol-2-yl, Z is 2-phenyl-benzoxazol-6-yl, and s is 0;

a compound wherein Y is thiazol-2-yl, Z is 5-phenyl-naphth-2-yl, and s is 0;

a compound wherein Y is thiazol-2-yl, Z is 3-chloro-6-phenyl-benzothien-2-yl, and s is 0;

a compound wherein Y is thiazol-4-yl, Z is 3-chloro-6-phenyl-benzothien-2-yl, and s is 0;

a compound wherein Y is 2-methylcarbonylamino-thiazol-4-yl, Z is 4-biphenyl, and s is 0;

a compound wherein Y is thiazol-4-yl, Z is 2-(3-trifluoromethylphenyl)-4-methyl-thiazol-5-yl, and s is 0; 0 a compound wherein Y is thiazol-2-yl, Z is 1-(4-fluorophenyl)-indol-5-yl, and s is 0;

a compound wherein Y is thiazol-4-yl, Z is 2-methyl-4-phenyl-phenyl, and s is 0;

a compound wherein Y is thiazol-2-yl, Z is 2-(4-chlorophenyl)-4-methyl-thiazol-5-yl, and s is 0;

a compound wherein Y is thiazol-2-yl, Z is 2-(3-chlorophenyl)-4-methyl-thiazol-5-yl, and s is 0;

a compound wherein Y is thiazol-2-yl, Z is 1-phenyl-3-methyl-indol-5-yl, and s is 0;

a compound wherein Y is thiazol-4-yl, Z is 1-(3,4,5-trifluoro-phenyl)-indol-5-yl, and s is 0;

a compound wherein Y is thiazol-2-yl, Z is 1-(4-fluorophenyl)-1H-pyrrolo[2,3-b]pyridin-5-yl, and s is 0;

a compound wherein Y is cyclopropyl, Z is 4-(3-trifluoromethylphenyl)-phenyl, and s is 0;

a compound wherein Y is thiazol-4-yl, Z is 3-methyl-5-phenyl-benzothien-2-yl, and s is 0;

a compound wherein Y is thiazol-2-yl, Z is 4-(3-fluorophenyl)-5-methyl-thien-2-yl, and s is 0;

a compound wherein Y is thiazol-2-yl, Z is 1-methyl-7-(3-trifluoromethylphenyl)-indol-5-yl, and s is 0;

a compound wherein Y is 1H-pyrrol-2-yl, Z is 1-(2,4-difluorophenyl)-indol-5-yl, and s is 0;

a compound wherein Y is 1H-pyrrol-2-yl, Z is 1-(6-trifluoromethylpyridin-3-yl)-indol-5-yl, and s is 0;

a compound wherein Y is thiazol-2-yl, Z is 3-fluoro-6-(4-trifluoromethylphenyl)-benzothien-2-yl, and s is 0;

a compound wherein Y is thiazol-2-yl, Z is 1-(4-trifluoromethylphenyl)-1H-benzimidazol-5-yl, and s is 0;

a compound wherein Y is thiazol-2-yl, Z is 4-methyl-5-(3-fluorophenyl)-thien-2-yl, and s is 0;

a compound wherein Y is thiazol-2-yl, Z is 1-methyl-7-(3-fluorophenyl)-indol-5-yl, and s is 0;

a compound wherein Y is 4-(3-trifluoromethylphenyl)-phenyl, Z is thiazol-4-yl, and s is 0;

a compound wherein Y is thiazol-2-yl, Z is 1-(3-trifluoromethoxyphenyl)-3-methyl-indol-5-yl, and s is 0;

a compound wherein Y is thiazol-4-yl, Z is 1-(4-fluorophenyl)-6-fluoro-indol-5-yl, and s is 0;

a compound wherein Y is thinol-4-yl, Z is 3-fluoro-4-(3-trifluoromethylphenyl)-phenyl, and s is 0;

a compound wherein Y is thiazol-4-yl, Z is 4-(5-trifluoromethylthien-2-yl)-phenyl, and s is 0;

a compound wherein Y is thiazol-2-yl, Z is 1-(6-methoxypyridin-3-yl)-indol-5-yl, and s is 0;

a compound wherein Y is thiazol-2-yl, Z is 1-(5-methyl-pyridin-2-yl)-indol-5-yl, and s is 0;
a compound wherein Y is thiazol-2-yl, Z is (2-methyl-4-phenyl)phenyl, and s is 0;
a compound wherein Y is thiazol-2-yl, Z is 3-methyl-5-(4-fluorophenyl)-1H-indol-2-yl, and s is 0;
a compound wherein Y is thiazol-4-yl, Z is 1-(4-fluorophenyl)-7-methyl-indol-5-yl, and s is 0;
a compound wherein Y is thiazol-2-yl, Z is 2-(3,4-difluorophenyl)-benzoxazol-6-yl, and s is 0;
a compound wherein Y is 5-chloro-furan-2-yl, Z is 4-(3-trifluoromethylphenyl)-phenyl, and s is 0;
a compound wherein Y is trifluoromethyl, Z is 1-(4-fluorophenyl)-indol-5-yl, and s is 0;
a compound wherein Y is thiazol-2-yl, Z is 1-(4-trifluoromethylphenyl)-indazol-5-yl, and s is 0;
a compound wherein Y is thiazol-4-yl, Z is 1-(4-fluorophenyl)-2,3-dihydro-1H-indol-5-yl, and s is 0;
a compound wherein Y is thiazol-2-yl, Z is 4-(4-fluorophenyl)-thiazol-2-yl, and s is 0;
a compound wherein Y is thiazol-2-yl, Z is 5-(4-chlorophenyl)-1-(3,4-dichlorophenyl)-1H-pyrazol-3-yl, and s is 0;
a compound wherein Y is thiazol-4-yl, Z is 1-methyl-3-(3-trifluoromethylphenyl)-indol-6-yl, and s is 0;
a compound wherein Y is oxazol-2-yl, Z is 4-(3-trifluoromethylphenyl)-phenyl, and s is 0;
a compound wherein Y is thiazol-2-yl, Z is 4-(4-trifluoromethyl-phenyl)-quinazolin-7-yl, and s is 0;
a compound wherein Y is 4-bromothien-2-yl, Z is 4-(3-trifluoromethylphenyl)-phenyl, and s is 0;
a compound wherein Y is thiazol-2-yl, Z is 1-(4-fluorophenyl)-3-methyl-indol-5-yl, and s is 0;
a compound wherein Y is 1-(4-fluorophenyl)-3-methyl-indol-5-yl, Z is thiazol-2-yl, and s is 0;
a compound wherein Y is thiazol-2-yl, Z is 1-(4-fluorophenyl)-indazol-5-yl, and s is 0;
a compound wherein Y is thiazol-2-yl, Z is 3-(4-methoxyphenyl)-phenyl, and s is 0;
a compound wherein Y is thiazol-2-yl, Z is 3-fluoro-5-(4-trifluoromethylphenyl)-benzothien-2-yl, and s is 0;
a compound wherein Y is thiazol-2-yl, Z is 3-(3-trifluoromethylphenyl)-phenyl, and s is 0;
a compound wherein Y is oxazol-4-yl, Z is 4-(3-trifluoromethylphenyl)-phenyl, and s is 0;
a compound wherein Y is thiazol-2-yl, Z is 3-trifluoromethyl-6-phenyl-benzothien-2-yl, and s is 0;
a compound wherein Y is thiazol-2-yl, Z is 4-(4-fluorophenyl)-5-methyl-thien-2-yl, and s is 0;
a compound wherein Y is isothiazol-5-yl, Z is 1-(4-trifluoromethylphenyl)-indol-5-yl, and s is 0;
a compound wherein Y is thiazol-4-yl, Z is 3-trifluoromethyl-6-phenyl-benzothien-2-yl, and s is 0;
a compound wherein Y is 1H-pyrrol-2-yl, Z is 1-(4-fluorophenyl)-2,3-dihydro-1H-indol-5-yl, and s is 0;
a compound wherein Y is thiazol-2-yl, Z is 1-methyl-3-(3-trifluoromethylphenyl)-indol-6-yl, and s is 0;
a compound wherein Y is thiazol-2-yl, Z is 1-methyl-7-(4-fluorophenyl)-indol-6-yl, and s is 0;
a compound wherein Y is thiazol-4-yl, Z is 3-chloro-4-(3-trifluoromethylphenyl)-phenyl, and s is 0;
a compound wherein Y is thiazol-2-yl, Z is 5-(4-chlorophenyl)-1-(2,4-dichlorophenyl)-4-methyl-1H-pyrazol-3-yl, and s is 0;
a compound wherein Y is thiazol-2-yl, Z is 3-phenyl-5-fluoro-phenyl, and s is 0;
a compound wherein Y is thiazol-2-yl, Z is 1-(6-methyl-pyridin-3-yl)-indol-5-yl, and s is 0;
a compound wherein Y is thiazol-2-yl, Z is 1-(3,4-difluorophenyl)-indazol-5-yl, and s is 0;
a compound wherein Y is thiazol-2-yl, Z is 1-(2-methoxy-pyridin-4-yl)-indol-5-yl, and s is 0;
a compound wherein Y is thiazol-4-yl, Z is 2-fluoro-4-phenyl-phenyl, and s is 0;
a compound wherein Y is thiazol-2-yl, Z is 1-(2-cyanophenyl)-indol-5-yl, and s is 0;
a compound wherein Y is thiazol-2-yl, Z is 1-(3-fluorophenyl)-indazol-5-yl, and s is 0;
a compound wherein Y is thiazol-4-yl, Z is 1-(4-fluorophenyl)-7-fluoro-indol-5-yl, and s is 0;
a compound wherein Y is 2,2-difluoro-cyclopropyl, Z is 4-(3-trifluoromethylphenyl)phenyl, and s is 0;
a compound wherein Y is thiazol-2-yl, Z is 1-(3-cyanophenyl)-indol-5-yl, and s is 0;
a compound wherein Y is isothiazol-5-yl, Z is 3-methyl-4-(3-trifluoromethylphenyl)phenyl, and s is 0;
a compound wherein Y is thiazol-2-yl, Z is 1-(3-methoxy-4-cyanophenyl)-indol-5-yl, and s is 0;
a compound wherein Y is thiazol-2-yl, Z is 1-(3-chloro-5-trifluoromethylpyridin-2-yl)-indol-5-yl, and s is 0;
a compound wherein Y is thiazol-2-yl, Z is 3-(2,4-difluorophenyl)phenyl, and s is 0;
a compound wherein Y is isoxazol-5-yl, Z is 4-(3-trifluoromethylphenyl)phenyl, and s is 0;
a compound wherein Y is thiazol-2-yl, Z is 2,3-diphenyl-1H-indol-6-yl, and s is 0;
a compound wherein Y is 1H-pyrrol-2-yl, Z is 1-(4-trifluoromethylphenyl)-indol-5-yl, and s is 0;
a compound wherein Y is thiazol-2-yl, Z is 1-(5-fluoropyridin-2-yl)-indol-5-yl, and s is 0;
a compound wherein Y is thiazol-2-yl, Z is 5-phenyl-thien-2-yl, and s is 0;
a compound wherein Y is thiazol-2-yl, Z is 4-(3,5-difluorophenyl)-pyrazol-1-yl, and s is 0;
a compound wherein Y is thiazol-2-yl, Z is 3-(3-fluorophenyl)phenyl, and s is 0;
a compound wherein Y is thiazol-2-yl, Z is 2-phenyl-benzothiazol-6-yl, and s is 0;
a compound wherein Y is thiazol-2-yl, Z is 1-(6-methyl-pyridin-2-yl)-indol-5-yl, and s is 0;
a compound wherein Y is thiazol-2-yl, Z is 1-(pyridin-4-yl)-indol-5-yl, and s is 0;
a compound wherein Y is thiazol-2-yl, Z is 1-(4-methyl-pyridin-2-yl)-indol-5-yl, and s is 0;
a compound wherein Y is thiazol-4-yl, Z is 1-(3,4-difluorophenyl)-indazol-5-yl, and s is 0;
a compound wherein Y is thiazol-2-yl, Z is 4-phenyl-quinazolin-7-yl, and s is 0;
a compound wherein Y is thiazol-2-yl, Z is 2-(3-fluorophenyl)-benzothiazol-6-yl, and s is 0;
a compound wherein Y is thiazol-2-yl, Z is 1-methyl-3-phenyl-indol-6-yl, and s is 0;
a compound wherein Y is thiazol-4-yl, Z is 1-(4-cyanophenyl)-indol-5-yl, and s is 0;
a compound wherein Y is 1-(3,4-difluorophenyl)-3-methyl-indol-5-yl, Z is thiazol-2-yl, and s is 0;
a compound wherein Y is thiazol-2-yl, Z is 1-(pyridin-2-yl)-indol-5-yl, and s is 0;
a compound wherein Y is 4-(5-trifluoromethylthien-2-yl)-phenyl, Z is thiazol-4-yl, and s is 0;
a compound wherein Y is thiazol-2-yl, Z is 1-methyl-3-phenyl-indazol-5-yl, and s is 0;

a compound wherein Y is 1H-pyrrol-2-yl, Z is 4-(5-trifluoromethylthien-2-yl)phenyl, and s is 0;

a compound wherein Y is thiazol-4-yl, Z is 1-(2,4-difluorophenyl)-indol-5-yl, and s is 0;

a compound wherein Y is furan-3-yl, Z is biphenyl-4-yl, and s is 0;

a compound wherein Y is thiazol-4-yl, Z is 2-phenyl-benzoxazol-6-yl, and s is 0;

a compound wherein Y is thiazol-2-yl, Z is 1-methyl-3-(3-fluorophenyl)-indol-6-yl, and s is 0;

a compound wherein Y is 5-chloro-thien-2-yl, Z is 4-(3-trifluoromethylphenyl)phenyl, and s is 0;

a compound wherein Y is thiazol-2-yl, Z is 3-phenyl-5-trifluoromethyl-phenyl, and s is 0;

a compound wherein Y is isoxazol-3-yl, Z is 4-(3-trifluoromethylphenyl)-phenyl, and s is 0;

a compound wherein Y is thiazol-2-yl, Z is 1-(3-trifluoromethylphenyl)-3-methyl-1H-thieno[2,3-c]pyrazol-5-yl, and s is 0;

a compound wherein Y is thiazol-2-yl, Z is 1-(5-fluoro-pyrimidin-2-yl)-indol-5-yl, and s is 0;

a compound wherein Y is thiazol-4-yl, Z is 1-methyl-3-(4-trifluoromethylphenyl)-indol-6-yl, and s is 0;

a compound wherein Y is thiazol-2-yl, Z is 3-methyl-5-(2-fluoropyridin-3-yl)-1H-indol-2-yl, and s is 0;

a compound wherein Y is thiazol-2-yl, Z is 4-methyl-(2-(4-fluorophenyl)-thiazol-5-yl, and s is 0;

a compound wherein Y is thiazol-4-yl, Z is 2-(3-trifluoromethylphenyl)-benzoxazol-6-yl, and s is 0;

a compound wherein Y is thiazol-4-yl, Z is 1-phenyl-3-methyl-indol-5-yl, and s is 0;

a compound wherein Y is thiazol-2-yl, Z is 1-(4-fluorophenyl)-1H-pyrrolo[3,2-b]pyridin-5-yl, and s is 0;

a compound wherein Y is thiazol-2-yl, Z is 2-phenyl-benxoxazol-7-yl, and s is 0;

a compound wherein Y is thiazol-4-yl, Z is 1-methyl-3-phenyl-indol-6-yl, and s is 0;

a compound wherein Y is thiazol-2-yl, Z is 4-(5-(4-methylphenyl)-[1,3,4]oxadiazol-2-yl)-phenyl, and s is 0;

a compound wherein Y is thiazol-2-yl, Z is 4-(4-fluorophenyl)-thien-2-yl, and s is 0;

a compound wherein Y is thiazol-2-yl, Z is 2-(3-trifluoromethylphenyl)-benzoxazol-6-yl, and s is 0;

a compound wherein Y is thiazol-2-yl, Z is 1-(4-cyanophenyl)-indol-5-yl, and s is 0;

a compound wherein Y is thiazol-2-yl, Z is 4-(3-fluorophenyl)-thien-2-yl, and s is 0;

a compound wherein Y is 4-(5-trifluoromethylthien-2-yl)-phenyl, Z is thiazol-2-yl, and s is 0;

a compound wherein Y is 4-(5-trifluoromethylthien-2-yl)-phenyl, Z is 1H-pyrrol-2-yl, and s is 0;

a compound wherein Y is thiazol-4-yl, Z is 1-phenyl-indazol-5-yl, and s is 0;

a compound wherein Y is thiazol-2-yl, Z is 1,5-diphenyl-pyrazol-3-yl, and s is 0;

a compound wherein Y is thiazol-2-yl, Z is 2-(pyridin-2-yl)-benzothiazol-6-yl, and s is 0;

a compound wherein Y is 4-(3-trifluoromethylphenyl)-phenyl, Z is 1H-pyrrol-2-yl, and s is 0;

a compound wherein Y is thiazol-2-yl, Z is 1-(4-fluorophenyl)-benzimidazol-5-yl, and s is 0;

a compound wherein Y is thiazol-2-yl, Z is 3-phenyl-4-methoxy-phenyl, and s is 0;

a compound wherein Y is oxazol-5-yl, Z is 4-(3-trifluoromethylphenyl)-phenyl, and s is 0;

a compound wherein Y is thiazol-2-yl, Z is 1-methyl-3-(3-fluorophenyl)-indazol-5-yl, and s is 0;

a compound wherein Y is thiazol-2-yl, Z is 1-(4-aminocarbonylphenyl)-indol-5-yl, and s is 0;

a compound wherein Y is thiazol-2-yl, Z is 2-fluoro-3-phenyl-phenyl, and s is 0;

a compound wherein Y is thiazol-2-yl, Z is 2-(2-chlorophenyl)-benzoxazol-4-yl, and s is 0;

a compound wherein Y is thiazol-2-yl, Z is 1-(pyrimidin-2-yl)-indol-5-yl, and s is 0;

a compound wherein Y is thiazol-2-yl, Z is 3-methyl-5-(5-methoxypyridin-3-yl)-1H-indol-2-yl, and s is 0;

a compound wherein Y is 1H-pyrrol-2-yl, Z is 1-(6-methoxypyridin-3-yl)-indol-5-yl, and s is 0;

a compound wherein Y is thiazol-2-yl, Z is 1-(3-aminocarbonylphenyl)-indol-5-yl, and s is 0;

a compound wherein Y is thiazol-4-yl, Z is 2-(3,4-difluorophenyl)-benzoxazol-6-yl, and s is 0;

a compound wherein Y is thiazol-2-yl, Z is 4,5-diphenyl-1H-imidazol-2-yl, and s is 0;

a compound wherein Y is thiazol-4-yl, Z is 1-(5-chloropyridin-2-yl)-indol-5-yl, and s is 0;

a compound wherein Y is 1H-pyrrol-2-yl, Z is 1-(6-methylpyridin-3-yl)-indol-5-yl, and s is 0;

a compound wherein Y is thiazol-4-yl, Z is 1-(2-cyanophenyl)-indol-5-yl, and s is 0;

a compound wherein Y is thiazol-2-yl, Z is 7-(3-fluorophenyl)-1H-indol-5-yl, and s is 0;

a compound wherein Y is trifluoromethyl, Z is 1-(5-methylpyridin-2-yl)-indol-5-yl, and s is 0;

a compound wherein Y is thiazol-4-yl, Z is 3-(2-trifluoromethylphenyl)-phenyl, and s is 0;

a compound wherein Y is thiazol-2-yl, Z is 1-(3,4-difluorophenyl)-benzimidazol-5-yl, and s is 0;

a compound wherein Y is thiazol-4-yl, Z is 2-phenyl-benzothiazol-6-yl, and s is 0;

a compound wherein Y is thiazol-4-yl, Z is 3-(3-trifluoromethylphenyl)-phenyl, and s is 0;

a compound wherein Y is 1H-pyrrol-2-yl, Z is 1-(pyridin-2-yl)-indol-5-yl, and s is 0;

a compound wherein Y is thiazol-2-yl, Z is 2-phenyl-benzoxazol-6-yl, and s is 0;

a compound wherein Y is thiazol-2-yl, Z is 2-(3-chlorophenyl)-benzoxazol-4-yl, and s is 0;

a compound wherein Y is thiazol-2-yl, Z is 1-(pyridin-3-yl)-indol-5-yl, and s is 0;

a compound wherein Y is thiazol-2-yl, Z is 2-(2-fluorophenyl)-benzoxazol-4-yl, and s is 0;

a compound wherein Y is thiazol-2-yl, Z is 2-phenyl-1H-benzimidazol-5-yl, and s is 0;

a compound wherein Y is thiazol-2-yl, Z is 1-methyl-3-(4-fluorophenyl)-indazol-5-yl, and s is 0;

a compound wherein Y is thiazol-2-yl, Z is 6-(5-methoxy-pyridin-3-yl)-1H-indol-2-yl, and s is 0;

a compound wherein Y is thiazol-4-yl, Z is 1-(4-methyl-pyridin-2-yl)-indol-5-yl, and s is 0;

a compound wherein Y is thiazol-4-yl, Z is 5-(4-chlorophenyl)-1-(2,4-dichlorophenyl)-4-methyl-1H-pyrazol-3-yl, and s is 0;

a compound wherein Y is trifluoromethyl, Z is 1-(4-methyl-pyridin-2-yl)-indol-5-yl, and s is 0;

a compound wherein Y is thiazol-2-yl, Z is 2-chloro-5-phenyl-phenyl, and s is 0;

a compound wherein Y is thiazol-4-yl, Z is 1-(pyrimidin-2-yl)-indol-5-yl, and s is 0;

a compound wherein Y is thiazol-2-yl, Z is 2-(2-fluorophenyl)-4-methyl-thiazol-5-yl, and s is 0;

a compound wherein Y is thiazol-2-yl, Z is 1-(4-fluorophenyl)-3-methyl-1H-pyrazolo[3,4-b]pyridin-5-yl, and s is 0;
a compound wherein Y is thiazol-2-yl, Z is 6-(4-fluorophenyl)-1H-indol-2-yl, and s is 0;
a compound wherein Y is thiazol-2-yl, Z is 3-methyl-5-(2-methyl-2H-pyrazol-3-yl)-1H-indol-2-yl, and s is 0;
a compound wherein Y is thiazol-2-yl, Z is 1-(3,4-difluorophenyl)-2-methyl-benzimidazol-5-yl, and s is 0;
a compound wherein Y is thiazol-2-yl, Z is 1-phenyl-benzimidazol-5-yl, and s is 0;
a compound wherein Y is thiazol-2-yl, Z is 2-fluoro-5-phenyl-phenyl, and s is 0;
a compound wherein Y is thiazol-2-yl, Z is 5-phenyl-furo[2,3-b]pyridin-2-yl, and s is 0;
a compound wherein Y is thiazol-2-yl, Z is 2-(thiazol-2-yl)-benzothiazol-6-yl, and s is 0;
a compound wherein Y is thiazol-2-yl, Z is 6-(3,5-dimethyl-isoxazol-4-yl)-1H-indol-2-yl, and s is 0;
a compound wherein Y is 2-methyl-4-(3-trifluoromethylphenyl)-phenyl, Z is thiazol-4-yl, and s is 0;
a compound wherein Y is thiazol-2-yl, Z is 5-(4-fluorophenyl)-furo[2,3-b]pyridin-2-yl, and s is 0;
a compound wherein Y is thiazol-2-yl, Z is 5-methyl-2-(4-methylphenyl)-2H-[1,2,3]triazol-4-yl, and s is 0;
a compound wherein Y is thiazol-2-yl, Z is 1-(4-trifluoromethylphenyl)-2-methyl-benzimidazol-5-yl, and s is 0;
a compound wherein Y is thiazol-2-yl, Z is 1-(2-methyl-pyrimidin-4-yl)-indol-5-yl, and s is 0;
a compound wherein Y is 2-methyl-thiazol-4-yl, Z is 4-(3-trifluoromethylphenyl)-phenyl, and s is 0;
a compound wherein Y is thiazol-2-yl, Z is 5-methyl-2-(4-chlorophenyl)-2H-[1,2,3]triazol-4-yl, and s is 0;
a compound wherein Y is 1-(3,4-difluorophenyl)-3-methyl-indol-5-yl, Z is 1H-pyrrol-2-yl, and s is 0;
a compound wherein Y is thiazol-2-yl, Z is 2-(4-chlorophenyl)-benzoxazol-4-yl, and s is 0;
a compound wherein Y is thiazol-4-yl, Z is 2-chloro-4-phenyl-phenyl, and s is 0;
a compound wherein Y is oxazol-4-yl, Z is biphenyl-4-yl, and s is 0;
a compound wherein Y is thiazol-2-yl, Z is 4-(benzimidazol-1-yl)-phenyl, and s is 0;
a compound wherein Y is thiazol-2-yl, Z is 1-(4-fluorophenyl)-indol-3-yl, and s is 0;
a compound wherein Y is thiazol-2-yl, Z is 1-(3,4-dichlorophenyl)-3,5-dimethyl-1H-pyrazol-4-yl, and s is 0;
a compound wherein Y is thiazol-2-yl, Z is 1-(3-fluorophenyl)-indol-3-yl, and s is 0;
a compound wherein Y is thiazol-2-yl, Z is 1-(4-fluorophenyl)-2-methyl-benzimidazol-5-yl, and s is 0;
a compound wherein Y is thiazol-4-yl, Z is 3-(3-fluorophenyl)-phenyl, and s is 0;
a compound wherein Y is thiazol-2-yl, Z is 1-phenyl-2-methyl-benzimidazol-5-yl, and s is 0;
a compound wherein Y is thiazol-4-yl, Z is 1-(4-fluorophenyl)-3-methyl-indol-5-yl, and s is 0;
a compound wherein Y is thiazol-4-yl, Z is 1-(4-trifluoromethylphenyl)-benzimidazol-5-yl, and s is 0;
a compound wherein Y is cyclobutyl, Z is biphenyl-4-yl, and s is 0;
a compound wherein Y is 2-phenyl-benzoxazol-6-yl, Z is thiazol-2-yl, and s is 0;
a compound wherein Y is thiazol-2-yl, Z is 2-methyl-3-phenyl-phenyl, and s is 0;
a compound wherein Y is biphenyl-4-yl, Z is isothiazol-5-yl, and s is 0;
a compound wherein Y is biphenyl-4-yl, Z is thiazol-2-yl, and s is 0;
a compound wherein Y is thiazol-4-yl, Z is 2-phenyl-benzoxazol-7-yl, and s is 0;
a compound wherein Y is thiazol-4-yl, Z is 2-(3-chlorophenyl)-benzoxazol-7-yl, and s is 0;
a compound wherein Y is thiazol-4-yl, Z is 3-(2,4-difluorophenyl)-phenyl, and s is 0;
a compound wherein Y is thiazol-4-yl, Z is 2-fluoro-3-phenyl-phenyl, and s is 0;
a compound wherein Y is thiazol-2-yl, Z is 6-(2-methyl-2H-pyrazol-3-yl)-1H-indol-2-yl, and s is 0;
a compound wherein Y is biphenyl-4-yl, Z is 3-fluorophenyl, and s is 0;
a compound wherein Y is 4-(3-trifluoromethylphenyl)-phenyl, Z is 1H-pyrrol-3-yl, and s is 0;
a compound wherein Y is thiazol-2-yl, Z is 6-(2-fluoropyridin-3-yl)-1H-indol-2-yl, and s is 0;
a compound wherein Y is thiazol-2-yl, Z is 4-(5-(4-methylphenyl)-[1,2,3]triazol-1-yl)-phenyl, and s is 0;
a compound wherein Y is biphenyl-4-yl, Z is thiazol-4-yl, and s is 0;
a compound wherein Y is 1H-pyrrol-2-yl, Z is 1-(pyridin-3-yl)-indol-5-yl, and s is 0;
a compound wherein Y is thiazol-4-yl, Z is 1-(5-fluoropyrimidin-2-yl)-indol-5-yl, and s is 0;
a compound wherein Y is thiazol-2-yl, Z is 4-(3-trifluoromethylpyrazol-1-yl)-phenyl, and s is 0;
a compound wherein Y is thiazol-4-yl, Z is 3-(4-methoxyphenyl)-phenyl, and s is 0;
a compound wherein Y is thiazol-2-yl, Z is 2-(pyridin-3-yl)-benzoxazol-4-yl, and s is 0;
a compound wherein Y is thiazol-2-yl, Z is 2-(furan-2-yl)-3H-benzimidazol-4-yl, and s is 0;
a compound wherein Y is thiazol-4-yl, Z is 3-methoxy-4-phenyl-phenyl, and s is 0;
a compound wherein Y is thiazol-4-yl, Z is 2-(3-fluorophenyl)-benzoxazol-7-yl, and s is 0;
a compound wherein Y is thiazol-2-yl, Z is 2-phenyl-3H-benzimidazol-4-yl, and s is 0;
a compound wherein Y is 2,2-difluoro-cyclopropyl, Z is biphenyl-4-yl, and s is 0;
a compound wherein Y is thiazol-4-yl, Z is 2-(4-fluorophenyl)-benzoxazol-4-yl, and s is 0;
a compound wherein Y is 4-(3-trifluoromethylphenyl)-phenyl, Z is oxazol-4-yl, and s is 0;
a compound wherein Y is thiazol-4-yl, Z is 3-phenyl-5-trifluoromethyl-phenyl, and s is 0;
a compound wherein Y is 2-methyl-4-(3-trifluoromethylphenyl)-phenyl, Z is thiazol-2-yl, and s is 0;
a compound wherein Y is thiazol-4-yl, Z is 1,5-diphenyl-1H-pyrazol-3-yl, and s is 0;
a compound wherein Y is isoxazol-3-yl, Z is biphenyl-4-yl, and s is 0;
a compound wherein Y is thiazol-2-yl, Z is 1-pyrimidin-5-yl-indol-5-yl, and s is 0;
a compound wherein Y is thiazol-4-yl, Z is 1-(3,4-difluorophenyl)-2-methyl-benzimidazol-5-yl, and s is 0;
a compound wherein Y is thiazol-4-yl, Z is 4-methoxy-3-phenyl-phenyl, and s is 0;
a compound wherein Y is biphenyl-4-yl, Z is thiazol-2-yl, s is 1, and R1 is 3-phenylmethyl;
a compound wherein Y is thiazol-2-yl, Z is 1-(2,4-dichlorophenyl)-4,5,6,7-tetrahydro-1H-indazol-3-yl, and s is 0;

a compound wherein Y is thiazol-5-yl, Z is 4-(5-trifluoromethylthien-2-yl)-phenyl, and s is 0;

a compound wherein Y is 1H-[1,2,3]triazol-4-yl, Z is biphenyl-4-yl, and s is 0;

a compound wherein Y is thiazol-4-yl, Z is 1-(3,4-difluorophenyl)-benzimidazol-5-yl, and s is 0;

a compound wherein Y is 2-phenyl-1H-benzimidazol-5-yl, Z is thiazol-2-yl, and s is 0;

a compound wherein Y is thiazol-2-yl, Z is 2-(pyridin-4-yl)-4-methyl-thiazol-5-yl, and s is 0;

a compound wherein Y is thiazol-4-yl, Z is 3-fluoro-5-phenyl-phenyl, and s is 0;

a compound wherein Y is thiazol-4-yl, Z is 1-(4-fluorophenyl)-benzimidazol-5-yl, and s is 0;

a compound wherein Y is 2-phenyl-benzoxazol-6-yl, Z is thiazol-4-yl, and s is 0;

a compound wherein Y is biphenyl-4-yl, Z is [1,2,3]thiadiazol-4-yl, and s is 0;

a compound wherein Y is thiazol-2-yl, Z is 1-(4-fluorophenyl)-1H-pyrrolo[3,2-b]pyridin-6-yl, and s is 0;

a compound wherein Y is thiazol-4-yl, Z is 3-(4-trifluoromethylphenyl)-phenyl, and s is 0;

a compound wherein Y is thiazol-4-yl, Z is 1-(3-fluorophenyl)-indol-3-yl, and s is 0;

a compound wherein Y is thiazol-4-yl, Z is 2-fluoro-5-phenyl-phenyl, and s is 0;

a compound wherein Y is thiazol-4-yl, Z is 1-phenyl-benzimidazol-5-yl, and s is 0;

a compound wherein Y is thiazol-4-yl, Z is 2-(4-fluorophenyl)-benzoxazol-7-yl, and s is 0;

a compound wherein Y is biphenyl-4-yl, Z is oxazol-2-yl, and s is 0;

a compound wherein Y is biphenyl-4-yl, Z is thiazol-4-yl, s is 1, and R1 is 3-phenylmethyl;

a compound wherein Y is thiazol-4-yl, Z is 2-methyl-3-phenyl-phenyl, and s is 0;

a compound wherein Y is biphenyl-4-yl, Z is thiazol-4-yl, s is 1, and R1 is 2-spirofused cyclopropyl;

a compound wherein Y is thiazol-4-yl, Z is 2-(2-fluorophenyl)-4-methyl-thiazol-5-yl, and s is 0;

a compound wherein Y is thiazol-4-yl, Z is 2-chloro-5-phenyl-phenyl, and s is 0;

a compound wherein Y is thiazol-4-yl, Z is 1-(4-trifluoromethylphenyl)-2-methyl-benzimidazol-5-yl, and s is 0;

a compound wherein Y is thiazol-4-yl, Z is 2-(4-chlorophenyl)-1H-benzimidazol-4-yl, and s is 0;

a compound wherein Y is thiazol-4-yl, Z is 1-(4-fluorophenyl)-2-methyl-benzimidazol-5-yl, and s is 0;

a compound wherein Y is biphenyl-4-yl, Z is 1H-pyrrol-3-yl, and s is 0;

a compound wherein Y is thiazol-4-yl, Z is 4-benzimidazol-1-yl-phenyl, and s is 0;

a compound wherein Y is thiazol-2-yl, Z is 5-(4-fluorophenyl)-1H-benzimidazol-2-yl, and s is 0;

a compound wherein Y is thiazol-4-yl, Z is 1-(4-fluorophenyl)-indol-3-yl, and s is 0;

a compound wherein Y is thiazol-4-yl, Z is 1-phenyl-2-methyl-benzimidazol-5-yl, and s is 0;

a compound wherein Y is thiazol-2-yl, Z is 1,5-diphenyl-pyrazol-4-yl, and s is 0;

a compound wherein Y is 4-benzimidazol-1-yl-phenyl, Z is thiazol-2-yl, and s is 0;

a compound wherein Y is thiazol-4-yl, Z is 2-phenyl-1H-benzimidazol-5-yl, and s is 0;

a compound wherein Y is thiazol-2-yl, Z is 2-phenyl-[1,2,3]triazol-4-yl, and s is 0;

a compound wherein Y is thiazol-2-yl, Z is 1-(4-fluorophenyl)-3,5-dimethyl-1H-pyrazol-4-yl, and s is 0;

a compound wherein Y is thiazol-4-yl, Z is 4-(3-trifluoromethylpyrazol-1-yl)-phenyl, and s is 0;

a compound wherein Y is thiazol-2-yl, Z is 5-(4-trifluoromethoxyphenyl)-1H-benzimidazol-2-yl, and s is 0;

a compound wherein Y is thiazol-4-yl, Z is 1-(2,4-dichlorophenyl)-4,5,6,7-tetrahydro-1H-indazol-3-yi, and s is 0;

a compound wherein Y is 4-benzimidazol-1-yl-phenyl, Z is thiazol-4-yl, and s is 0;

a compound wherein Y is thiazol-2-yl, Z is biphenyl-4-yl, s is 1, and R1 is 2(R,S)-trifluoromethyl, a compound wherein Y is thiazol-2-yl, Z is 5-(4-chlorophenyl)-1H-pyrrol-2-yl, and s is 0;

a compound wherein Y is 1H-indol-3-yl, Z is biphenyl-4-yl, and s is 0;

a compound wherein Y is 1H-pyrrol-2-yl, Z is 1-(2,4-dichlorophenyl)-4,5,6,7-tetrahydro-1H-indazol-3-yl, and s is 0;

a compound wherein Y is 1H-pyrazol-4-yl, Z is biphenyl-4-yl, and s is 0;

a compound wherein Y is trifluoromethyl, Z is 1-(2,4-dichlorophenyl)-4,5,6,7-tetrahydro-1H-indazol-3-yl, and s is 0;

a compound wherein Y is thiazol-2-yl, Z is 1-(6-trifluoromethylpyridin-3-yl)-indol-5-yl, and s is 0;

a compound wherein Y is thiazol-2-yl, Z is 1-(5-chloropyridin-2-yl)-indol-5-yl, and s is 0 a compound wherein Y is thiazol-2-yl, Z is 1-(5-trifluoromethylpyridin-2-yl)-indol-5-yl, and s is 0;

a compound wherein Y is thiazol-2-yl, Z is 3-fluoro-5-phenyl-benzothien-2-yl, and s is 0;

a compound wherein Y is thiazol-2-yl, Z is 3-phenyl-1H-indol-6-yl, and s is 0;

a compound wherein Y is thiazol-2-yl, Z is 3-(4-fluorophenyl)-1H-indol-6-yl, and s is 0;

a compound wherein Y is thiazol-2-yl, Z is 1-methyl-3-(4-fluorophenyl)-indol-6-yl, and s is 0;

a compound wherein Y is thiazol-2-yl, Z is 3-(3-fluorophenyl)-1H-indol-6-yl, and s is 0;

a compound wherein Y is thiazol-2-yl, Z is 1-(4-fluorophenyl)-indol-4-yl, and s is 0;

a compound wherein Y is thiazol-2-yl, Z is 4-(3-trifluoromethylphenyl)-thien-2-yl, and s is 0;

a compound wherein Y is thiazol-2-yl, Z is 3-methyl-4-phenyl-phenyl, and s is 0;

a compound wherein Y is thiazol-2-yl, Z is 2-chloro-4-phenyl-phenyl, and s is 0;

a compound wherein Y is 1H-pyrrol-3-yl, Z is 4-(3-trifluoromethylphenyl)-phenyl, and s is 0;

a compound wherein Y is 1H-pyrrol-2-yl, Z is 4-(3-trifluoromethylphenyl)-phenyl, and s is 0;

a compound wherein Y is thiazol-2-yl, Z is 4-(4-phenyl-thiazol-2-yl)-phenyl, and s is 0;

a compound wherein Y is thiazol-2-yl, Z is 4-(3-(4-chlorophenyl)-4,5,6,7-tetrahydroindazol-2-yl)-phenyl, and s is 0;

a compound wherein Y is thiazol-2-yl, Z is 4-(4-(2-chlorophenyl)-thiazol-2-yl)-phenyl, and s is 0;

a compound wherein Y is thiazol-2-yl, Z is 4-(4-(2,4-dichlorophenyl)-thiazol-2-yl)-phenyl, and s is 0;

a compound wherein Y is thiazol-2-yl, Z is 4-(3-(3-trifluoromethylphenyl)-5,6-dihydro-4H-cyclopentapyrazol-2-yl)-phenyl, and s is 0;

a compound wherein Y is thiazol-2-yl, Z is 4-(4-(3,4-dichlorophenyl)-thiazol-2-yl)-phenyl, and s is 0;

a compound wherein Y is thiazol-2-yl, Z is 4-(4-(3-trifluoromethylphenyl)-thiazol-2-yl)-phenyl, and s is 0;
a compound wherein Y is thiazol-2-yl, Z is 2-phenyl-1H-indol-6-yl, and s is 0;
a compound wherein Y is thiazol-2-yl, Z is 4-(4-(4-chlorophenyl)-pyrazol-1-yl)-phenyl, and s is 0;
a compound wherein Y is 5-bromofuran-2-yl, Z is 4-(3-trifluoromethylphenyl)-phenyl, and s is 0;
a compound wherein Y is 5-fluoro-thien-2-yl, Z is 4-(3-trifluoromethylphenyl)-phenyl, and s is 0;
a compound wherein Y is 1-(4-trifluoromethylphenyl)-indol-5-yl, Z is thiazol-4-yl, and s is 0;
a compound wherein Y is 1-(4-trifluoromethylphenyl)-indol-5-yl, Z is thiazol-2-yl, and s is 0;
a compound wherein Y is 1-(4-trifluoromethylphenyl)-indol-5-yl, Z is 1H-pyrrol-2-yl, and s is 0;
a compound wherein Y is thiazol-2-yl, Z is 3-(4-trifluoromethylphenyl)-1H-indol-6-yl, and s is 0;
a compound wherein Y is thiazol-2-yl, Z is 3-(3-trifluoromethylphenyl)-1H-indol-6-yl, and s is 0;
a compound wherein Y is thiazol-2-yl, Z is 5-phenyl-benzofuran-2-yl, and s is 0;
a compound wherein Y is thiazol-2-yl, Z is 5-(3-trifluoromethylphenyl)-benzofuran-2-yl, and s is 0;
a compound wherein Y is thiazol-4-yl, Z is 3-(4-trifluoromethylphenyl)-1H-indol-6-yl, and s is 0;
a compound wherein Y is thiazol-4-yl, Z is 3-(3-trifluoromethylphenyl)-1H-indol-6-yl, and s is 0;
a compound wherein Y is thiazol-2-yl, Z is 3-methyl-5-phenyl-benzothien-2-yl, and s is 0;
a compound wherein Y is thiazol-2-yl, Z is 1-methyl-3-(4-trifluoromethylphenyl)-indol-6-yl, and s is 0;
a compound wherein Y is thiazol-2-yl, Z is 1-(4-fluorophenyl)-4-fluoro-indol-5-yl, and s is 0;
a compound wherein Y is thiazol-2-yl, Z is 1-(4-fluorophenyl)-6-fluoro-indol-5-yl, and s is 0;
a compound wherein Y is thiazol-2-yl, Z is 1-(4-fluorophenyl)-7-fluoro-indol-5-yl, and s is 0;
a compound wherein Y is thiazol-2-yl, Z is 4-(3-trifluoromethylphenyl)-5-methylthien-2-yl, and s is 0;
a compound wherein Y is thiazol-2-yl, Z is 5-(4-trifluoromethylphenyl)-4-methylthien-2-yl, and s is 0;
a compound wherein Y is thiazol-2-yl, Z is 5-(4-fluorophenyl)-4-methyl-thien-2-yl, and s is 0;
a compound wherein Y is thiazol-2-yl, Z is 5-(3-trifluoromethylphenyl)-4-methylthien-2-yl, and s is 0;
a compound wherein Y is thiazol-2-yl, Z is 1-(4-fluorophenyl)-7-methyl-indol-5-yl, and s is 0;
a compound wherein Y is thiazol-2-yl, Z is 1-(3-trifluoromethylphenyl)-indol-5-yl, and s is 0;
a compound wherein Y is thiazol-2-yl, Z is 1-(4-trifluoromethylphenyl)-indol-5-yl, and s is 0;
a compound wherein Y is thiazol-4-yl, Z is 1-(4-fluorophenyl)-indol-5-yl, and s is 0;
a compound wherein Y is thiazol-4-yl, Z is 1-(4-trifluoromethylphenyl)-indol-5-yl, and s is 0;
a compound wherein Y is thiazol-2-yl, Z is 1-phenyl-indazol-5-yl, and s is 0;
a compound wherein Y is thiazol-2-yl, Z is 4-(5-trifluoromethylthien-2-yl)-phenyl, and s is 0;
a compound wherein Y is thiazol-2-yl, Z is 1-(3,4-difluorophenyl)-indol-5-yl, and s is 0;
a compound wherein Y is thiazol-4-yl, Z is 1-(3,4-difluorophenyl)-indol-5-yl, and s is 0;
a compound wherein Y is thiazol-2-yl, Z is 1-(2,4-difluorophenyl)-indol-5-yl, and s is 0;
a compound wherein Y is thiazol-2-yl, Z is 1-(4-fluorophenyl)-3-chloro-indol-5-yl, and s is 0;
a compound wherein Y is 1H-pyrrol-2-yl, Z is 1-(3,4-difluorophenyl)-indol-5-yl, and s is 0;
a compound wherein Y is thiazol-2-yl, Z is 1-(3,4,5-trifluoro-phenyl)-indol-5-yl, and s is 0;
a compound wherein Y is thiazol-2-yl, Z is 1-(3-fluorophenyl)-3-methyl-indol-5-yl, and s is 0;
a compound wherein Y is thiazol-2-yl, Z is 1-(4-trifluoromethoxyphenyl)-indol-5-yl, and s is 0;
a compound wherein Y is thiazol-4-yl, Z is 1-(4-trifluoromethoxyphenyl)-indol-5-yl, and s is 0;
a compound wherein Y is thiazol-2-yl, Z is 1-(3,5-difluorophenyl)-indol-5-yl, and s is 0;
a compound wherein Y is thiazol-2-yl, Z is 1-(3-fluoro-4-chlorophenyl)-indol-5-yl, and s is 0;
a compound wherein Y is thiazol-2-yl, Z is 1-(2,5-difluorophenyl)-indol-5-yl, and s is 0;
a compound wherein Y is thiazol-2-yl, Z is 1-(3-trifluoromethoxyphenyl)-indazol-5-yl, and s is 0;
a compound wherein Y is thiazol-2-yl, Z is 1-(4-cyano-3-methylphenyl)-indol-5-yl, and s is 0;
a compound wherein Y is thiazol-2-yl, Z is 2-(3-trifluoromethoxyphenyl)-indazol-5-yl, and s is 0;
a compound wherein Y is thiazol-2-yl, Z is 3-methoxy-4-phenyl-phenyl, and s is 0;
a compound wherein Y is thiazol-2-yl, Z is 2-methyl-5-phenyl-furan-3-yl, and s is 0;
a compound wherein Y is thiazol-2-yl, Z is 2-trifluoromethyl-5-phenyl-furan-3-yl, and s is 0;
a compound wherein Y is thiazol-4-yl, Z is 2-(4-chlorophenyl)-benzoxazol-7-yl, and s is 0;
a compound wherein Y is thiazol-4-yl, Z is 2-(3-chlorophenyl)-4-methyl-thiazol-5-yl, and s is 0;
a compound wherein Y is thiazol-4-yl, Z is 2-phenyl-benzoxazol-5-yl, and s is 0;
a compound wherein Y is biphenyl-4-yl, Z is 1H-pyrrol-2-yl, and s is 0;
a compound wherein Y is thiazol-4-yl, Z is 2-(4-chlorophenyl)-4-methyl-thiazol-5-yl, and s is 0;
a compound wherein Y is thiazol-2-yl, Z is 2-phenyl-5-trifluoromethyl-oxazol-4-yl, and s is 0;
a compound wherein Y is thiazol-4-yl, Z is 2-(4-fluorophenyl)-4-methyl-thiazol-5-yl, and s is 0;
a compound wherein Y is thiazol-2-yl, Z is 2-(pyridin-4-yl)-3H-benzimidazol-4-yl, and s is 0;
a compound wherein Y is thiazol-4-yl, Z is 2-(2-fluorophenyl)-1H-benzimidazol-4-yl, and s is 0;
a compound wherein Y is thiazol-4-yl, Z is 2-(3-chlorophenyl)-3H-benzimidazol-4-yl, and s is 0;
a compound wherein Y is thiazol-4-yl, Z is 2-phenyl-3H-benzimidazol-4-yl, and s is 0;
a compound wherein Y is thiazol-4-yl, Z is 2-(3-fluorophenyl)-1H-benzimidazol-4-yl, and s is 0;
a compound wherein Y is thiazol-2-yl, Z is 1-phenyl-5-trifluoromethyl-pyrazol-4-yl, and s is 0;
a compound wherein Y is thiazol-4-yl, Z is 2-(4-fluorophenyl)-1H-benzimidazol-4-yl, and s is 0;
a compound wherein Y is thiazol-4-yl, Z is 2-(2-chlorophenyl)-1H-benzimidazol-4-yl, and s is 0;
a compound wherein Y is thiazol-4-yl, Z is 2-(3,5-dichlorophenyl)-thiazol-4-yl, and s is 0;
a compound wherein Y is thiazol-4-yl, Z is 2-methyl-5-phenyl-furan-3-yl, and s is 0;
a compound wherein Y is thiazol-4-yl, Z is 5-phenyl-2-trifluoromethyl-furan-3-yl, and s is 0;

a compound wherein Y is cyclopentyl, Z is biphenyl-4-yl, and s is 0;
a compound wherein Y is thiazol-4-yl, Z is 2-furan-2-yl-3H-benzimidazol-4-yl, and s is 0;
a compound wherein Y is biphenyl-4-yl, Z is pyrimidin-2-yl, and s is 0;
a compound wherein Y is biphenyl-4-yl, Z is thiazol-2-yl, s is 1, and R1 is 2-phenyl;
a compound wherein Y is biphenyl-4-yl, Z is thiazol-4-yl, s is 1, and R1 is 2-phenyl;
a compound wherein Y is thiazol-4-yl, Z is 2-phenyl-5-trifluoromethyl-oxazol-4-yl, and s is 0;
a compound wherein Y is thiazol-2-yl, Z is biphenyl-4-yl, s is 1, and R1 is 3-phenyl;
a compound wherein Y is thiazol-2-yl, Z is 2-fluoro-4-phenyl-phenyl, and s is 0;
a compound wherein Y is thiazol-4-yl, Z is 3-methyl-4-phenyl-phenyl, and s is 0;
a compound wherein Y is thiazol-2-yl, Z is 2-(3-trifluoromethylphenyl)-4-methyl-thiazol-5-yl, and s is 0;
a compound wherein Y is thiazol-4-yl, Z is 1-(3-trifluoromethylphenyl)-indol-5-yl, and s is 0;
a compound wherein Y is trifluoromethyl, Z is 1-(5-chloropyridin-2-yl)-indol-5-yl, and s is 0;
a compound wherein Y is thiazol-2-yl, Z is 1-(2-methyl-pyridin-4-yl)-indol-5-yl, and s is 0;
a compound wherein Y is thiazol-2-yl, Z is 1-(1-phenyl-ethyl)-indazol-5-yl, and s is 0;
a compound wherein Y is thiazol-2-yl, Z is 4-(5-(4-fluorophenyl)-pyrazol-1-yl)-phenyl, and s is 0;
a compound wherein Y is thiazol-2-yl, Z is 4-(3-methyl-indol-1-yl)-phenyl, and s is 0;
a compound wherein Y is thiazol-2-yl, Z is 1-(4-fluorophenyl)-4-chloro-indol-5-yl, and s is 0;
a compound wherein Y is thiazol-2-yl, Z is 1-(4-fluorophenyl)-6-methyl-indol-5-yl, and s is 0;
a compound wherein Y is thiazol-2-yl, Z is 1-(4-fluorophenyl)-6-chloro-indol-5-yl, and s is 0;
a compound wherein Y is thiazol-2-yl, Z is 1-(3-cyano-4-fluorophenyl)-indol-5-yl, and s is 0; a compound wherein Y is thiazol-2-yl, Z is 1-(3-aminocarbonyl-4-fluorophenyl)-indol-5-yl, and s is 0;
a compound wherein Y is thiazol-2-yl, Z is 1-(3-trifluoromethylphenyl)-indazol-5-yl, and s is 0;
a compound wherein Y is thiazol-2-yl, Z is 2-(3-trifluoromethylphenyl)-indazol-5-yl, and s is 0;
a compound wherein Y is thiazol-4-yl, Z is 1-(4-cyano-3-methylphenyl)-indol-5-yl, and s is 0;
a compound wherein Y is thiazol-4-yl, Z is 2-(3-trifluoromethoxyphenyl)-indazol-5-yl, and s is 0;
a compound wherein Y is 5-chloro-thien-2-yl, Z is 1-(4-fluorophenyl)-indol-5-yl, and s is 0;
a compound wherein Y is 3-fluorophenyl, Z is 1-(4-fluorophenyl)-indol-5-yl, and s is 0;
a compound wherein Y is 5-chloro-furan-2-yl, Z is 1-(4-fluorophenyl)-indol-5-yl, and s is 0;
a compound wherein Y is oxazol-2-yl, Z is 1-(4-fluorophenyl)-indol-5-yl, and s is 0;
a compound wherein Y is 5-fluoro-thien-2-yl, Z is 1-(4-fluorophenyl)-indol-5-yl, and s is 0;
a compound wherein Y is oxazol-4-yl, Z is 1-(4-fluorophenyl)-indol-5-yl, and s is 0;
a compound wherein Y is oxazol-5-yl, Z is 1-(4-fluorophenyl)-indol-5-yl, and s is 0;
or a pharmaceutically acceptable salt form thereof.

By a "therapeutically effective amount" of the MGL inhibitor as above described is meant a sufficient amount of the compound for treating fibrosis. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the MGL inhibitor is administered to the subject in the form of a pharmaceutical composition. Typically, the MGL inhibitor may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The MGL inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: Experimental protocol of the model of liver fibrosis regression. C57BL/6J mice received bi-weekly i.p. injections of CCl4 for 6 weeks. Injections of MGL inhibitors or vehicle started 2 hours prior the last injection of CCl4 and were administered daily until the end of the experiment. Mice were sacrificed either at day 1 (24 hrs), 4 or 7.

Figure 2A:
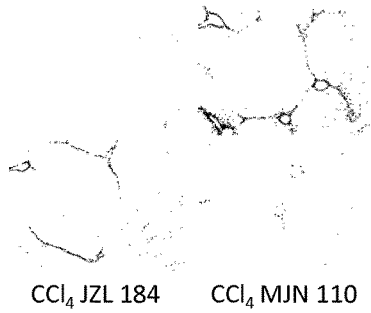
Figure 2A:
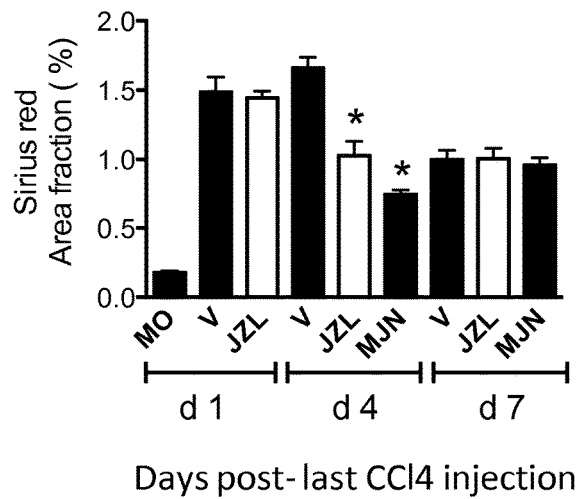
Figure 2B:
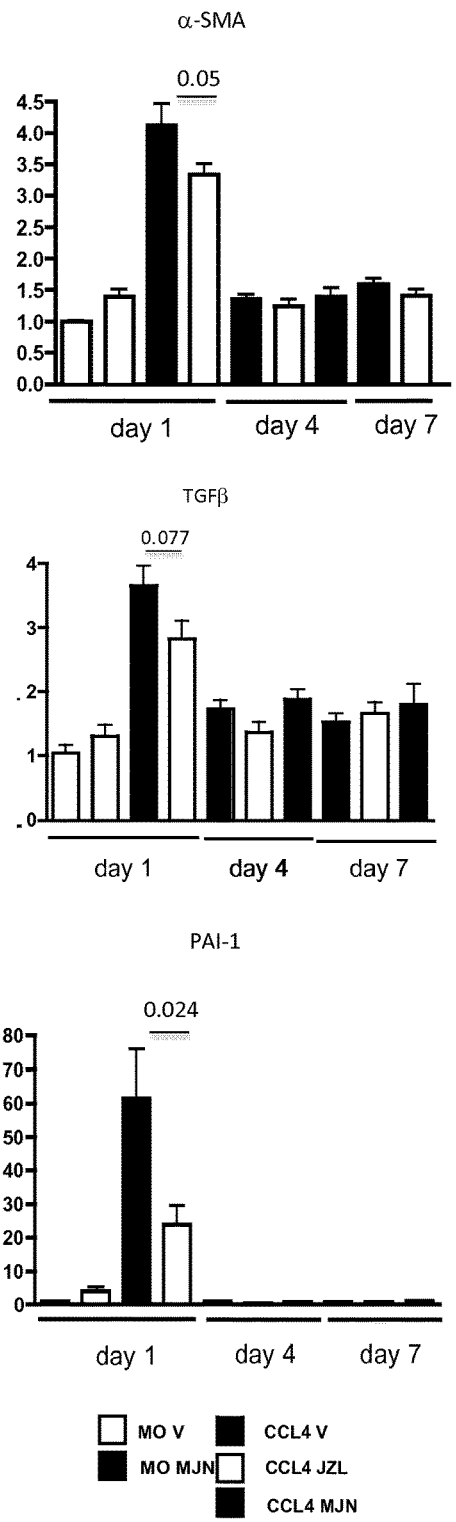

FIG. 2: Pharmacological inhibitors of MGL accelerates liver fibrosis regression. (a) picrosirius red staining. Representative image of picrosirius-red stained liver tissue sections from mice treated with MGL inhibitors or vehicle for 4 days (left). Morphometric analysis. Results are expressed as mean±SEM of % stained area (n=7-9 CCl4-treated animals and n=5 for mineral oil and vehicle-treated group, * p<0.002). (B) mRNA EXPRESSION OF FIBROGENIC GENES. All data are expressed as mean±SEM of n=7-9 animals for each treatment and n=5 for control groups.

Figure 3:
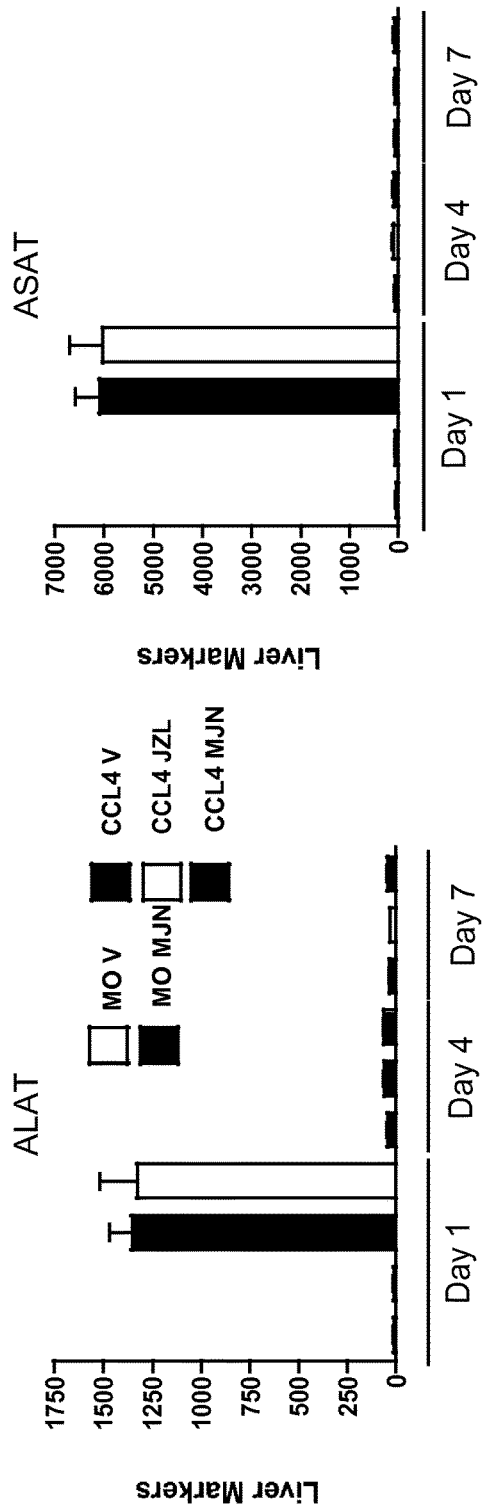

FIG. 3: MGL inhibition does not modify liver injury. Serum levels of ALAT and ASAT was determined in control mice and in mice after the stated time points after the final CCL4 dose and in the presence or absence of MGL inhibitors daily administered. All data are expressed as mean±SEM, of n=7-9 animals for each treatment and n=5 for control groups.

Figure 4:
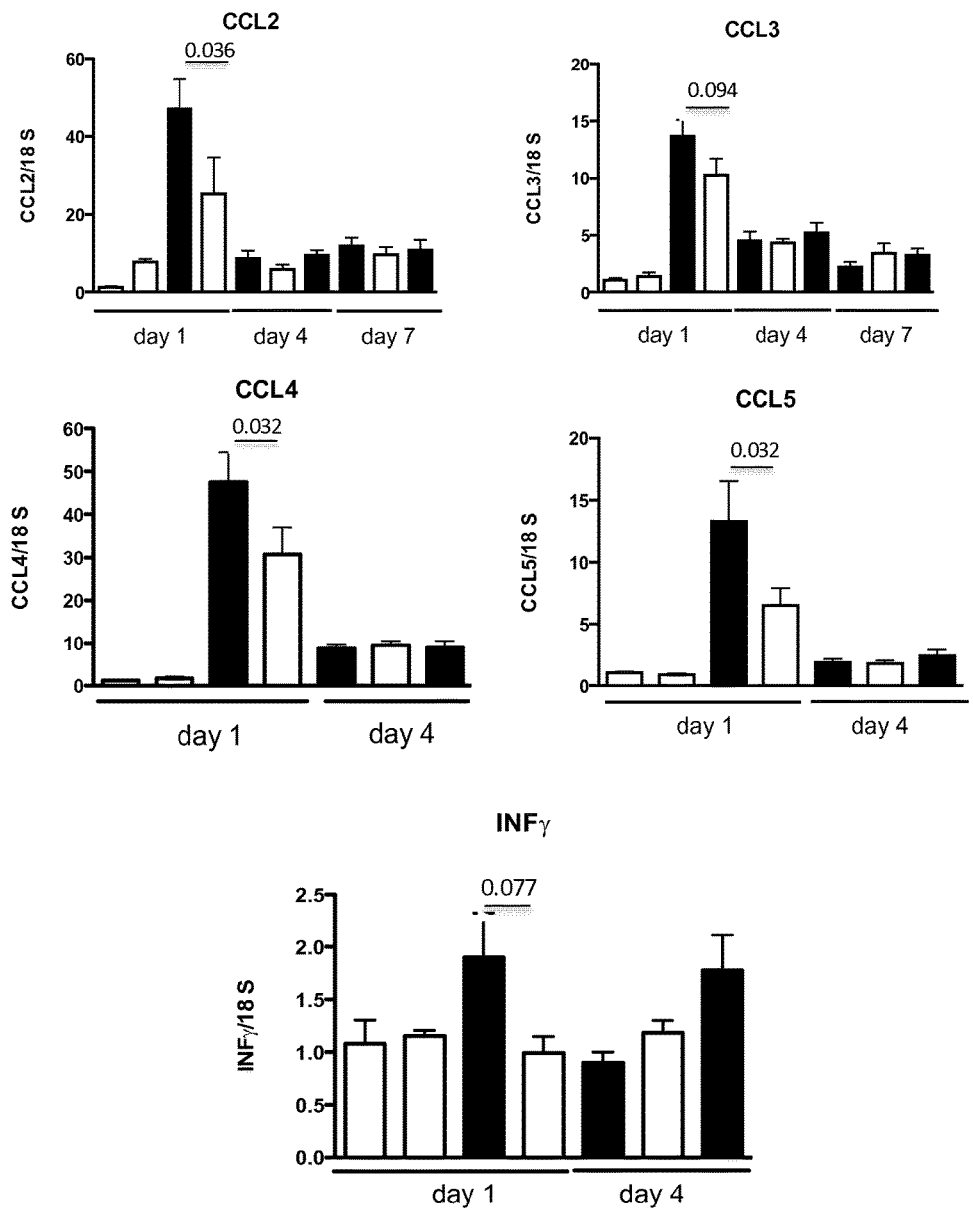

FIG. 4: MGL inhibitors reduce proinflammatory cytokines during fibrosis regression—mRNA expression of inflammatory genes. Total liver RNA was extracted at different point post CCL4 last injection and Q-PCR was performed. All data are expressed as mean±SEM, of n=7-9 animals for each treatment and 5 for control groups.

Figure 5:
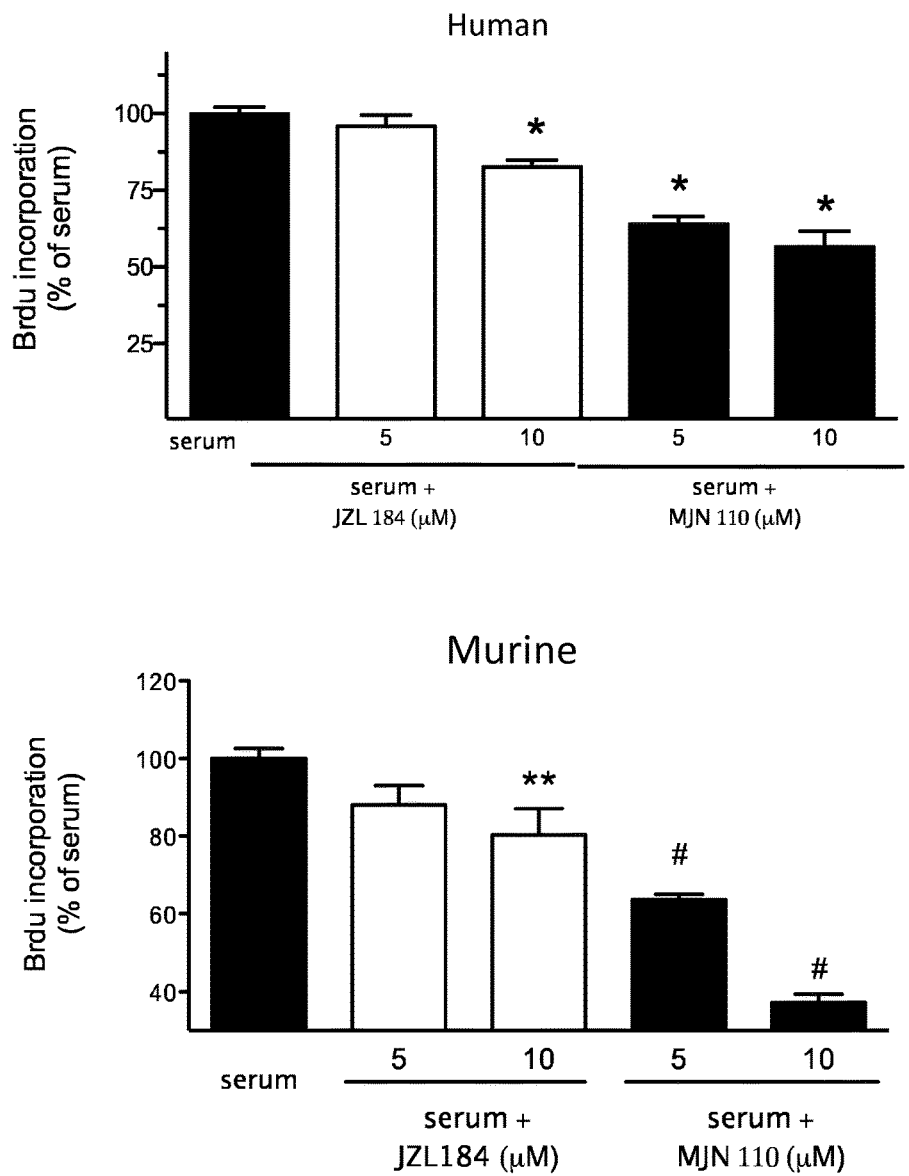

FIG. 5: MGL inhibitors inhibit DNA synthesis of human and murine hepatic myofibroblasts.

Figure 6:
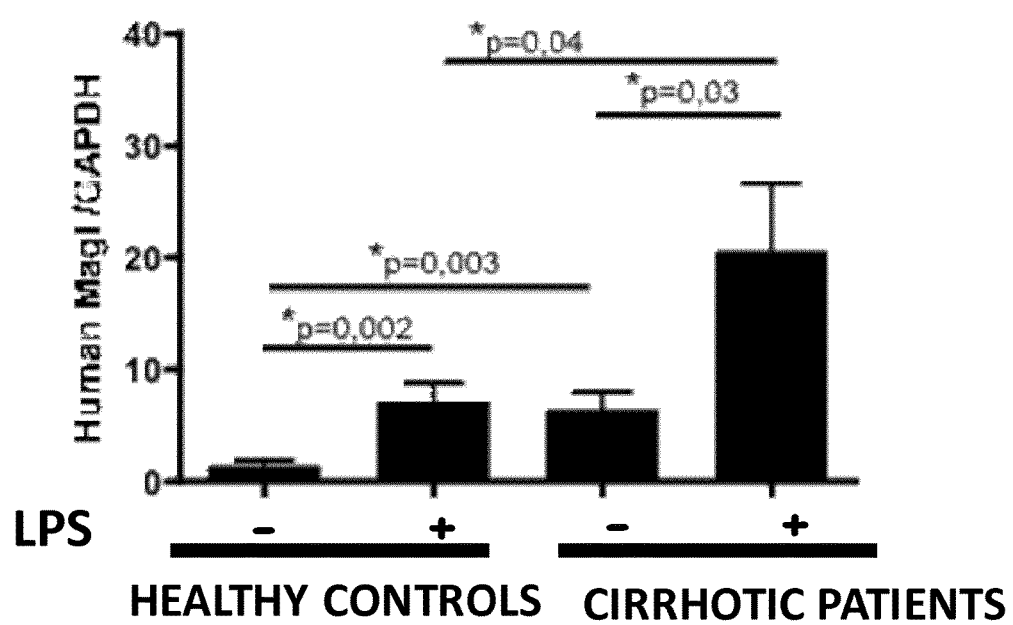

FIG. 6: MGL expression is induced in PBMC from patients with alcoholic cirrhosis.

FIG. 7: Mice bearing a global invalidation for MGL show decreased fibrosis. A. picrosirius red staining. B. mRNA expression of fibrogenic gene αSMA.

FIG. 8: Knock-Down of MGL in myeloid cells decreased liver fibrosis. A. picrosirius red staining. B. mRNA expression of fibrogenic gene αSMA.

EXAMPLE

Material & Methods

Mice:

C57Bl/6J mice were purchased from Janvier and kept under pathogen-free. Experiments were approved by the Paris-Nord Committee 121 for the Care and Use of Laboratory Animals.

Liver Fibrosis Model:

Hepatic fibrosis was induced in C57BL/6J mice (male, 11 weeks) by i.p. injection of carbon tetrachloride ($CCl_4$, Sigma 87030) 0.6 ml/kg body weight, 1/10 dilution in mineral oil (MO, Sigma, M-5310) twice a week for six weeks (total 13 injections). Control animals (n=5) received mineral oil.

Administration of Monoacylglycerol Lipase (MGL) Inhibitors:

MGL inhibitors (JZL 184, Cayman {Long, 2009 #6} and MJN 110 (kind gift of B. Cravatt, The Scripps Institute, {Niphakis, 2013 #7}), were diluted in Emulphor:ethanol:PBS; 1:1:18 and injected ip at dose of 15 mg/kg in and 10 mg/kg for JZL 184 (n=27) and MJN 110 (n=15), respectively. Mice were injected MGL inhibitors or vehicle 2 hours prior to the last CCL4 injection and daily until sacrifice. Animals were sacrificed 1, 4 or 7 days after the final injection of $CCl_4$.

Serum Analysis:

At the time of harvest, whole blood was collected from the inferior veina cava and serum was isolated by centrifugation at 7000 g for 5 min. Alanine aminotransferase and aspartate aminotransferase levels were measured at the Plateforme de Biochimie, Centre de Recherche sur l'Inflammation, INSERM U 1149, Bichat.

Histochemistry and Immunohistochemistry:

Liver tissue samples were fixed overnight in 10% formalin and further embedded in paraffin. Picrosirius red and Hematoxilin Eosin staining were performed on 4 μm thick tissue sections, according to standard protocols. Morphometric pixel analysis was performed on 10 non overlapping fields per mice (n=8-10 mice per group) at 100× magnification, using Image J software (NIH, USA).

Immunodetection of alpha-SMA was performed on 4 μm thick paraffin-embedded liver tissue sections. Antigen retrieval was performed by boiling 10 min in 10 mM sodium citrate buffer, pH 6. Endogenous peroxidase activity was blocked with 3% hydrogen peroxide and non-specific binding was performed after incubation with horse serum, biotin, avidin and mouse IgG using protein block kit (Vector). Anti-α-SMA primary antibody (Sigma, A-2547, clone 1A4) was incubated for 30 min at 1/3000. Biotinylated secondary goat anti-mouse antibody was used at 1/300 dilution and incubated 30 min at room temperature. Immunostaining was developped using 3,3'-diaminobenzidine (Dako), and slides were counterstained with hematoxylin eosin.

RNA Extraction and Q-PCR:

For each mouse, 2 samples from the median and left lobs were snap frozen in liquid nitrogen and stored at −80° C. until use. RNA was extracted using RNAsol (Qiagen) and RNAeasy mini columns (Qiagen) as previously described. Reverse transcription was performed on 2 μg RNA using High Capacity cDNA reverse transcriptase kit (Applied Biosystem) and Q-PCR was performed with ABsolute Blue QPCR SYBR Green Low ROX Mix (Thermo Scientific). Gene expression was calculated using AACT method relative to housekeeping gene 18S.

Isolation and Culture of Murine Hepatic Myofibroblasts:

Murine hepatic myofibroblasts were isolated from C57BL/6J mice and human hepatic myofibroblasts were isolated from normal human liver, as previously described (Teixeira-Clerc, F., Julien, et al, Nat. Med. 12,671-676, 2006; Mallat et al, JCI, 1996). Human cells were cultured in DMEM medium containing 5% FBS and 5% normal human serum (NHS) and mouse cells in DMEM medium containing 10% FBS. Cells were used between the fourth and ninth passage. DNA synthesis was measured using a Brdu proliferation assay kit (Roche) and 3-6 replicates per point, according to the manufacturer's instructions. Confluent mouse myofibroblasts were serum-starved for 24 h in a 0.02% BSA-containing medium, and human myofibroblasts for 3 days in serum free media. Cells were further incubated with different concentrations of JZL 184 or MJN 110 in the presence of 5% NHS (human) or FBS (mouse) for 24 hours. Brdu was added for the last 18 hours of incubation.

Statistical Analysis:

All data are expressed as mean±SEM. Statistical analysis were performed using unpaired t-test followed by Mann-Whitney GraphPad Prism version 5.00 Mac (GraphPad Software, San Diego). A $p<0.05$ was considered statistically significant.

Results

Results are depicted in FIGS. 1-8. The inventors show that MGL inhibitors accelerate liver fibrosis regression (FIG. 2). Moreover, the inventors show that MGL inhibitors reduce proinflammatory cytokines during fibrosis regression (FIG. 4) and inhibit DNA synthesis of human and murine hepatic myofibroblasts (FIG. 5).

The inventors used peripheral blood mononuclear cells (PBMC) from healthy controls and cirrhotic patients and demonstrated that MGL expression is induced in PBMC from patients with alcoholic cirrhosis (FIG. 6).

The inventors also demonstrated that mice bearing a global invalidation for MGL show decreased fibrosis (FIGS. 7A and B) and the Knock-Down of MGL in myeloid cells decreased liver fibrosis (FIGS. 8A and B).

REFERENCES

Throughout this application, various references describe the state of the art to which this invention pertains. The disclosures of these references are hereby incorporated by reference into the present disclosure.

The invention claimed is:

1. A method of reducing fibrosis in a subject in need thereof comprising administering to the subject a therapeutically effective amount of at least one monoacylglycerol lipase (MGL) inhibitor, wherein the fibrosis is not inflammation-induced fibrosis and wherein the MGL inhibitor is at least one of 2,5-dioxopyrrolidin-1-yl 4-(bis(4-chlorophenyl)methyl)piperazine-1-carboxylate and 4-nitrophenyl-4-[bis(1,3-benzodioxol-5-yl)(hydroxy)methyl]piperidine-1-carboxylate.

2. The method of claim 1 wherein the fibrosis affects at least one organ selected from the group consisting of skin, heart, liver, lung, and kidney.

3. The method of claim 1 wherein the fibrosis is selected from the group consisting of dermal scar formation, keloids, liver fibrosis, lung fibrosis, kidney fibrosis, glomerulosclerosis, pulmonary fibrosis, renal fibrosis, intestinal fibrosis, interstitial fibrosis, cystic fibrosis of the pancreas and lungs, injection fibrosis, endomyocardial fibrosis, mediastinal fibrosis, myelofibrosis, retroperitoneal fibrosis, progressive massive fibrosis, and nephrogenic systemic fibrosis.

4. The method of claim 1 wherein the fibrosis is liver fibrosis.

5. A method of reducing liver fibrosis in a subject in need thereof comprising administering to the subject a therapeutically effective amount of at least one monoacylglycerol lipase (MGL) inhibitor and wherein the MGL inhibitor is at least one of 2,5-dioxopyrrolidin-1-yl 4-(bis(4-chlorophenyl)methyl)piperazine-1-carboxylate and 4-nitrophenyl-4-[bis(1,3-benzodioxol-5-yl)(hydroxy)methyl]piperidine-1-carboxylate.

6. The method of claim 5 wherein the fibrosis is inflammation-induced fibrosis.

7. A method of reducing fibrosis in a subject in need thereof comprising administering to the subject a therapeutically effective amount of at least one MGL inhibitor, wherein the fibrosis is not inflammation-induced fibrosis and wherein the MGL inhibitor is a compound of the following formula:

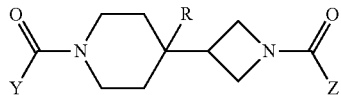

wherein the compound is selected from the group consisting of the compound wherein Y is thiazol-4-yl, Z is biphenyl-4-yl, and R is H;
the compound wherein Y is thiazol-2-yl, Z is biphenyl-4-yl, and R is H;
the compound wherein Y is isothiazol-5-yl, Z is biphenyl-4-yl, and R is H;
the compound wherein Y is 1H-pyrrol-3-yl, Z is biphenyl-4-yl, and R is H;
the compound wherein Y is thiazol-5-yl, Z is biphenyl-4-yl, and R is H;
the compound wherein Y is phenyl, Z is 5-trifluoromethyl-benzothien-2-yl, and R is OH;
the compound wherein Y is thiazol-4-yl, Z is 3-chloro-6-fluoro-benzothien-2-yl, and R is H;
the compound wherein Y is thiazol-2-yl, Z is 3-chloro-6-fluoro-benzothien-2-yl, and R is H;
the compound wherein Y is thiazol-4-yl, Z is 2-fluoro-4-phenyl-phenyl, and R is H;
the compound wherein Y is thiazol-4-yl, Z is 4-(3-trifluoromethylphenyl)-phenyl, and R is H;
the compound wherein Y is thiazol-4-yl, Z is 3-(3-fluorophenyl)-phenyl, and R is H;
the compound wherein Y is thiazol-4-yl, Z is 4-(5-trifluoromethylthien-2-yl)-phenyl, and R is H;
the compound wherein Y is thiazol-4-yl, Z is 4-(3-trifluoromethylphenylmethyl)-phenyl, and R is H;
the compound wherein Y is thiazol-4-yl, Z is 3-methyl-6-trifluoromethyl-benzothien-2-yl, and R is H;
the compound wherein Y is thiazol-2-yl, Z is 2-fluoro-4-phenyl-phenyl, and R is H;
the compound wherein Y is thiazol-2-yl, Z is 4-(3-trifluoromethylphenyl)-phenyl, and R is H;
the compound wherein Y is thiazol-2-yl, Z is 3-(3-fluorophenyl)-phenyl, and R is H;
the compound wherein Y is thiazol-2-yl, Z is 4-(5-trifluoromethylthien-2-yl)-phenyl, and R is H;
the compound wherein Y is thiazol-2-yl, Z is 4-(3-trifluoromethylphenylmethyl)-phenyl, and R is H;
the compound wherein Y is thiazol-2-yl, Z is 3-methyl-6-trifluoromethyl-benzothien-2-yl, and R is H;
the compound wherein Y is 1H-pyrrol-2-yl, Z is 2-fluoro-4-phenyl-phenyl, and R is H;
the compound wherein Y is 1H-pyrrol-2-yl, Z is 4-(3-trifluoromethylphenyl)-phenyl, and R is H;
the compound wherein Y is 1H-pyrrol-2-yl, Z is 3-(3-fluorophenyl)-phenyl, and R is H;
the compound wherein Y is 1H-pyrrol-2-yl, Z is 4-(5-trifluoromethylthien-2-yl)-phenyl, and R is H;
the compound wherein Y is 1H-pyrrol-2-yl, Z is 4-(3-trifluoromethylphenylmethyl)-phenyl, and R is H;
the compound wherein Y is 1H-pyrrol-2-yl, Z is 3-methyl-6-trifluoromethyl-benzothien-2-yl, and R is H;
the compound wherein Y is thiazol-2-yl, Z is 4-(4-trifluoromethylphenylmethyl)-phenyl, and R is H;
the compound wherein Y is thiazol-2-yl, Z is 2-phenyl-benzoxazol-6-yl, and R is H;
the compound wherein Y is thiazol-2-yl, Z is 3-chloro-6-trifluoromethyl-benzothien-2-yl, and R is H;
the compound wherein Y is thiazol-2-yl, Z is 1-(4-fluorophenyl)-1H-indol-5-yl, and R is H;
the compound wherein Y is thiazol-2-yl, Z is 1-(4-trifluoromethylphenyl)-1H-indol-5-yl, and R is H;
the compound wherein Y is thiazol-2-yl, Z is 1-(3,4-difluorophenyl)-1H-indol-5-yl, and R is H;
the compound wherein Y is thiazol-4-yl, Z is 4-(4-trifluoromethylphenylmethyl)-phenyl, and R is H;
the compound wherein Y is thiazol-4-yl, Z is 2-phenyl-benzoxazol-6-yl, and R is H;
the compound wherein Y is thiazol-4-yl, Z is 3-chloro-6-trifluoromethyl-benzothien-2-yl, and R is H;
the compound wherein Y is thiazol-4-yl, Z is 1-(4-fluorophenyl)-1H-indol-5-yl, and R is H;
the compound wherein Y is thiazol-4-yl, Z is 1-(4-trifluoromethylphenyl)-1H-indol-5-yl, and R is H;
the compound wherein Y is thiazol-4-yl, Z is 1-(3,4-difluorophenyl)-1H-indol-5-yl, and R is H;
the compound wherein Y is 1H-pyrrol-2-yl, Z is 4-(4-trifluoromethylphenylmethyl)-phenyl, and R is H;
the compound wherein Y is 1H-pyrrol-2-yl, Z is 2-phenyl-benzoxazol-6-yl, and R is H;
the compound wherein Y is 1H-pyrrol-2-yl, Z is 3-chloro-6-trifluoromethyl-benzothien-2-yl, and R is H;
the compound wherein Y is 1H-pyrrol-2-yl, Z is 1-(4-fluorophenyl)-1H-indol-5-yl, and R is H;
the compound wherein Y is 1H-pyrrol-2-yl, Z is 1-(4-trifluoromethylphenyl)-1H-indol-5-yl, and R is H;
the compound wherein Y is 1H-pyrrol-2-yl, Z is 1-(3,4-difluorophenyl)-1H-indol-5-yl, and R is H;
the compound wherein Y is 2-fluoro-4-phenyl-phenyl, Z is thiazol-2-yl, and R is H;
the compound wherein Y is 2-fluoro-4-phenyl-phenyl, Z is thiazol-4-yl, and R is H;
the compound wherein Y is 1H-pyrrol-2-yl, Z is 2-fluoro-4-phenyl-phenyl, and R is H;
the compound wherein Y is 4-(3-trifluoromethylphenyl)-phenyl, Z is thiazol-2-yl, and R is H;
the compound wherein Y is 4-(3-trifluoromethylphenyl)-phenyl, Z is thiazol-4-yl, and R is H;
the compound wherein Y is 4-(3-trifluoromethylphenyl)-phenyl, Z is 1H-pyrrol-2-yl, and R is H;
the compound wherein Y is 3-(3-fluorophenyl)-phenyl, Z is thiazol-2-yl, and R is H;
the compound wherein Y is 3-(3-fluorophenyl)-phenyl, Z is thiazol-4-yl, and R is H;
the compound wherein Y is 3-(3-fluorophenyl)-phenyl, Z is 1H-pyrrol-2-yl, and R is H;
the compound wherein Y is 4-(5-trifluoromethyl-thien-2-yl)-phenyl, Z is thiazol-2-yl, and R is H;
the compound wherein Y is 4-(5-trifluoromethyl-thien-2-yl)-phenyl, Z is thiazol-4-yl, and R is H;
the compound wherein Y is 4-(5-trifluoromethyl-thien-2-yl)-phenyl, Z is 1H-pyrrol-2-yl, and R is H;
the compound wherein Y is 4-(3-trifluoromethylphenylmethyl)-phenyl, Z is thiazol-2-yl, and R is H;
the compound wherein Y is 4-(3-trifluoromethylphenylmethyl)-phenyl, Z is thiazol-4-yl, and R is H;

the compound wherein Y is 4-(3-trifluoromethylphenyl-methyl)-phenyl, Z is 1H-pyrrol-2-yl, and R is H;
the compound wherein Y is 3-methyl-6-trifluoromethyl-benzothien-2-yl, Z is thiazol-2-yl, and R is H;
the compound wherein Y is 3-methyl-6-trifluoromethyl-benzothien-2-yl, Z is thiazol-4-yl, and R is H;
the compound wherein Y is 3-methyl-6-trifluoromethyl-benzothien-2-yl, Z is 1H-pyrrol-2-yl, and R is H;
the compound wherein Y is 4-(4-trifluoromethylphenyl-methyl)-phenyl, Z is thiazol-2-yl, and R is H;
the compound wherein Y is 4-(4-trifluoromethylphenyl-methyl)-phenyl, Z is thiazol-4-yl, and R is H;
the compound wherein Y is 4-(4-trifluoromethylphenyl-methyl)-phenyl, Z is 1H-pyrrol-2-yl, and R is H;
the compound wherein Y is 2-phenyl-benzoxazol-6-yl, Z is thiazol-2-yl, and R is H;
the compound wherein Y is 2-phenyl-benzoxazol-6-yl, Z is thiazol-4-yl, and R is H;
the compound wherein Y is 2-phenyl-benzoxazol-6-yl, Z is 1H-pyrrol-2-yl, and R is H;
the compound wherein Y is 3-chloro-6-trifluoromethyl-benzothien-2-yl, Z is thiazol-2-yl, and R is H;
the compound wherein Y is 3-chloro-6-trifluoromethyl-benzothien-2-yl, Z is thiazol-4-yl, and R is H;
the compound wherein Y is 3-chloro-6-trifluoromethyl-benzothien-2-yl, Z is 1H-pyrrol-2-yl, and R is H;
the compound wherein Y is 1-(4-fluorophenyl)-1H-indol-5-yl, Z is thiazol-2-yl, and R is H;
the compound wherein Y is 1-(4-fluorophenyl)-1H-indol-5-yl, Z is thiazol-4-yl, and R is H;
the compound wherein Y is 1-(4-fluorophenyl)-1H-indol-5-yl, Z is 1H-pyrrol-2-yl, and R is H;
the compound wherein Y is 1-(4-trifluoromethylphenyl)-1H-indol-5-yl, Z is thiazol-2-yl, and R is H;
the compound wherein Y is 1-(4-trifluoromethylphenyl)-1H-indol-5-yl, Z is thiazol-4-yl, and R is H;
the compound wherein Y is 1-(4-trifluoromethylphenyl)-1H-indol-5-yl, Z is 1H-pyrrol-2-yl, and R is H;
the compound wherein Y is 1-(3,4-difluorophenyl)-1H-indol-5-yl, Z is thiazol-2-yl, and R is H;
the compound wherein Y is 1-(3,4-difluorophenyl)-1H-indol-5-yl, Z is thiazol-4-yl, and R is H;
the compound wherein Y is 1-(3,4-difluorophenyl)-1H-indol-5-yl, Z is 1H-pyrrol-2-yl, and R is H;
the compound wherein Y is thiazol-2-yl, Z is 1-(4-fluorophenyl)-1H-benzimidazol-5-yl, and R is H;
the compound wherein Y is thiazol-2-yl, Z is 1-(3,4-difluorophenyl)-1H-benzimidazol-5-yl, and R is H;
the compound wherein Y is thiazol-2-yl, Z is 1-(4-trifluoromethylphenyl)-1H-benzimidazol-5-yl, and R is H;
the compound wherein Y is thiazol-2-yl, Z is 1-(2,2,2-trifluoroethyl)-1H-benzimidazol-5-yl, and R is H;
the compound wherein Y is thiazol-2-yl, Z is 1-(3,3,3-trifluoropropyl)-1H-benzimidazol-5-yl, and R is H;
the compound wherein Y is thiazol-2-yl, Z is 1-phenyl-2-methyl-1H-benzimidazol-5-yl, and R is H;
the compound wherein Y is thiazol-2-yl, Z is 1-(4-fluorophenyl)-2-methyl-1H-benzimidazol-5-yl, and R is H;
the compound wherein Y is thiazol-2-yl, Z is 1-(3,4-difluorophenyl)-2-methyl-1H-benzimidazol-5-yl, and R is H;
the compound wherein Y is thiazol-2-yl, Z is 1-(4-trifluoromethylphenyl)-2-methyl-1H-benzimidazol-5-yl, and R is H;
the compound wherein Y is thiazol-2-yl, Z is 1-(2,2,2-trifluoroethyl)-2-methyl-1H-benzimidazol-5-yl, and R is H;
the compound wherein Y is thiazol-2-yl, Z is 1-(3,3,3-trifluoropropyl)-2-methyl-1H-benzimidazol-5-yl, and R is H;
the compound wherein Y is thiazol-2-yl, Z is 1-(4,4-difluorocyclohexyl)-2-methyl-1H-benzimidazol-5-yl, and R is H;
the compound wherein Y is thiazol-2-yl, Z is 1-(5-chloropyridin-2-yl)-1H-indol-5-yl, and R is H;
the compound wherein Y is thiazol-2-yl, Z is 6-trifluoromethyl-benzothien-2-yl, and R is OH;
the compound wherein Y is thiazol-2-yl, Z is 1-(2-methylpyridin-4-yl)-1H-indol-5-yl, and R is H;
the compound wherein Y is thiazol-2-yl, Z is 1-phenyl-1,3-dihydro-3H-benzimidazol-2-on-5-yl, and R is H;
the compound wherein Y is thiazol-2-yl, Z is 1-(4-fluorophenyl)-1,3-dihydro-3H-benzimidazol-2-on-5-yl, and R is H;
the compound wherein Y is thiazol-2-yl, Z is 1-(3,4-difluorophenyl)-1,3-dihydro-3H-benzimidazol-2-on-5-yl, and R is H;
the compound wherein Y is thiazol-2-yl, Z is 1-(4-trifluoromethylphenyl)-1,3-dihydro-3H-benzimidazol-2-on-5-yl, and R is H;
the compound wherein Y is thiazol-2-yl, Z is 1-(3,3,3-trifluoropropyl)-1,3-dihydro-3H-benzimidazol-2-on-5-yl, and R is H; and
the compound wherein Y is thiazol-2-yl, Z is 1-(4,4-difluorocyclohexyl)-1,3-dihydro-3H-benzimidazol-2-on-5-yl, and R is H
or a pharmaceutically acceptable salt thereof.

8. The method of claim 7 wherein the fibrosis affects at least one organ selected from the group consisting of skin, heart, liver, lung, and kidney.

9. The method of claim 7 wherein the fibrosis is selected from the group consisting of dermal scar formation, keloids, liver fibrosis, lung fibrosis, kidney fibrosis, glomerulosclerosis, pulmonary fibrosis, renal fibrosis, intestinal fibrosis, interstitial fibrosis, cystic fibrosis of the pancreas and lungs, injection fibrosis, endomyocardial fibrosis, mediastinal fibrosis, myelofibrosis, retroperitoneal fibrosis, progressive massive fibrosis, and nephrogenic systemic fibrosis.

10. The method of claim 7 wherein the fibrosis is liver fibrosis.

11. A method of reducing fibrosis in a subject in need thereof comprising administering to the subject a therapeutically effective amount of at least one MGL inhibitor, wherein the fibrosis is not inflammation-induced fibrosis and wherein the MGL inhibitor is a compound of the following formula:

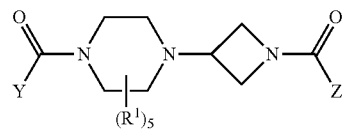

wherein the compound is selected from the group consisting of
the compound wherein Y is furan-2-yl, Z is 4-biphenyl, and s is 0;
the compound wherein Y is thiazol-4-yl, Z is 4-biphenyl, and s is 0;
the compound wherein Y is thiazol-5-yl, Z is 4-biphenyl, and s is 0;

the compound wherein Y is thiazol-2-yl, Z is 4-biphenyl, and s is 0;
the compound wherein Y is 2-methylthiazol-4-yl, Z is 4-biphenyl, and s is 0;
the compound wherein Y is 1-methyl-1H-pyrrol-2-yl, Z is 4-biphenyl, and s is 0;
the compound wherein Y is 5-bromofuran-2-yl, Z is 4-biphenyl, and s is 0;
the compound wherein Y is thien-2-yl, Z is 4-biphenyl, and s is 0;
the compound wherein Y is 5-methylthien-2-yl, Z is 4-biphenyl, and s is 0;
the compound wherein Y is 5-bromothien-2-yl, Z is 4-biphenyl, and s is 0;
the compound wherein Y is 5-chlorothien-2-yl, Z is 4-biphenyl, and s is 0;
the compound wherein Y is 3-bromothien-2-yl, Z is 4-biphenyl, and s is 0;
the compound wherein Y is 4-bromothien-2-yl, Z is 4-biphenyl, and s is 0;
the compound wherein Y is thieno[3,2-b]thiophen-2-yl, Z is 4-biphenyl, and s is 0;
the compound wherein Y is benzothien-2-yl, Z is 4-biphenyl, and s is 0;
the compound wherein Y is 3-methoxythien-2-yl, Z is 4-biphenyl, and s is 0;
the compound wherein Y is 4-biphenyl, Z is thiazol-2-yl, s is 1, and $R^1$ is 3-phenyl;
the compound wherein Y is thiazol-2-yl, Z is 4-biphenyl, s is 1, and $R^1$ is 2-methyl;
the compound wherein Y is thiazol-2-yl, Z is 4-biphenyl, s is 1, and $R^1$ is 2-phenyl;
the compound wherein Y is thiazol-2-yl, Z is 3-biphenyl, s is 1, and $R^1$ is 3-methyl;
the compound wherein Y is thiazol-2-yl, Z is 4-biphenyl, s is 1, and $R^1$ is 3-methyl;
the compound wherein Y is thiazol-2-yl, Z is 2-phenyl-4-methylthien-5-yl, and s is 0;
the compound wherein Y is thiazol-2-yl, Z is 2-(thien-2-yl)-4-methylthien-5-yl, and s is 0;
the compound wherein Y is thiazol-2-yl, Z is 2-(4-methylphenyl)-4-methylthien-5-yl, and s is 0;
the compound wherein Y is thiazol-2-yl, Z is 2-(4-trifluoromethylphenyl)-4-methylthien-5-yl, and s is 0;
the compound wherein Y is thiazol-2-yl, Z is 3-(thien-2-yl)phenyl, and s is 0;
the compound wherein Y is thiazol-2-yl, Z is 4-(thien-2-yl)phenyl, and s is 0;
the compound wherein Y is thiazol-2-yl, Z is 3-(pyridin-2-yl)phenyl, and s is 0;
the compound wherein Y is thiazol-2-yl, Z is 3-(pyridin-3-yl)phenyl, and s is 0;
the compound wherein Y is thiazol-2-yl, Z is 3-(pyridin-4-yl)phenyl, and s is 0;
the compound wherein Y is thiazol-2-yl, Z is 4-(pyridin-3-yl)phenyl, and s is 0;
the compound wherein Y is thiazol-2-yl, Z is 3-(pyrimidin-5-yl)phenyl, and s is 0;
the compound wherein Y is thiazol-2-yl, Z is 4-(pyrimidin-5-yl)phenyl, and s is 0;
the compound wherein Y is thiazol-2-yl, Z is 3-(pyrimidin-2-yl)phenyl, and s is 0;
the compound wherein Y is thiazol-2-yl, Z is 4-(pyrimidin-2-yl)phenyl, and s is 0;
the compound wherein Y is thiazol-2-yl, Z is 4-(2-trifluoromethylphenyl)phenyl, and s is 0;
the compound wherein Y is thiazol-2-yl, Z is 3-(2-trifluoromethylphenyl)phenyl, and s is 0;
the compound wherein Y is thiazol-2-yl, Z is 3-(4-trifluoromethylphenyl)phenyl, and s is 0;
the compound wherein Y is thiazol-2-yl, Z is 4-(4-trifluoromethylphenyl)phenyl, and s is 0;
the compound wherein Y is thiazol-2-yl, Z is 3-(6-bromopyridin-2-yl)phenyl, and s is 0;
the compound wherein Y is thiazol-2-yl, Z is 3-(5-nitropyridin-2-yl)phenyl, and s is 0;
the compound wherein Y is thiazol-2-yl, Z is 4-(5-nitropyridin-2-yl)phenyl, and s is 0;
the compound wherein Y is thiazol-2-yl, Z is 5-(4-fluorophenyl)pyridin-2-yl, and s is 0;
the compound wherein Y is thiazol-2-yl, Z is 2-(4-fluorophenyl)-thiazol-4-yl, and s is 0;
the compound wherein Y is thiazol-2-yl, Z is 2-(3-fluorophenyl)-thiazol-4-yl, and s is 0;
the compound wherein Y is thiazol-2-yl, Z is 2-(2,4-dichlorophenyl)-thiazol-4-yl, and s is 0;
the compound wherein Y is thiazol-2-yl, Z is 2-(3,5-dichlorophenyl)-thiazol-4-yl, and s is 0;
the compound wherein Y is thiazol-2-yl, Z is 2-(4-methoxyphenyl)-thiazol-4-yl, and s is 0;
the compound wherein Y is thiazol-2-yl, Z is 2-phenyl-thiazol-4-yl, and s is 0;
the compound wherein Y is thiazol-2-yl, Z is 4-(3-cyanophenyl)phenyl, and s is 0;
the compound wherein Y is thiazol-2-yl, Z is 4-(3-chlorophenyl)phenyl, and s is 0;
the compound wherein Y is thiazol-2-yl, Z is 4-(4-chlorophenyl)phenyl, and s is 0;
the compound wherein Y is thiazol-2-yl, Z is 4-(3,5-dichlorophenyl)phenyl, and s is 0;
the compound wherein Y is thiazol-2-yl, Z is 5-phenyl-pyridin-3-yl, and s is 0;
the compound wherein Y is thiazol-2-yl, Z is 3-fluoro-4-phenyl-phenyl, and s is 0;
the compound wherein Y is thiazol-2-yl, Z is 4-(4-cyanophenyl)phenyl, and s is 0;
the compound wherein Y is thiazol-2-yl, Z is 4-(4-bromophenyl)phenyl, and s is 0;
the compound wherein Y is thiazol-4-yl, Z is 5-phenyl-pyridin-3-yl, and s is 0;
the compound wherein Y is thiazol-4-yl, Z is 3-fluoro-4-phenyl-phenyl, and s is 0;
the compound wherein Y is thiazol-4-yl, Z is 4-(4-cyanophenyl)phenyl, and s is 0;
the compound wherein Y is thiazol-4-yl, Z is 4-(4-bromophenyl)phenyl, and s is 0;
the compound wherein Y is thiazol-2-yl, Z is 4-(4-fluorophenyl)phenyl, and s is 0;
the compound wherein Y is thiazol-2-yl, Z is 4-(3,4-dichlorophenyl)phenyl, and s is 0;
the compound wherein Y is thiazol-2-yl, Z is 4-(3-methylphenyl)phenyl, and s is 0;
the compound wherein Y is thiazol-2-yl, Z is 4-(3-fluoro-6-methylphenyl)phenyl, and s is 0;
the compound wherein Y is thiazol-2-yl, Z is 4-(3-chloro-4-fluorophenyl)-phenyl, and s is 0;
the compound wherein Y is thiazol-2-yl, Z is 4-(2,4-difluorophenyl)phenyl, and s is 0;
the compound wherein Y is thiazol-2-yl, Z is 4-(3-methoxyphenyl)phenyl, and s is 0;
the compound wherein Y is thiazol-2-yl, Z is 4-(benzo[1,3]dioxal-5-yl)phenyl, and s is 0;

the compound wherein Y is thiazol-2-yl, Z is 4-(naphth-2-yl)phenyl, and s is 0;
the compound wherein Y is thiazol-2-yl, Z is 4-(3-nitrophenyl)phenyl, and s is 0;
the compound wherein Y is thiazol-2-yl, Z is 4-quinolin-5-yl-phenyl, and s is 0;
the compound wherein Y is thiazol-2-yl, Z is 4-(3-carboxyphenyl)phenyl, and s is 0;
the compound wherein Y is thiazol-2-yl, Z is 4-(3-cyanomethylphenyl)phenyl, and s is 0;
the compound wherein Y is thiazol-2-yl, Z is 4-(3-methylsulfonylphenyl)phenyl, and s is 0;
the compound wherein Y is thiazol-2-yl, Z is 4-(4-methylcarbonylphenyl)phenyl, and s is 0;
the compound wherein Y is thiazol-2-yl, Z is 4-(3-formylphenyl)phenyl, and s is 0;
the compound wherein Y is thiazol-2-yl, Z is 4-(4-hydroxyphenyl)phenyl, and s is 0;
the compound wherein Y is thiazol-2-yl, Z is 4-(4-chloro-3-trifluoromethylphenyl)phenyl, and s is 0;
the compound wherein Y is thiazol-2-yl, Z is 4-(4-dimethylaminosulfonylphenyl)phenyl, and s is 0;
the compound wherein Y is thiazol-2-yl, Z is 4-(4,5-difluoro-2-methoxyphenyl)phenyl, and s is 0;
the compound wherein Y is thiazol-2-yl, Z is 4-(4-nitrophenyl)phenyl, and s is 0;
the compound wherein Y is thiazol-2-yl, Z is 4-(3-formyl-4-methoxyphenyl)phenyl, and s is 0;
the compound wherein Y is thiazol-2-yl, Z is 4-(3-aminocarbonylphenyl)phenyl, and s is 0;
the compound wherein Y is thiazol-2-yl, Z is 4-(3-hydroxyphenyl)phenyl, and s is 0;
the compound wherein Y is thiazol-2-yl, Z is 4-(3-methylsulfonylamino-phenyl)phenyl, and s is 0;
the compound wherein Y is thiazol-2-yl, Z is 4-(3-t-butoxycarbonylamino-phenyl)phenyl, and s is 0;
the compound wherein Y is thiazol-2-yl, Z is 4-(3-isobutyloxyphenyl)phenyl, and s is 0;
the compound wherein Y is thiazol-2-yl, Z is 4-(3-(2-cyanoethyl)aminocarbonyl-phenyl)phenyl, and s is 0;
the compound wherein Y is thiazol-2-yl, Z is 4-(3-(2-cyanoethenyl)phenyl)phenyl, and s is 0;
the compound wherein Y is thiazol-2-yl, Z is 4-(4-(2-methoxycarbonylethenyl)phenyl)phenyl, and s is 0;
the compound wherein Y is thiazol-4-yl, Z is 4-(4-fluorophenyl)phenyl, and s is 0;
the compound wherein Y is thiazol-4-yl, Z is 4-(2,4-difluorophenyl)phenyl, and s is 0;
the compound wherein Y is thiazol-4-yl, Z is 4-(3-chloro-4-fluorophenyl)phenyl, and s is 0;
the compound wherein Y is thiazol-4-yl, Z is 4-(3,4-dichlorophenyl)phenyl, and s is 0;
the compound wherein Y is thiazol-4-yl, Z is 4-(3-trifluoromethylphenyl)phenyl, and s is 0;
the compound wherein Y is thiazol-2-yl, Z is 4-(3-aminophenyl)phenyl, and s is 0;
the compound wherein Y is thiazol-2-yl, Z is 4-(3-methylcarbonylamino-phenyl)phenyl, and s is 0;
the compound wherein Y is thiazol-4-yl, Z is 4-(3-methylcarbonylamino-phenyl)phenyl, and s is 0;
the compound wherein Y is thiazol-4-yl, Z is 4-(3-methanesulfonylphenyl)phenyl, and s is 0;
the compound wherein Y is thiazol-2-yl, Z is 4-(3-trifluoromethylphenyl)phenyl, and s is 0;
the compound wherein Y is thiazol-2-yl, Z is 2-methyl-4-(3-trifluoromethylphenyl)phenyl, and s is 0;
the compound wherein Y is thiazol-4-yl, Z is 2-methyl-4-(3-trifluoromethylphenyl)phenyl, and s is 0;
the compound wherein Y is thiazol-2-yl, Z is 3-methyl-(3-trifluoromethylphenyl)phenyl, and s is 0;
the compound wherein Y is thiazol-4-yl, Z is 3-methyl-4-(3-trifluoromethylphenyl)phenyl, and s is 0;
the compound wherein Y is thiazol-2-yl, Z is 2-fluoro-4-(3-trifluoromethylphenyl)phenyl, and s is 0;
the compound wherein Y is thiazol-4-yl, Z is 2-fluoro-4-(3-trifluoromethylphenyl)phenyl, and s is 0;
the compound wherein Y is thiazol-2-yl, Z is 3-methoxy-4-(3-trifluoromethylphenyl)phenyl, and s is 0;
the compound wherein Y is thiazol-4-yl, Z is 3-methoxy-4-(3-trifluoromethylphenyl)phenyl, and s is 0;
the compound wherein Y is thiazol-2-yl, Z is 2-chloro-4-(3-trifluoromethylphenyl)phenyl, and s is 0;
the compound wherein Y is thiazol-4-yl, Z is 2-chloro-4-(3-trifluoromethylphenyl)phenyl, and s is 0;
the compound wherein Y is thiazol-4-yl, Z is 2-methyl-4-(3-chloro-4-fluorophenyl)phenyl, and s is 0;
the compound wherein Y is thiazol-4-yl, Z is 2-methyl-4-(4-chloro-3-trifluoromethylphenyl)phenyl, and s is 0;
the compound wherein Y is thiazol-4-yl, Z is 3-methyl-4-(3-chloro-4-fluorophenyl)phenyl, and s is 0;
the compound wherein Y is thiazol-4-yl, Z is 3-methyl-4-(4-chloro-3-trifluoromethylphenyl)phenyl, and s is 0;
the compound wherein Y is thiazol-4-yl, Z is 3-methoxy-4-(3-chloro-4-fluorophenyl)phenyl, and s is 0;
the compound wherein Y is thiazol-4-yl, Z is 3-methoxy-4-(4-chloro-3-trifluoromethylphenyl)phenyl, and s is 0;
the compound wherein Y is thiazol-4-yl, Z is 2-chloro-4-(3-chloro-4-fluorophenyl)phenyl, and s is 0;
the compound wherein Y is thiazol-4-yl, Z is 2-chloro-4-(4-chloro-3-trifluoromethylphenyl)phenyl, and s is 0;
the compound wherein Y is thiazol-4-yl, Z is 5-(4-methylphenyl)-1H-pyrrol-2-yl, and s is 0;
the compound wherein Y is 4-fluorophenyl, Z is 4-biphenyl, and s is 0;
the compound wherein Y is 2-fluorophenyl, Z is 4-biphenyl, and s is 0;
the compound wherein Y is thien-3-yl, Z is 4-biphenyl, and s is 0;
the compound wherein Y is 1H-pyrrol-2-yl, Z is 4-biphenyl, and s is 0;
the compound wherein Y is cyclopropyl, Z is 4-biphenyl, and s is 0;
the compound wherein Y is 3-fluorophenyl, Z is 4-biphenyl, and s is 0;
the compound wherein Y is oxazol-2-yl, Z is 4-biphenyl, and s is 0;
the compound wherein Y is [1,2,3]thiadiazol-4-yl, Z is 4-biphenyl, and s is 0;
the compound wherein Y is isoxazol-5-yl, Z is 4-biphenyl, and s is 0;
the compound wherein Y is furazan-3-yl, Z is 4-biphenyl, and s is 0;
the compound wherein Y is 4-cyanothien-2-yl, Z is 4-biphenyl, and s is 0;
the compound wherein Y is isothiazol-5-yl, Z is 4-biphenyl, and s is 0;
the compound wherein Y is pyrrol-3-yl, Z is 4-biphenyl, and s is 0;
the compound wherein Y is 5-chlorofuran-2-yl, Z is 4-biphenyl, and s is 0;
the compound wherein Y is thiazol-2-yl, Z is 2-(4-trifluoromethylphenyl)-benzoxazol-6-yl, and s is 0;

the compound wherein Y is thiazol-2-yl, Z is 2-phenyl-benzoxazol-5-yl, and s is 0;
the compound wherein Y is thiazol-2-yl, Z is 2-phenyl-benzoxazol-6-yl, and s is 0;
the compound wherein Y is thiazol-2-yl, Z is 5-phenyl-naphth-2-yl, and s is 0;
the compound wherein Y is thiazol-2-yl, Z is 3-chloro-6-phenyl-benzothien-2-yl, and s is 0;
the compound wherein Y is thiazol-4-yl, Z is 3-chloro-6-phenyl-benzothien-2-yl, and s is 0;
the compound wherein Y is 2-methylcarbonylamino-thiazol-4-yl, Z is 4-biphenyl, and s is 0;
the compound wherein Y is thiazol-4-yl, Z is 2-(3-trifluoromethylphenyl)-4-methyl-thiazol-5-yl, and s is 0;
the compound wherein Y is thiazol-2-yl, Z is 1-(4-fluorophenyl)-indol-5-yl, and s is 0;
the compound wherein Y is thiazol-4-yl, Z is 2-methyl-4-phenyl-phenyl, and s is 0;
the compound wherein Y is thiazol-2-yl, Z is 2-(4-chlorophenyl)-4-methyl-thiazol-5-yl, and s is 0;
the compound wherein Y is thiazol-2-yl, Z is 2-(3-chlorophenyl)-4-methyl-thiazol-5-yl, and s is 0;
the compound wherein Y is thiazol-2-yl, Z is 1-phenyl-3-methyl-indol-5-yl, and s is 0;
the compound wherein Y is thiazol-4-yl, Z is 1-(3,4,5-trifluoro-phenyl)-indol-5-yl, and s is 0;
the compound wherein Y is thiazol-2-yl, Z is 1-(4-fluorophenyl)-1H-pyrrolo[2,3-b]pyridin-5-yl, and s is 0;
the compound wherein Y is cyclopropyl, Z is 4-(3-trifluoromethylphenyl)-phenyl, and s is 0;
the compound wherein Y is thiazol-4-yl, Z is 3-methyl-5-phenyl-benzothien-2-yl, and s is 0;
the compound wherein Y is thiazol-2-yl, Z is 4-(3-fluorophenyl)-5-methyl-thien-2-yl, and s is 0;
the compound wherein Y is thiazol-2-yl, Z is 1-methyl-7-(3-trifluoromethylphenyl)-indol-5-yl, and s is 0;
the compound wherein Y is 1H-pyrrol-2-yl, Z is 1-(2,4-difluorophenyl)-indol-5-yl, and s is 0;
the compound wherein Y is 1H-pyrrol-2-yl, Z is 1-(6-trifluoromethylpyridin-3-yl)-indol-5-yl, and s is 0;
the compound wherein Y is thiazol-2-yl, Z is 3-fluoro-6-(4-trifluoromethylphenyl)-benzothien-2-yl, and s is 0;
the compound wherein Y is thiazol-2-yl, Z is 1-(4-trifluoromethylphenyl)-1H-benzimidazol-5-yl, and s is 0;
the compound wherein Y is thiazol-2-yl, Z is 4-methyl-5-(3-fluorophenyl)-thien-2-yl, and s is 0;
the compound wherein Y is thiazol-2-yl, Z is 1-methyl-7-(3-fluorophenyl)-indol-5-yl, and s is 0;
the compound wherein Y is 4-(3-trifluoromethylphenyl)-phenyl, Z is thiazol-4-yl, and s is 0;
the compound wherein Y is thiazol-2-yl, Z is 1-(3-trifluoromethoxyphenyl)-3-methyl-indol-5-yl, and s is 0;
the compound wherein Y is thiazol-4-yl, Z is 1-(4-fluorophenyl)-6-fluoro-indol-5-yl, and s is 0;
the compound wherein Y is thinol-4-yl, Z is 3-fluoro-4-(3-trifluoromethylphenyl)-phenyl, and s is 0;
the compound wherein Y is thiazol-4-yl, Z is 4-(5-trifluoromethylthien-2-yl)-phenyl, and s is 0;
the compound wherein Y is thiazol-2-yl, Z is 1-(6-methoxypyridin-3-yl)-indol-5-yl, and s is 0;
the compound wherein Y is thiazol-2-yl, Z is 1-(5-methylpyridin-2-yl)-indol-5-yl, and s is 0;
the compound wherein Y is thiazol-2-yl, Z is (2-methyl-4-phenyl)phenyl, and s is 0;
the compound wherein Y is thiazol-2-yl, Z is 3-methyl-5-(4-fluorophenyl)-1H-indol-2-yl, and s is 0;
the compound wherein Y is thiazol-4-yl, Z is 1-(4-fluorophenyl)-7-methyl-indol-5-yl, and s is 0;
the compound wherein Y is thiazol-2-yl, Z is 2-(3,4-difluorophenyl)-benzoxazol-6-yl, and s is 0;
the compound wherein Y is 5-chloro-furan-2-yl, Z is 4-(3-trifluoromethylphenyl)-phenyl, and s is 0;
the compound wherein Y is trifluoromethyl, Z is 1-(4-fluorophenyl)-indol-5-yl, and s is 0;
the compound wherein Y is thiazol-2-yl, Z is 1-(4-trifluoromethylphenyl)-indazol-5-yl, and s is 0;
the compound wherein Y is thiazol-4-yl, Z is 1-(4-fluorophenyl)-2,3-dihydro-1H-indol-5-yl, and s is 0;
the compound wherein Y is thiazol-2-yl, Z is 4-(4-fluorophenyl)-thiazol-2-yl, and s is 0;
the compound wherein Y is thiazol-2-yl, Z is 5-(4-chlorophenyl)-1-(3,4-dichlorophenyl)-1H-pyrazol-3-yl, and s is 0;
the compound wherein Y is thiazol-4-yl, Z is 1-methyl-3-(3-trifluoromethylphenyl)-indol-6-yl, and s is 0;
the compound wherein Y is oxazol-2-yl, Z is 4-(3-trifluoromethylphenyl)-phenyl, and s is 0;
the compound wherein Y is thiazol-2-yl, Z is 4-(4-trifluoromethyl-phenyl)-quinazolin-7-yl, and s is 0;
the compound wherein Y is 4-bromothien-2-yl, Z is 4-(3-trifluoromethylphenyl)-phenyl, and s is 0;
the compound wherein Y is thiazol-2-yl, Z is 1-(4-fluorophenyl)-3-methyl-indol-5-yl, and s is 0;
the compound wherein Y is 1-(4-fluorophenyl)-3-methyl-indol-5-yl, Z is thiazol-2-yl, and s is 0;
the compound wherein Y is thiazol-2-yl, Z is 1-(4-fluorophenyl)-indazol-5-yl, and s is 0;
the compound wherein Y is thiazol-2-yl, Z is 3-(4-methoxyphenyl)-phenyl, and s is 0;
the compound wherein Y is thiazol-2-yl, Z is 3-fluoro-5-(4-trifluoromethylphenyl)-benzothien-2-yl, and s is 0;
the compound wherein Y is thiazol-2-yl, Z is 3-(3-trifluoromethylphenyl)-phenyl, and s is 0;
the compound wherein Y is oxazol-4-yl, Z is 4-(3-trifluoromethylphenyl)-phenyl, and s is 0;
the compound wherein Y is thiazol-2-yl, Z is 3-trifluoromethyl-6-phenyl-benzothien-2-yl, and s is 0;
the compound wherein Y is thiazol-2-yl, Z is 4-(4-fluorophenyl)-5-methyl-thien-2-yl, and s is 0;
the compound wherein Y is isothiazol-5-yl, Z is 1-(4-trifluoromethylphenyl)-indol-5-yl, and s is 0;
the compound wherein Y is thiazol-4-yl, Z is 3-trifluoromethyl-6-phenyl-benzothien-2-yl, and s is 0;
the compound wherein Y is 1H-pyrrol-2-yl, Z is 1-(4-fluorophenyl)-2,3-dihydro-1H-indol-5-yl, and s is 0;
the compound wherein Y is thiazol-2-yl, Z is 1-methyl-3-(3-trifluoromethylphenyl)-indol-6-yl, and s is 0;
the compound wherein Y is thiazol-2-yl, Z is 1-methyl-7-(4-fluorophenyl)-indol-6-yl, and s is 0;
the compound wherein Y is thiazol-4-yl, Z is 3-chloro-4-(3-trifluoromethylphenyl)-phenyl, and s is 0;
the compound wherein Y is thiazol-2-yl, Z is 5-(4-chlorophenyl)-1-(2,4-dichlorophenyl)-4-methyl-1H-pyrazol-3-yl, and s is 0;
the compound wherein Y is thiazol-2-yl, Z is 3-phenyl-5-fluoro-phenyl, and s is 0;
the compound wherein Y is thiazol-2-yl, Z is 1-(6-methylpyridin-3-yl)-indol-5-yl, and s is 0;
the compound wherein Y is thiazol-2-yl, Z is 1-(3,4-difluorophenyl)-indazol-5-yl, and s is 0;
the compound wherein Y is thiazol-2-yl, Z is 1-(2-methoxypyridin-4-yl)-indol-5-yl, and s is 0;

the compound wherein Y is thiazol-4-yl, Z is 2-fluoro-4-phenyl-phenyl, and s is 0;
the compound wherein Y is thiazol-2-yl, Z is 1-(2-cyanophenyl)-indol-5-yl, and s is 0;
the compound wherein Y is thiazol-2-yl, Z is 1-(3-fluorophenyl)-indazol-5-yl, and s is 0;
the compound wherein Y is thiazol-4-yl, Z is 1-(4-fluorophenyl)-7-fluoro-indol-5-yl, and s is 0;
the compound wherein Y is 2,2-difluoro-cyclopropyl, Z is 4-(3-trifluoromethylphenyl)phenyl, and s is 0;
the compound wherein Y is thiazol-2-yl, Z is 1-(3-cyanophenyl)-indol-5-yl, and s is 0;
the compound wherein Y is isothiazol-5-yl, Z is 3-methyl-4-(3-trifluoromethylphenyl)phenyl, and s is 0;
the compound wherein Y is thiazol-2-yl, Z is 1-(3-methoxy-4-cyanophenyl)-indol-5-yl, and s is 0;
the compound wherein Y is thiazol-2-yl, Z is 1-(3-chloro-5-trifluoromethylpyridin-2-yl)-indol-5-yl, and s is 0;
the compound wherein Y is thiazol-2-yl, Z is 3-(2,4-difluorophenyl)phenyl, and s is 0;
the compound wherein Y is isoxazol-5-yl, Z is 4-(3-trifluoromethylphenyl)phenyl, and s is 0;
the compound wherein Y is thiazol-2-yl, Z is 2,3-diphenyl-1H-indol-6-yl, and s is 0;
the compound wherein Y is 1H-pyrrol-2-yl, Z is 1-(4-trifluoromethylphenyl)-indol-5-yl, and s is 0;
the compound wherein Y is thiazol-2-yl, Z is 1-(5-fluoropyridin-2-yl)-indol-5-yl, and s is 0;
the compound wherein Y is thiazol-2-yl, Z is 5-phenyl-thien-2-yl, and s is 0;
the compound wherein Y is thiazol-2-yl, Z is 4-(3,5-difluorophenyl)-pyrazol-1-yl, and s is 0;
the compound wherein Y is thiazol-2-yl, Z is 3-(3-fluorophenyl)phenyl, and s is 0;
the compound wherein Y is thiazol-2-yl, Z is 2-phenyl-benzothiazol-6-yl, and s is 0;
the compound wherein Y is thiazol-2-yl, Z is 1-(6-methyl-pyridin-2-yl)-indol-5-yl, and s is 0;
the compound wherein Y is thiazol-2-yl, Z is 1-(pyridin-4-yl)-indol-5-yl, and s is 0;
the compound wherein Y is thiazol-2-yl, Z is 1-(4-methyl-pyridin-2-yl)-indol-5-yl, and s is 0;
the compound wherein Y is thiazol-4-yl, Z is 1-(3,4-difluorophenyl)-indazol-5-yl, and s is 0;
the compound wherein Y is thiazol-2-yl, Z is 4-phenyl-quinazolin-7-yl, and s is 0;
the compound wherein Y is thiazol-2-yl, Z is 2-(3-fluorophenyl)-benzothiazol-6-yl, and s is 0;
the compound wherein Y is thiazol-2-yl, Z is 1-methyl-3-phenyl-indol-6-yl, and s is 0;
the compound wherein Y is thiazol-4-yl, Z is 1-(4-cyanophenyl)-indol-5-yl, and s is 0;
the compound wherein Y is 1-(3,4-difluorophenyl)-3-methyl-indol-5-yl, Z is thiazol-2-yl, and s is 0;
the compound wherein Y is thiazol-2-yl, Z is 1-(pyridin-2-yl)-indol-5-yl, and s is 0;
the compound wherein Y is 4-(5-trifluoromethylthien-2-yl)-phenyl, Z is thiazol-4-yl, and s is 0;
the compound wherein Y is thiazol-2-yl, Z is 1-methyl-3-phenyl-indazol-5-yl, and s is 0;
the compound wherein Y is 1H-pyrrol-2-yl, Z is 4-(5-trifluoromethylthien-2-yl)phenyl, and s is 0;
the compound wherein Y is thiazol-4-yl, Z is 1-(2,4-difluorophenyl)-indol-5-yl, and s is 0;
the compound wherein Y is furan-3-yl, Z is biphenyl-4-yl, and s is 0;
the compound wherein Y is thiazol-4-yl, Z is 2-phenyl-benzoxazol-6-yl, and s is 0;
the compound wherein Y is thiazol-2-yl, Z is 1-methyl-3-(3-fluorophenyl)-indol-6-yl, and s is 0;
the compound wherein Y is 5-chloro-thien-2-yl, Z is 4-(3-trifluoromethylphenyl)phenyl, and s is 0;
the compound wherein Y is thiazol-2-yl, Z is 3-phenyl-5-trifluoromethyl-phenyl, and s is 0;
the compound wherein Y is isoxazol-3-yl, Z is 4-(3-trifluoromethylphenyl)-phenyl, and s is 0;
the compound wherein Y is thiazol-2-yl, Z is 1-(3-trifluoromethylphenyl)-3-methyl-1H-thieno[2,3-c]pyrazol-5-yl, and s is 0;
the compound wherein Y is thiazol-2-yl, Z is 1-(5-fluoropyrimidin-2-yl)-indol-5-yl, and s is 0;
the compound wherein Y is thiazol-4-yl, Z is 1-methyl-3-(4-trifluoromethylphenyl)-indol-6-yl, and s is 0;
the compound wherein Y is thiazol-2-yl, Z is 3-methyl-5-(2-fluoropyridin-3-yl)-1H-indol-2-yl, and s is 0;
the compound wherein Y is thiazol-2-yl, Z is 4-methyl-(2-(4-fluorophenyl)-thiazol-5-yl, and s is 0;
the compound wherein Y is thiazol-4-yl, Z is 2-(3-trifluoromethylphenyl)-benzoxazol-6-yl, and s is 0;
the compound wherein Y is thiazol-4-yl, Z is 1-phenyl-3-methyl-indol-5-yl, and s is 0;
the compound wherein Y is thiazol-2-yl, Z is 1-(4-fluorophenyl)-1H-pyrrolo[3,2-b]pyridin-5-yl, and s is 0;
the compound wherein Y is thiazol-2-yl, Z is 2-phenyl-benxoxazol-7-yl, and s is 0;
the compound wherein Y is thiazol-4-yl, Z is 1-methyl-3-phenyl-indol-6-yl, and s is 0;
the compound wherein Y is thiazol-2-yl, Z is 4-(5-(4-methylphenyl)-[1,3,4]oxadiazol-2-yl)-phenyl, and s is 0;
the compound wherein Y is thiazol-2-yl, Z is 4-(4-fluorophenyl)-thien-2-yl, and s is 0;
the compound wherein Y is thiazol-2-yl, Z is 2-(3-trifluoromethylphenyl)-benzoxazol-6-yl, and s is 0;
the compound wherein Y is thiazol-2-yl, Z is 1-(4-cyanophenyl)-indol-5-yl, and s is 0;
the compound wherein Y is thiazol-2-yl, Z is 4-(3-fluorophenyl)-thien-2-yl, and s is 0;
the compound wherein Y is 4-(5-trifluoromethylthien-2-yl)-phenyl, Z is thiazol-2-yl, and s is 0;
the compound wherein Y is 4-(5-trifluoromethylthien-2-yl)-phenyl, Z is 1H-pyrrol-2-yl, and s is 0;
the compound wherein Y is thiazol-4-yl, Z is 1-phenyl-indazol-5-yl, and s is 0;
the compound wherein Y is thiazol-2-yl, Z is 1,5-diphenyl-pyrazol-3-yl, and s is 0;
the compound wherein Y is thiazol-2-yl, Z is 2-(pyridin-2-yl)-benzothiazol-6-yl, and s is 0;
the compound wherein Y is 4-(3-trifluoromethylphenyl)-phenyl, Z is 1H-pyrrol-2-yl, and s is 0;
the compound wherein Y is thiazol-2-yl, Z is 1-(4-fluorophenyl)-benzimidazol-5-yl, and s is 0;
the compound wherein Y is thiazol-2-yl, Z is 3-phenyl-4-methoxy-phenyl, and s is 0;
the compound wherein Y is oxazol-5-yl, Z is 4-(3-trifluoromethylphenyl)-phenyl, and s is 0;
the compound wherein Y is thiazol-2-yl, Z is 1-methyl-3-(3-fluorophenyl)-indazol-5-yl, and s is 0;
the compound wherein Y is thiazol-2-yl, Z is 1-(4-aminocarbonylphenyl)-indol-5-yl, and s is 0;
the compound wherein Y is thiazol-2-yl, Z is 2-fluoro-3-phenyl-phenyl, and s is 0;

the compound wherein Y is thiazol-2-yl, Z is 2-(2-chlorophenyl)-benzoxazol-4-yl, and s is 0;
the compound wherein Y is thiazol-2-yl, Z is 1-(pyrimidin-2-yl)-indol-5-yl, and s is 0;
the compound wherein Y is thiazol-2-yl, Z is 3-methyl-5-(5-methoxypyridin-3-yl)-1H-indol-2-yl, and s is 0;
the compound wherein Y is 1H-pyrrol-2-yl, Z is 1-(6-methoxypyridin-3-yl)-indol-5-yl, and s is 0;
the compound wherein Y is thiazol-2-yl, Z is 1-(3-aminocarbonylphenyl)-indol-5-yl, and s is 0;
the compound wherein Y is thiazol-4-yl, Z is 2-(3,4-difluorophenyl)-benzoxazol-6-yl, and s is 0;
the compound wherein Y is thiazol-2-yl, Z is 4,5-diphenyl-1H-imidazol-2-yl, and s is 0;
the compound wherein Y is thiazol-4-yl, Z is 1-(5-chloropyridin-2-yl)-indol-5-yl, and s is 0;
the compound wherein Y is 1H-pyrrol-2-yl, Z is 1-(6-methylpyridin-3-yl)-indol-5-yl, and s is 0;
the compound wherein Y is thiazol-4-yl, Z is 1-(2-cyanophenyl)-indol-5-yl, and s is 0;
the compound wherein Y is thiazol-2-yl, Z is 7-(3-fluorophenyl)-1H-indol-5-yl, and s is 0;
the compound wherein Y is trifluoromethyl, Z is 1-(5-methylpyridin-2-yl)-indol-5-yl, and s is 0;
the compound wherein Y is thiazol-4-yl, Z is 3-(2-trifluoromethylphenyl)-phenyl, and s is 0;
the compound wherein Y is thiazol-2-yl, Z is 1-(3,4-difluorophenyl)-benzimidazol-5-yl, and s is 0;
the compound wherein Y is thiazol-4-yl, Z is 2-phenyl-benzothiazol-6-yl, and s is 0;
the compound wherein Y is thiazol-4-yl, Z is 3-(3-trifluoromethylphenyl)-phenyl, and s is 0;
the compound wherein Y is 1H-pyrrol-2-yl, Z is 1-(pyridin-2-yl)-indol-5-yl, and s is 0;
the compound wherein Y is thiazol-2-yl, Z is 2-phenyl-benzoxazol-6-yl, and s is 0;
the compound wherein Y is thiazol-2-yl, Z is 2-(3-chlorophenyl)-benzoxazol-4-yl, and s is 0;
the compound wherein Y is thiazol-2-yl, Z is 1-(pyridin-3-yl)-indol-5-yl, and s is 0;
the compound wherein Y is thiazol-2-yl, Z is 2-(2-fluorophenyl)-benzoxazol-4-yl, and s is 0;
the compound wherein Y is thiazol-2-yl, Z is 2-phenyl-1H-benzimidazol-5-yl, and s is 0;
the compound wherein Y is thiazol-2-yl, Z is 1-methyl-3-(4-fluorophenyl)-indazol-5-yl, and s is 0;
the compound wherein Y is thiazol-2-yl, Z is 6-(5-methoxypyridin-3-yl)-1H-indol-2-yl, and s is 0;
the compound wherein Y is thiazol-4-yl, Z is 1-(4-methylpyridin-2-yl)-indol-5-yl, and s is 0;
the compound wherein Y is thiazol-4-yl, Z is 5-(4-chlorophenyl)-1-(2,4-dichlorophenyl)-4-methyl-1H-pyrazol-3-yl, and s is 0;
the compound wherein Y is trifluoromethyl, Z is 1-(4-methyl-pyridin-2-yl)-indol-5-yl, and s is 0;
the compound wherein Y is thiazol-2-yl, Z is 2-chloro-5-phenyl-phenyl, and s is 0;
the compound wherein Y is thiazol-4-yl, Z is 1-(pyrimidin-2-yl)-indol-5-yl, and s is 0;
the compound wherein Y is thiazol-2-yl, Z is 2-(2-fluorophenyl)-4-methyl-thiazol-5-yl, and s is 0;
the compound wherein Y is thiazol-2-yl, Z is 1-(4-fluorophenyl)-3-methyl-1H-pyrazolo[3,4-b]pyridin-5-yl, and s is 0;
the compound wherein Y is thiazol-2-yl, Z is 6-(4-fluorophenyl)-1H-indol-2-yl, and s is 0;
the compound wherein Y is thiazol-2-yl, Z is 3-methyl-5-(2-methyl-2H-pyrazol-3-yl)-1H-indol-2-yl, and s is 0;
the compound wherein Y is thiazol-2-yl, Z is 1-(3,4-difluorophenyl)-2-methyl-benzimidazol-5-yl, and s is 0;
the compound wherein Y is thiazol-2-yl, Z is 1-phenyl-benzimidazol-5-yl, and s is 0;
the compound wherein Y is thiazol-2-yl, Z is 2-fluoro-5-phenyl-phenyl, and s is 0;
the compound wherein Y is thiazol-2-yl, Z is 5-phenyl-furo[2,3-b]pyridin-2-yl, and s is 0;
the compound wherein Y is thiazol-2-yl, Z is 2-(thiazol-2-yl)-benzothiazol-6-yl, and s is 0;
the compound wherein Y is thiazol-2-yl, Z is 6-(3,5-dimethyl-isoxazol-4-yl)-1H-indol-2-yl, and s is 0;
the compound wherein Y is 2-methyl-4-(3-trifluoromethylphenyl)-phenyl, Z is thiazol-4-yl, and s is 0;
the compound wherein Y is thiazol-2-yl, Z is 5-(4-fluorophenyl)-furo[2,3-b]pyridin-2-yl, and s is 0;
the compound wherein Y is thiazol-2-yl, Z is 5-methyl-2-(4-methylphenyl)-2H-[1,2,3]triazol-4-yl, and s is 0;
the compound wherein Y is thiazol-2-yl, Z is 1-(4-trifluoromethylphenyl)-2-methyl-benzimidazol-5-yl, and s is 0;
the compound wherein Y is thiazol-2-yl, Z is 1-(2-methylpyrimidin-4-yl)-indol-5-yl, and s is 0;
the compound wherein Y is 2-methyl-thiazol-4-yl, Z is 4-(3-trifluoromethylphenyl)-phenyl, and s is 0;
the compound wherein Y is thiazol-2-yl, Z is 5-methyl-2-(4-chlorophenyl)-2H-[1,2,3]triazol-4-yl, and s is 0;
the compound wherein Y is 1-(3,4-difluorophenyl)-3-methyl-indol-5-yl, Z is 1H-pyrrol-2-yl, and s is 0;
the compound wherein Y is thiazol-2-yl, Z is 2-(4-chlorophenyl)-benzoxazol-4-yl, and s is 0;
the compound wherein Y is thiazol-4-yl, Z is 2-chloro-4-phenyl-phenyl, and s is 0;
the compound wherein Y is oxazol-4-yl, Z is biphenyl-4-yl, and s is 0;
the compound wherein Y is thiazol-2-yl, Z is 4-(benzimidazol-1-yl)-phenyl, and s is 0;
the compound wherein Y is thiazol-2-yl, Z is 1-(4-fluorophenyl)-indol-3-yl, and s is 0;
the compound wherein Y is thiazol-2-yl, Z is 1-(3,4-dichlorophenyl)-3,5-dimethyl-1H-pyrazol-4-yl, and s is 0;
the compound wherein Y is thiazol-2-yl, Z is 1-(3-fluorophenyl)-indol-3-yl, and s is 0;
the compound wherein Y is thiazol-2-yl, Z is 1-(4-fluorophenyl)-2-methyl-benzimidazol-5-yl, and s is 0;
the compound wherein Y is thiazol-4-yl, Z is 3-(3-fluorophenyl)-phenyl, and s is 0;
the compound wherein Y is thiazol-2-yl, Z is 1-phenyl-2-methyl-benzimidazol-5-yl, and s is 0;
the compound wherein Y is thiazol-4-yl, Z is 1-(4-fluorophenyl)-3-methyl-indol-5-yl, and s is 0;
the compound wherein Y is thiazol-4-yl, Z is 1-(4-trifluoromethylphenyl)-benzimidazol-5-yl, and s is 0;
the compound wherein Y is cyclobutyl, Z is biphenyl-4-yl, and s is 0;
the compound wherein Y is 2-phenyl-benzoxazol-6-yl, Z is thiazol-2-yl, and s is 0;
the compound wherein Y is thiazol-2-yl, Z is 2-methyl-3-phenyl-phenyl, and s is 0;
the compound wherein Y is biphenyl-4-yl, Z is isothiazol-5-yl, and s is 0;

the compound wherein Y is biphenyl-4-yl, Z is thiazol-2-yl, and s is 0;
the compound wherein Y is thiazol-4-yl, Z is 2-phenyl-benzoxazol-7-yl, and s is 0;
the compound wherein Y is thiazol-4-yl, Z is 2-(3-chlorophenyl)-benzoxazol-7-yl, and s is 0;
the compound wherein Y is thiazol-4-yl, Z is 3-(2,4-difluorophenyl)-phenyl, and s is 0;
the compound wherein Y is thiazol-4-yl, Z is 2-fluoro-3-phenyl-phenyl, and s is 0;
the compound wherein Y is thiazol-2-yl, Z is 6-(2-methyl-2H-pyrazol-3-yl)-1H-indol-2-yl, and s is 0;
the compound wherein Y is biphenyl-4-yl, Z is 3-fluorophenyl, and s is 0;
the compound wherein Y is 4-(3-trifluoromethylphenyl)-phenyl, Z is 1H-pyrrol-3-yl, and s is 0;
the compound wherein Y is thiazol-2-yl, Z is 6-(2-fluoropyridin-3-yl)-1H-indol-2-yl, and s is 0;
the compound wherein Y is thiazol-2-yl, Z is 4-(5-(4-methylphenyl)-[1,2,3]triazol-1-yl)-phenyl, and s is 0;
the compound wherein Y is biphenyl-4-yl, Z is thiazol-4-yl, and s is 0;
the compound wherein Y is 1H-pyrrol-2-yl, Z is 1-(pyridin-3-yl)-indol-5-yl, and s is 0;
the compound wherein Y is thiazol-4-yl, Z is 1-(5-fluoropyrimidin-2-yl)-indol-5-yl, and s is 0;
the compound wherein Y is thiazol-2-yl, Z is 4-(3-trifluoromethylpyrazol-1-yl)-phenyl, and s is 0;
the compound wherein Y is thiazol-4-yl, Z is 3-(4-methoxyphenyl)-phenyl, and s is 0;
the compound wherein Y is thiazol-2-yl, Z is 2-(pyridin-3-yl)-benzoxazol-4-yl, and s is 0;
the compound wherein Y is thiazol-2-yl, Z is 2-(furan-2-yl)-3H-benzimidazol-4-yl, and s is 0;
the compound wherein Y is thiazol-4-yl, Z is 3-methoxy-4-phenyl-phenyl, and s is 0;
the compound wherein Y is thiazol-2-yl, Z is 2-(3-fluorophenyl)-benzoxazol-7-yl, and s is 0;
the compound wherein Y is thiazol-2-yl, Z is 2-phenyl-3H-benzimidazol-4-yl, and s is 0;
the compound wherein Y is 2,2-difluoro-cyclopropyl, Z is biphenyl-4-yl, and s is 0;
the compound wherein Y is thiazol-2-yl, Z is 2-(4-fluorophenyl)-benzoxazol-4-yl, and s is 0;
the compound wherein Y is 4-(3-trifluoromethylphenyl)-phenyl, Z is oxazol-4-yl, and s is 0;
the compound wherein Y is thiazol-4-yl, Z is 3-phenyl-5-trifluoromethyl-phenyl, and s is 0;
the compound wherein Y is 2-methyl-4-(3-trifluoromethylphenyl)-phenyl, Z is thiazol-2-yl, and s is 0;
the compound wherein Y is thiazol-4-yl, Z is 1,5-diphenyl-1H-pyrazol-3-yl, and s is 0;
the compound wherein Y is isoxazol-3-yl, Z is biphenyl-4-yl, and s is 0;
the compound wherein Y is thiazol-2-yl, Z is 1-pyrimidin-5-yl-indol-5-yl, and s is 0;
the compound wherein Y is thiazol-4-yl, Z is 1-(3,4-difluorophenyl)-2-methyl-benzimidazol-5-yl, and s is 0;
the compound wherein Y is thiazol-4-yl, Z is 4-methoxy-3-phenyl-phenyl, and s is 0;
the compound wherein Y is biphenyl-4-yl, Z is thiazol-2-yl, s is 1, and $R^1$ is 3-phenylmethyl;
the compound wherein Y is thiazol-2-yl, Z is 1-(2,4-dichlorophenyl)-4,5,6,7-tetrahydro-1H-indazol-3-yl, and s is 0;
the compound wherein Y is thiazol-5-yl, Z is 4-(5-trifluoromethylthien-2-yl)-phenyl, and s is 0;
the compound wherein Y is 1H-[1,2,3]triazol-4-yl, Z is biphenyl-4-yl, and s is 0;
the compound wherein Y is thiazol-4-yl, Z is 1-(3,4-difluorophenyl)-benzimidazol-5-yl, and s is 0;
the compound wherein Y is 2-phenyl-1H-benzimidazol-5-yl, Z is thiazol-2-yl, and s is 0;
the compound wherein Y is thiazol-2-yl, Z is 2-(pyridin-4-yl)-4-methyl-thiazol-5-yl, and s is 0;
the compound wherein Y is thiazol-4-yl, Z is 3-fluoro-5-phenyl-phenyl, and s is 0;
the compound wherein Y is thiazol-4-yl, Z is 1-(4-fluorophenyl)-benzimidazol-5-yl, and s is 0;
the compound wherein Y is 2-phenyl-benzoxazol-6-yl, Z is thiazol-4-yl, and s is 0;
the compound wherein Y is biphenyl-4-yl, Z is [1,2,3]thiadiazol-4-yl, and s is 0;
the compound wherein Y is thiazol-2-yl, Z is 1-(4-fluorophenyl)-1H-pyrrolo[3,2-b]pyridin-6-yl, and s is 0;
the compound wherein Y is thiazol-4-yl, Z is 3-(4-trifluoromethylphenyl)-phenyl, and s is 0;
the compound wherein Y is thiazol-4-yl, Z is 1-(3-fluorophenyl)-indol-3-yl, and s is 0;
the compound wherein Y is thiazol-4-yl, Z is 2-fluoro-5-phenyl-phenyl, and s is 0;
the compound wherein Y is thiazol-4-yl, Z is 1-phenyl-benzimidazol-5-yl, and s is 0;
the compound wherein Y is thiazol-4-yl, Z is 2-(4-fluorophenyl)-benzoxazol-7-yl, and s is 0;
the compound wherein Y is biphenyl-4-yl, Z is oxazol-2-yl, and s is 0;
the compound wherein Y is biphenyl-4-yl, Z is thiazol-4-yl, s is 1, and $R^1$ is 3-phenylmethyl;
the compound wherein Y is thiazol-4-yl, Z is 2-methyl-3-phenyl-phenyl, and s is 0;
the compound wherein Y is biphenyl-4-yl, Z is thiazol-4-yl, s is 1, and $R^1$ is 2-spirofused cyclopropyl;
the compound wherein Y is thiazol-4-yl, Z is 2-(2-fluorophenyl)-4-methyl-thiazol-5-yl, and s is 0;
the compound wherein Y is thiazol-4-yl, Z is 2-chloro-5-phenyl-phenyl, and s is 0;
the compound wherein Y is thiazol-4-yl, Z is 1-(4-trifluoromethylphenyl)-2-methyl-benzimidazol-5-yl, and s is 0;
the compound wherein Y is thiazol-4-yl, Z is 2-(4-chlorophenyl)-1H-benzimidazol-4-yl, and s is 0;
the compound wherein Y is thiazol-4-yl, Z is 1-(4-fluorophenyl)-2-methyl-benzimidazol-5-yl, and s is 0;
the compound wherein Y is biphenyl-4-yl, Z is 1H-pyrrol-3-yl, and s is 0;
the compound wherein Y is thiazol-4-yl, Z is 4-benzimidazol-1-yl-phenyl, and s is 0;
the compound wherein Y is thiazol-2-yl, Z is 5-(4-fluorophenyl)-1H-benzimidazol-2-yl, and s is 0;
the compound wherein Y is thiazol-4-yl, Z is 1-(4-fluorophenyl)-indol-3-yl, and s is 0;
the compound wherein Y is thiazol-4-yl, Z is 1-phenyl-2-methyl-benzimidazol-5-yl, and s is 0;
the compound wherein Y is thiazol-2-yl, Z is 1,5-diphenyl-pyrazol-4-yl, and s is 0;
the compound wherein Y is 4-benzimidazol-1-yl-phenyl, Z is thiazol-2-yl, and s is 0;
the compound wherein Y is thiazol-4-yl, Z is 2-phenyl-1H-benzimidazol-5-yl, and s is 0;
the compound wherein Y is thiazol-2-yl, Z is 2-phenyl-[1,2,3]triazol-4-yl, and s is 0;

the compound wherein Y is thiazol-2-yl, Z is 1-(4-fluorophenyl)-3,5-dimethyl-1H-pyrazol-4-yl, and s is 0;

the compound wherein Y is thiazol-4-yl, Z is 4-(3-trifluoromethylpyrazol-1-yl)-phenyl, and s is 0;

the compound wherein Y is thiazol-2-yl, Z is 5-(4-trifluoromethoxyphenyl)-1H-benzimidazol-2-yl, and s is 0;

the compound wherein Y is thiazol-4-yl, Z is 1-(2,4-dichlorophenyl)-4,5,6,7-tetrahydro-1H-indazol-3-yi, and s is 0;

the compound wherein Y is 4-benzimidazol-1-yl-phenyl, Z is thiazol-4-yl, and s is 0;

the compound wherein Y is thiazol-2-yl, Z is biphenyl-4-yl, s is 1, and $R^1$ is 2(R,S)-trifluoromethyl, the compound wherein Y is thiazol-2-yl, Z is 5-(4-chlorophenyl)-1H-pyrrol-2-yl, and s is 0;

the compound wherein Y is 1H-indol-3-yl, Z is biphenyl-4-yl, and s is 0;

the compound wherein Y is 1H-pyrrol-2-yl, Z is 1-(2,4-dichlorophenyl)-4,5,6,7-tetrahydro-1H-indazol-3-yl, and s is 0;

the compound wherein Y is 1H-pyrazol-4-yl, Z is biphenyl-4-yl, and s is 0;

the compound wherein Y is trifluoromethyl, Z is 1-(2,4-dichlorophenyl)-4,5,6,7-tetrahydro-1H-indazol-3-yl, and s is 0;

the compound wherein Y is thiazol-2-yl, Z is 1-(6-trifluoromethylpyridin-3-yl)-indol-5-yl, and s is 0;

the compound wherein Y is thiazol-2-yl, Z is 1-(5-chloropyridin-2-yl)-indol-5-yl, and s is 0 the compound wherein Y is thiazol-2-yl, Z is 1-(5-trifluoromethylpyridin-2-yl)-indol-5-yl, and s is 0;

the compound wherein Y is thiazol-2-yl, Z is 3-fluoro-5-phenyl-benzothien-2-yl, and s is 0;

the compound wherein Y is thiazol-2-yl, Z is 3-phenyl-1H-indol-6-yl, and s is 0;

the compound wherein Y is thiazol-2-yl, Z is 3-(4-fluorophenyl)-1H-indol-6-yl, and s is 0;

the compound wherein Y is thiazol-2-yl, Z is 1-methyl-3-(4-fluorophenyl)-indol-6-yl, and s is 0;

the compound wherein Y is thiazol-2-yl, Z is 3-(3-fluorophenyl)-1H-indol-6-yl, and s is 0;

the compound wherein Y is thiazol-2-yl, Z is 1-(4-fluorophenyl)-indol-4-yl, and s is 0;

the compound wherein Y is thiazol-2-yl, Z is 4-(3-trifluoromethylphenyl)-thien-2-yl, and s is 0;

the compound wherein Y is thiazol-2-yl, Z is 3-methyl-4-phenyl-phenyl, and s is 0;

the compound wherein Y is thiazol-2-yl, Z is 2-chloro-4-phenyl-phenyl, and s is 0;

the compound wherein Y is 1H-pyrrol-3-yl, Z is 4-(3-trifluoromethylphenyl)-phenyl, and s is 0;

the compound wherein Y is 1H-pyrrol-2-yl, Z is 4-(3-trifluoromethylphenyl)-phenyl, and s is 0;

the compound wherein Y is thiazol-2-yl, Z is 4-(4-phenyl-thiazol-2-yl)-phenyl, and s is 0;

the compound wherein Y is thiazol-2-yl, Z is 4-(3-(4-chlorophenyl)-4,5,6,7-tetrahydroindazol-2-yl)-phenyl, and s is 0;

the compound wherein Y is thiazol-2-yl, Z is 4-(4-(2-chlorophenyl)-thiazol-2-yl)-phenyl, and s is 0;

the compound wherein Y is thiazol-2-yl, Z is 4-(4-(2,4-dichlorophenyl)-thiazol-2-yl)-phenyl, and s is 0;

the compound wherein Y is thiazol-2-yl, Z is 4-(3-(3-trifluoromethylphenyl)-5,6-dihydro-4H-cyclopentapyrazol-2-yl)-phenyl, and s is 0;

the compound wherein Y is thiazol-2-yl, Z is 4-(4-(3,4-dichlorophenyl)-thiazol-2-yl)-phenyl, and s is 0;

the compound wherein Y is thiazol-2-yl, Z is 4-(4-(3-trifluoromethylphenyl)-thiazol-2-yl)-phenyl, and s is 0;

the compound wherein Y is thiazol-2-yl, Z is 2-phenyl-1H-indol-6-yl, and s is 0;

the compound wherein Y is thiazol-2-yl, Z is 4-(4-(4-chlorophenyl)-pyrazol-1-yl)-phenyl, and s is 0;

the compound wherein Y is 5-bromofuran-2-yl, Z is 4-(3-trifluoromethylphenyl)-phenyl, and s is 0;

the compound wherein Y is 5-fluoro-thien-2-yl, Z is 4-(3-trifluoromethylphenyl)-phenyl, and s is 0;

the compound wherein Y is 1-(4-trifluoromethylphenyl)-indol-5-yl, Z is thiazol-4-yl, and s is 0;

the compound wherein Y is 1-(4-trifluoromethylphenyl)-indol-5-yl, Z is thiazol-2-yl, and s is 0;

the compound wherein Y is 1-(4-trifluoromethylphenyl)-indol-5-yl, Z is 1H-pyrrol-2-yl, and s is 0;

the compound wherein Y is thiazol-2-yl, Z is 3-(4-trifluoromethylphenyl)-1H-indol-6-yl, and s is 0;

the compound wherein Y is thiazol-2-yl, Z is 3-(3-trifluoromethylphenyl)-1H-indol-6-yl, and s is 0;

the compound wherein Y is thiazol-2-yl, Z is 5-phenyl-benzofuran-2-yl, and s is 0;

the compound wherein Y is thiazol-2-yl, Z is 5-(3-trifluoromethylphenyl)-benzofuran-2-yl, and s is 0;

the compound wherein Y is thiazol-4-yl, Z is 3-(4-trifluoromethylphenyl)-1H-indol-6-yl, and s is 0;

the compound wherein Y is thiazol-4-yl, Z is 3-(3-trifluoromethylphenyl)-1H-indol-6-yl, and s is 0;

the compound wherein Y is thiazol-2-yl, Z is 3-methyl-5-phenyl-benzothien-2-yl, and s is 0;

the compound wherein Y is thiazol-2-yl, Z is 1-methyl-3-(4-trifluoromethylphenyl)-indol-6-yl, and s is 0;

the compound wherein Y is thiazol-2-yl, Z is 1-(4-fluorophenyl)-4-fluoro-indol-5-yl, and s is 0;

the compound wherein Y is thiazol-2-yl, Z is 1-(4-fluorophenyl)-6-fluoro-indol-5-yl, and s is 0;

the compound wherein Y is thiazol-2-yl, Z is 1-(4-fluorophenyl)-7-fluoro-indol-5-yl, and s is 0;

the compound wherein Y is thiazol-2-yl, Z is 4-(3-trifluoromethylphenyl)-5-methylthien-2-yl, and s is 0;

the compound wherein Y is thiazol-2-yl, Z is 5-(4-trifluoromethylphenyl)-4-methylthien-2-yl, and s is 0;

the compound wherein Y is thiazol-2-yl, Z is 5-(4-fluorophenyl)-4-methyl-thien-2-yl, and s is 0;

the compound wherein Y is thiazol-2-yl, Z is 5-(3-trifluoromethylphenyl)-4-methylthien-2-yl, and s is 0;

the compound wherein Y is thiazol-2-yl, Z is 1-(4-fluorophenyl)-7-methyl-indol-5-yl, and s is 0;

the compound wherein Y is thiazol-2-yl, Z is 1-(3-trifluoromethylphenyl)-indol-5-yl, and s is 0;

the compound wherein Y is thiazol-2-yl, Z is 1-(4-trifluoromethylphenyl)-indol-5-yl, and s is 0;

the compound wherein Y is thiazol-4-yl, Z is 1-(4-fluorophenyl)-indol-5-yl, and s is 0;

the compound wherein Y is thiazol-4-yl, Z is 1-(4-trifluoromethylphenyl)-indol-5-yl, and s is 0;

the compound wherein Y is thiazol-2-yl, Z is 1-phenyl-indazol-5-yl, and s is 0;

the compound wherein Y is thiazol-2-yl, Z is 4-(5-trifluoromethylthien-2-yl)-phenyl, and s is 0;

the compound wherein Y is thiazol-2-yl, Z is 1-(3,4-difluorophenyl)-indol-5-yl, and s is 0;

the compound wherein Y is thiazol-4-yl, Z is 1-(3,4-difluorophenyl)-indol-5-yl, and s is 0;

the compound wherein Y is thiazol-2-yl, Z is 1-(2,4-difluorophenyl)-indol-5-yl, and s is 0;

the compound wherein Y is thiazol-2-yl, Z is 1-(4-fluorophenyl)-3-chloro-indol-5-yl, and s is 0;

the compound wherein Y is 1H-pyrrol-2-yl, Z is 1-(3,4-difluorophenyl)-indol-5-yl, and s is 0;

the compound wherein Y is thiazol-2-yl, Z is 1-(3,4,5-trifluoro-phenyl)-indol-5-yl, and s is 0;

the compound wherein Y is thiazol-2-yl, Z is 1-(3-fluorophenyl)-3-methyl-indol-5-yl, and s is 0;

the compound wherein Y is thiazol-2-yl, Z is 1-(4-trifluoromethoxyphenyl)-indol-5-yl, and s is 0;

the compound wherein Y is thiazol-4-yl, Z is 1-(4-trifluoromethoxyphenyl)-indol-5-yl, and s is 0;

the compound wherein Y is thiazol-2-yl, Z is 1-(3,5-difluorophenyl)-indol-5-yl, and s is 0;

the compound wherein Y is thiazol-2-yl, Z is 1-(3-fluoro-4-chlorophenyl)-indol-5-yl, and s is 0;

the compound wherein Y is thiazol-2-yl, Z is 1-(2,5-difluorophenyl)-indol-5-yl, and s is 0;

the compound wherein Y is thiazol-2-yl, Z is 1-(3-trifluoromethoxyphenyl)-indazol-5-yl, and s is 0;

the compound wherein Y is thiazol-2-yl, Z is 1-(4-cyano-3-methylphenyl)-indol-5-yl, and s is 0;

the compound wherein Y is thiazol-2-yl, Z is 2-(3-trifluoromethoxyphenyl)-indazol-5-yl, and s is 0;

the compound wherein Y is thiazol-2-yl, Z is 3-methoxy-4-phenyl-phenyl, and s is 0;

the compound wherein Y is thiazol-2-yl, Z is 2-methyl-5-phenyl-furan-3-yl, and s is 0;

the compound wherein Y is thiazol-2-yl, Z is 2-trifluoromethyl-5-phenyl-furan-3-yl, and s is 0;

the compound wherein Y is thiazol-4-yl, Z is 2-(4-chlorophenyl)-benzoxazol-7-yl, and s is 0;

the compound wherein Y is thiazol-4-yl, Z is 2-(3-chlorophenyl)-4-methyl-thiazol-5-yl, and s is 0;

the compound wherein Y is thiazol-4-yl, Z is 2-phenyl-benzoxazol-5-yl, and s is 0;

the compound wherein Y is biphenyl-4-yl, Z is 1H-pyrrol-2-yl, and s is 0;

the compound wherein Y is thiazol-4-yl, Z is 2-(4-chlorophenyl)-4-methyl-thiazol-5-yl, and s is 0;

the compound wherein Y is thiazol-2-yl, Z is 2-phenyl-5-trifluoromethyl-oxazol-4-yl, and s is 0;

the compound wherein Y is thiazol-4-yl, Z is 2-(4-fluorophenyl)-4-methyl-thiazol-5-yl, and s is 0;

the compound wherein Y is thiazol-2-yl, Z is 2-(pyridin-4-yl)-3H-benzimidazol-4-yl, and s is 0;

the compound wherein Y is thiazol-4-yl, Z is 2-(2-fluorophenyl)-1H-benzimidazol-4-yl, and s is 0;

the compound wherein Y is thiazol-4-yl, Z is 2-(3-chlorophenyl)-3H-benzimidazol-4-yl, and s is 0;

the compound wherein Y is thiazol-4-yl, Z is 2-phenyl-3H-benzimidazol-4-yl, and s is 0;

the compound wherein Y is thiazol-2-yl, Z is 2-(3-fluorophenyl)-1H-benzimidazol-4-yl, and s is 0;

the compound wherein Y is thiazol-2-yl, Z is 1-phenyl-5-trifluoromethyl-pyrazol-4-yl, and s is 0;

the compound wherein Y is thiazol-4-yl, Z is 2-(4-fluorophenyl)-1H-benzimidazol-4-yl, and s is 0;

the compound wherein Y is thiazol-4-yl, Z is 2-(2-chlorophenyl)-1H-benzimidazol-4-yl, and s is 0;

the compound wherein Y is thiazol-4-yl, Z is 2-(3,5-dichlorophenyl)-thiazol-4-yl, and s is 0;

the compound wherein Y is thiazol-4-yl, Z is 2-methyl-5-phenyl-furan-3-yl, and s is 0;

the compound wherein Y is thiazol-4-yl, Z is 5-phenyl-2-trifluoromethyl-furan-3-yl, and s is 0;

the compound wherein Y is cyclopentyl, Z is biphenyl-4-yl, and s is 0;

the compound wherein Y is thiazol-4-yl, Z is 2-furan-2-yl-3H-benzimidazol-4-yl, and s is 0;

the compound wherein Y is biphenyl-4-yl, Z is pyrimidin-2-yl, and s is 0;

the compound wherein Y is biphenyl-4-yl, Z is thiazol-2-yl, s is 1, and $R^1$ is 2-phenyl;

the compound wherein Y is biphenyl-4-yl, Z is thiazol-4-yl, s is 1, and $R^1$ is 2-phenyl;

the compound wherein Y is thiazol-4-yl, Z is 2-phenyl-5-trifluoromethyl-oxazol-4-yl, and s is 0;

the compound wherein Y is thiazol-2-yl, Z is biphenyl-4-yl, s is 1, and $R^1$ is 3-phenyl;

the compound wherein Y is thiazol-2-yl, Z is 2-fluoro-4-phenyl-phenyl, and s is 0;

the compound wherein Y is thiazol-4-yl, Z is 3-methyl-4-phenyl-phenyl, and s is 0;

the compound wherein Y is thiazol-2-yl, Z is 2-(3-trifluoromethylphenyl)-4-methyl-thiazol-5-yl, and s is 0;

the compound wherein Y is thiazol-4-yl, Z is 1-(3-trifluoromethylphenyl)-indol-5-yl, and s is 0;

the compound wherein Y is trifluoromethyl, Z is 1-(5-chloropyridin-2-yl)-indol-5-yl, and s is 0;

the compound wherein Y is thiazol-2-yl, Z is 1-(2-methylpyridin-4-yl)-indol-5-yl, and s is 0;

the compound wherein Y is thiazol-2-yl, Z is 1-(1-phenylethyl)-indazol-5-yl, and s is 0;

the compound wherein Y is thiazol-2-yl, Z is 4-(5-(4-fluorophenyl)-pyrazol-1-yl)-phenyl, and s is 0;

the compound wherein Y is thiazol-2-yl, Z is 4-(3-methylindol-1-yl)-phenyl, and s is 0;

the compound wherein Y is thiazol-2-yl, Z is 1-(4-fluorophenyl)-4-chloro-indol-5-yl, and s is 0;

the compound wherein Y is thiazol-2-yl, Z is 1-(4-fluorophenyl)-6-methyl-indol-5-yl, and s is 0;

the compound wherein Y is thiazol-2-yl, Z is 1-(4-fluorophenyl)-6-chloro-indol-5-yl, and s is 0;

the compound wherein Y is thiazol-2-yl, Z is 1-(3-cyano-4-fluorophenyl)-indol-5-yl, and s is 0; the compound wherein Y is thiazol-2-yl, Z is 1-(3-aminocarbonyl-4-fluorophenyl)-indol-5-yl, and s is 0;

the compound wherein Y is thiazol-2-yl, Z is 1-(3-trifluoromethylphenyl)-indazol-5-yl, and s is 0;

the compound wherein Y is thiazol-2-yl, Z is 2-(3-trifluoromethylphenyl)-indazol-5-yl, and s is 0;

the compound wherein Y is thiazol-4-yl, Z is 1-(4-cyano-3-methylphenyl)-indol-5-yl, and s is 0;

the compound wherein Y is thiazol-4-yl, Z is 2-(3-trifluoromethoxyphenyl)-indazol-5-yl, and s is 0;

the compound wherein Y is 5-chloro-thien-2-yl, Z is 1-(4-fluorophenyl)-indol-5-yl, and s is 0;

the compound wherein Y is 3-fluorophenyl, Z is 1-(4-fluorophenyl)-indol-5-yl, and s is 0;

the compound wherein Y is 5-chloro-furan-2-yl, Z is 1-(4-fluorophenyl)-indol-5-yl, and s is 0;

the compound wherein Y is oxazol-2-yl, Z is 1-(4-fluorophenyl)-indol-5-yl, and s is 0;

the compound wherein Y is 5-fluoro-thien-2-yl, Z is 1-(4-fluorophenyl)-indol-5-yl, and s is 0;

the compound wherein Y is oxazol-4-yl, Z is 1-(4-fluorophenyl)-indol-5-yl, and s is 0; and the compound wherein Y is oxazol-5-yl, Z is 1-(4-fluorophenyl)-indol-5-yl, and s is 0 or a pharmaceutically acceptable salt thereof.

12. The method of claim 11 wherein the fibrosis affects at least one organ selected from the group consisting of skin, heart, liver, lung, and kidney.

13. The method of claim 11 wherein the fibrosis is selected from the group consisting of dermal scar formation, keloids, liver fibrosis, lung fibrosis, kidney fibrosis, glomerulosclerosis, pulmonary fibrosis, renal fibrosis, intestinal fibrosis, interstitial fibrosis, cystic fibrosis of the pancreas and lungs, injection fibrosis, endomyocardial fibrosis, mediastinal fibrosis, myelofibrosis, retroperitoneal fibrosis, progressive massive fibrosis, and nephrogenic systemic fibrosis.

14. The method of claim 11 wherein the fibrosis is liver fibrosis.

\* \* \* \* \*